United States Patent
Harrison et al.

(10) Patent No.: US 8,993,039 B2
(45) Date of Patent: *Mar. 31, 2015

(54) FIBER-CONTAINING CARBOHYDRATE COMPOSITION

(75) Inventors: Michael D. Harrison, Decatur, IL (US); Andrew J. Hoffman, Mount Zion, IL (US)

(73) Assignee: Tate & Lyle Ingredients Americas LLC, Hoffman Estates, IL (US)

( * ) Notice: Subject to any disclaimer, the term of this patent is extended or adjusted under 35 U.S.C. 154(b) by 842 days.

This patent is subject to a terminal disclaimer.

(21) Appl. No.: 11/872,791

(22) Filed: Oct. 16, 2007

(65) Prior Publication Data

US 2008/0175977 A1    Jul. 24, 2008

Related U.S. Application Data

(63) Continuation-in-part of application No. PCT/US2007/060961, filed on Jan. 24, 2007, and a continuation-in-part of application No. 11/532,219, filed on Sep. 15, 2006, now Pat. No. 8,057,840, and a
(Continued)

(51) Int. Cl.
*A23G 3/00*   (2006.01)
*A23L 1/236*  (2006.01)
(Continued)

(52) U.S. Cl.
CPC ............... *C12P 19/04* (2013.01); *A23C 9/1307* (2013.01); *A23C 19/082* (2013.01);
(Continued)

(58) Field of Classification Search
CPC .......... C12P 19/14; C12P 19/00; C12P 19/04; A23V 2002/00; A23V 2250/60; A23V 2250/28; A23V 2250/5062; A23V 2250/51; A23V 2250/5116; A23V 2250/5118; A23V 2250/61; A23L 1/2363; A23L 1/09; A23L 1/095

USPC ......... 426/564, 658, 660, 589, 622, 548, 659; 435/100, 101, 105, 98
IPC ..................... C12P 19/16; A23L 1/09
See application file for complete search history.

(56) References Cited

U.S. PATENT DOCUMENTS

| 2,613,206 | A | 10/1952 | Caldwell ................ 260/233.5 |
| 2,661,349 | A | 12/1953 | Caldwell et al. ............. 260/224 |

(Continued)

FOREIGN PATENT DOCUMENTS

| CA | 1031332 | 5/1978 |
| EP | 363741 A2 | 4/1990 |

(Continued)

OTHER PUBLICATIONS

Cho, Complex Carbohydrates in Foods, 1999.*

(Continued)

*Primary Examiner* — Rena L Dye
*Assistant Examiner* — Lela S Williams
(74) *Attorney, Agent, or Firm* — McDonnell Boehnen Hulbert & Berghoff LLP

(57) ABSTRACT

A food product comprising digestion resistant or slowly digestible oligosaccharide composition. The oligosaccharide composition can be produced by a process comprising producing an aqueous composition comprising at least one oligosaccharide and at least one monosaccharide by saccharification of starch, membrane filtering the aqueous composition to form a monosaccharide-rich stream and an oligosaccharide-rich stream, and recovering the oligosaccharide-rich stream. Alternatively, the oligosaccharide composition can be produced by a process comprising heating an aqueous feed composition with a solids concentration of at least about 70% by weight, comprising at least one monosaccharide or linear saccharide oligomer, to a temperature of at least about 40° C., and contacting the composition with at least one catalyst that accelerates the rate of cleavage or formation of glucosyl bonds for a time sufficient to cause formation of non-linear saccharide oligomers, wherein the product contains a higher concentration of non-linear saccharide oligomers than linear saccharide oligomers.

11 Claims, 15 Drawing Sheets

Related U.S. Application Data continuation-in-part of application No. 11/339,306, filed on Jan. 25, 2006, now Pat. No. 7,608,436, and a continuation-in-part of application No. 11/610,639, filed on Dec. 14, 2006, now abandoned.

(51) Int. Cl.

| | | |
|---|---|---|
| C12P 19/02 | (2006.01) | |
| C12P 19/04 | (2006.01) | |
| A23C 9/13 | (2006.01) | |
| A23C 19/082 | (2006.01) | |
| A23C 19/09 | (2006.01) | |
| A23G 3/42 | (2006.01) | |
| A23G 9/32 | (2006.01) | |
| A23G 9/34 | (2006.01) | |
| A23L 1/00 | (2006.01) | |
| A23L 1/09 | (2006.01) | |
| A23L 1/164 | (2006.01) | |
| A23L 1/24 | (2006.01) | |
| A23L 1/30 | (2006.01) | |
| A23L 1/308 | (2006.01) | |
| A23L 1/39 | (2006.01) | |
| A23L 1/40 | (2006.01) | |
| A23L 2/52 | (2006.01) | |
| A23L 2/60 | (2006.01) | |

(52) U.S. Cl.
CPC ............ *A23C 19/0904* (2013.01); *A23G 3/42* (2013.01); *A23G 9/322* (2013.01); *A23G 9/34* (2013.01); *A23L 1/0061* (2013.01); *A23L 1/0076* (2013.01); *A23L 1/09* (2013.01); *A23L 1/1641* (2013.01); *A23L 1/24* (2013.01); *A23L 1/30* (2013.01); *A23L 1/308* (2013.01); *A23L 1/39* (2013.01); *A23L 1/40* (2013.01); *A23L 2/52* (2013.01); *A23L 2/60* (2013.01); *A23G 2200/06* (2013.01); *A23V 2002/00* (2013.01)
USPC .......... 426/658; 426/548; 426/659; 435/105; 435/101

(56) References Cited

U.S. PATENT DOCUMENTS

| | | | |
|---|---|---|---|
| 3,337,414 A | 8/1967 | Wilson | |
| 3,535,123 A | 10/1970 | Heady | |
| 3,729,380 A | 4/1973 | Sugimoto et al. ........... 195/31 R |
| 4,247,568 A | 1/1981 | Carrington et al. | |
| 4,521,252 A * | 6/1985 | Miyake et al. ............... 127/46.3 |
| 4,618,579 A * | 10/1986 | Dwiggins et al. .............. 435/96 |
| 4,619,831 A | 10/1986 | Sharma ........................... 426/93 |
| 4,626,288 A | 12/1986 | Trzasko et al. ................ 106/210 |
| 4,631,195 A | 12/1986 | Colliopoulos et al. | |
| 4,698,232 A * | 10/1987 | Sheu et al. ..................... 426/572 |
| 4,782,045 A | 11/1988 | Machida et al. | |
| 4,937,091 A | 6/1990 | Zallie et al. ................... 426/582 |
| 4,956,458 A | 9/1990 | Luo et al. | |
| 5,051,271 A * | 9/1991 | Iyengar et al. ................ 426/658 |
| 5,089,171 A | 2/1992 | Chiu ............................ 252/315.3 |
| 5,139,575 A | 8/1992 | Matsuda et al. ................ 127/23 |
| 5,281,276 A | 1/1994 | Chiu et al. ...................... 127/65 |
| 5,364,652 A | 11/1994 | Ohkuma et al. | |
| 5,368,878 A | 11/1994 | Smick et al. .................. 426/646 |
| 5,372,835 A | 12/1994 | Little et al. .................... 426/573 |
| 5,376,399 A | 12/1994 | Dreese et al. .................. 426/658 |
| H1394 H | 1/1995 | Dreese ........................... 426/603 |
| H1395 H | 1/1995 | Prosser ......................... 426/633 |
| 5,378,286 A | 1/1995 | Chiou et al. .................... 127/36 |
| 5,378,491 A | 1/1995 | Stanley et al. ................ 426/661 |
| 5,387,426 A | 2/1995 | Harris et al. .................. 426/573 |
| 5,395,640 A | 3/1995 | Harris et al. .................. 426/573 |
| 5,409,542 A | 4/1995 | Henley et al. .................. 127/65 |
| 5,424,418 A | 6/1995 | Duflot | |
| 5,436,019 A | 7/1995 | Harris et al. .................. 426/573 |
| 5,472,732 A | 12/1995 | Ohkuma et al. .............. 426/658 |
| 5,496,861 A | 3/1996 | Rouse et al. .................. 514/778 |
| 5,573,794 A | 11/1996 | Duflot | |
| 5,593,503 A | 1/1997 | Shi et al. .......................... 127/71 |
| 5,651,936 A | 7/1997 | Reed et al. ........................ 420/3 |
| 5,698,437 A | 12/1997 | Matsuda et al. | |
| 5,711,986 A | 1/1998 | Chiu et al. .................... 426/658 |
| 5,714,600 A | 2/1998 | McNaught et al. ........... 536/102 |
| 5,849,090 A | 12/1998 | Haralampu et al. ............ 127/65 |
| 5,886,168 A | 3/1999 | Brumm ........................ 536/103 |
| 5,902,410 A | 5/1999 | Chiu et al. ....................... 127/71 |
| 5,904,941 A | 5/1999 | Xu et al. ......................... 426/52 |
| 5,962,047 A | 10/1999 | Gross et al. ..................... 426/48 |
| 6,013,299 A | 1/2000 | Haynes et al. ................ 426/549 |
| 6,043,229 A | 3/2000 | Kettlitz et al. .................. 514/60 |
| 6,054,302 A | 4/2000 | Shi et al. .......................... 435/95 |
| 6,090,594 A | 7/2000 | Kettlitz et al. .................. 435/98 |
| 6,113,976 A | 9/2000 | Chiou et al. .................. 426/661 |
| 6,248,375 B1 | 6/2001 | Gilles et al. | |
| 6,274,567 B1 | 8/2001 | Brown et al. ................... 514/60 |
| 6,299,924 B1 | 10/2001 | Chiu et al. .................... 426/573 |
| 6,303,174 B1 | 10/2001 | McNaught et al. ........... 426/549 |
| 6,348,452 B1 | 2/2002 | Brown et al. ................... 514/60 |
| 6,352,733 B1 | 3/2002 | Haynes et al. ................ 426/549 |
| 6,423,364 B1 | 7/2002 | Altemueller et al. ......... 426/634 |
| 6,468,355 B1 | 10/2002 | Thompson et al. ............. 127/71 |
| 6,528,498 B2 | 3/2003 | Brown et al. ................... 514/60 |
| 6,613,373 B2 | 9/2003 | Haynes et al. ................ 426/549 |
| 6,623,943 B2 | 9/2003 | Schmiedel et al. ............. 435/98 |
| 6,664,389 B1 | 12/2003 | Shi et al. ....................... 536/102 |
| 6,670,155 B2 | 12/2003 | Antrim et al. ................... 435/95 |
| 6,740,350 B2 * | 5/2004 | Pfeiffer ......................... 426/572 |
| 6,762,346 B2 | 7/2004 | Kossmann et al. ........... 800/284 |
| 6,844,172 B2 | 1/2005 | Bergsma et al. ................ 435/98 |
| 6,890,571 B2 | 5/2005 | Shi et al. .......................... 426/28 |
| 6,896,915 B2 | 5/2005 | Shi et al. .......................... 426/20 |
| 6,927,048 B2 | 8/2005 | Verser et al. .................. 435/161 |
| 6,929,817 B2 | 8/2005 | Shi et al. ....................... 426/661 |
| 7,081,261 B2 | 7/2006 | Shi et al. .......................... 426/28 |
| 2003/0045504 A1 | 3/2003 | Brown et al. ................... 514/60 |
| 2003/0134394 A1 | 7/2003 | Antrim et al. ................... 435/95 |
| 2003/0215499 A1 | 11/2003 | Shi et al. ....................... 424/465 |
| 2004/0092732 A1 | 5/2004 | Antrim et al. ............. 536/123.13 |
| 2005/0095350 A1 | 5/2005 | Barresi et al. ................. 426/658 |
| 2005/0159329 A1 | 7/2005 | Fuertes et al. | |
| 2006/0188633 A1 | 8/2006 | Matsuda et al. | |
| 2006/0210696 A1 * | 9/2006 | Liu et al. ...................... 426/658 |
| 2007/0087084 A1 * | 4/2007 | Coleman et al. ................ 426/89 |
| 2007/0172931 A1 * | 7/2007 | Harrison et al. .............. 435/101 |
| 2007/0184177 A1 * | 8/2007 | Harrison et al. .............. 426/660 |

FOREIGN PATENT DOCUMENTS

| | | |
|---|---|---|
| EP | 0452262 | 4/1991 |
| EP | 486936 A1 | 5/1992 |
| EP | 487000 A1 | 5/1992 |
| EP | 529893 A1 | 3/1993 |
| EP | 529894 A1 | 3/1993 |
| EP | 553368 A1 | 8/1993 |
| EP | 0 499 648 B1 | 12/1993 |
| EP | 806434 A1 | 11/1997 |
| EP | 0 884 384 | 12/1998 |
| EP | 0 688 872 B1 | 3/1999 |
| EP | 1 088 832 | 4/2001 |
| EP | 0 846 704 | 3/2002 |
| EP | 1 362 869 | 11/2003 |
| EP | 1 382 687 A1 | 1/2004 |
| EP | 0875585 B1 | 1/2004 |
| JP | 61-205494 | 9/1986 |
| JP | 61-212296 | 9/1986 |
| JP | 61219392 | 9/1986 |
| JP | 61-22777 | 10/1986 |
| JP | S62-91502 | 4/1987 |
| JP | 63109791 | 5/1988 |

(56) References Cited

FOREIGN PATENT DOCUMENTS

| | | |
|---|---|---|
| JP | S63-109790 | 5/1988 |
| JP | S63-291588 | 11/1988 |
| JP | H01-012762 | 3/1989 |
| JP | 02-100695 | 4/1990 |
| JP | 03-163101 | 7/1991 |
| JP | 03175989 | 7/1991 |
| JP | 04-135495 | 5/1992 |
| JP | 04-237497 | 8/1992 |
| JP | 04290809 A | 10/1992 |
| JP | H06-32802 | 2/1994 |
| JP | H07-191 | 1/1995 |
| JP | H07-59585 | 3/1995 |
| JP | 07-227300 | 8/1995 |
| JP | 10080294 A | 3/1998 |
| JP | 10191931 A | 7/1998 |
| JP | 11-056336 | 3/1999 |
| JP | 2001-011101 | 1/2001 |
| JP | 2001-031574 | 2/2001 |
| JP | 231469 A | 8/2001 |
| JP | 2003-144187 | 5/2003 |
| JP | 2005-047829 | 2/2005 |
| WO | WO91/07106 | 5/1991 |
| WO | WO93/03629 | 3/1993 |
| WO | WO96/08261 | 3/1996 |
| WO | WO96/09815 | 4/1996 |
| WO | WO98/15347 | 4/1998 |
| WO | WO 99/28490 | 6/1999 |
| WO | WO00/14249 | 3/2000 |
| WO | 0167895 A1 | 9/2001 |
| WO | 03085139 A1 | 10/2003 |
| WO | WO 2004/031244 A1 | 4/2004 |
| WO | WO2005/040223 | 5/2005 |
| WO | WO2006/041563 | 4/2006 |
| WO | 2006101648 A1 | 9/2006 |
| WO | WO2008/085529 | 7/2008 |

OTHER PUBLICATIONS

Russell, The Nutrition and Health Dictionary, Corn Syr1995.*
PCT/US2008/078904 International Search Report (Dec. 15, 2008).
Sievert et al., *Cereal Chemistry* 66:342-347 (1989).
Sievert et al., *Cereal Chemistry* 67:217-221 (1990).
Nikolov et al., *Biotechnology and Bioengineering* 34:694-704 (1989).
Bourquelot et al., *Journ de Pharm et de Chim* 7:569-573, 598 (Jun. 16, 1912) (translation attached).
El-Sayed et al., *Acta Alimentaria* 23:43-58 (1994).
Hayakawa, Y.; "New Knowledge of Oligosaccharide;" Japan Innovative Food Ingredients Research Center; pp. 169-170; pp. 176-177; Nov. 20, 1998.
Fuwa, E.; Amyloid Science Dictionary; pp. 447-448, pp. 532; Mar. 20, 2003.
Kawazoe, K.; Food Chemicals 4; pp. 98; Dec. 20, 1990.
Goulas, et al.; "Purification of Oligosaccharides by Nanofiltration;" Journal of Membrane Science 209; pp. 321-335; 2002.
European Extended Search Report dated Oct. 22, 2013; Appl. No. EP13181573.0-1358; 9 pages.
Rastall et al., (Dec. 1992) "Enzymatic Synthesis of Oligosaccharides," Biotechnology and Genetic Engineering Reviews, vol. 10:1, pp. 253-282.
Pontoh et al., (1995) "Glucose Syrup Production from Indonesian Palm and Cassava Starch," Food Research Internationa, vol. 28, No. 4, pp. 379-385.
K.Okhuma et al., "Pyrolysis of STarch and Its Digestibility by Enzymes—Characterization of Indigestible Dextrin," Starch Science (Denpun Kagaku), 37(2), 107-114 (1990) (provided as English Translation).
H. Fuwa et al., Eds., Dictionary of Starch Science, 133-36 (2003) (provided as English translation).

* cited by examiner

FIBER-CONTAINING CARBOHYDRATE COMPOSITION

This application is a continuation-in-part of PCT/US2007/60961, filed on Jan. 24, 2007, and is a continuation-in-part of each of the following U.S. application Ser. No. 11/339,306, filed on Jan. 25, 2006 now U.S. Pat. No. 7,608,436, Ser. No. 11/532,219, filed on Sep. 15, 2006 now U.S. Pat. No. 8,057,840, and Ser. No. 11/610,639, filed on Dec. 14, 2006 now abandoned, with all of which it was copending, and all of which are incorporated herein by reference.

BACKGROUND OF THE INVENTION

A variety of carbohydrates are used in food products, such as various sugars and starches. Many of these carbohydrates are digested in the human stomach and small intestine. Dietary fiber in food products, in contrast, is generally not digested in the stomach or small intestine, but is potentially fermentable by microorganisms in the large intestine.

There is an interest in developing ingredients that are suitable for use in food products and that are either non-digestible or only digestible to a limited extent, in order to enhance the dietary fiber content or reduce the caloric content of the food. These modifications have certain health benefits.

There is a need for edible materials which have a reduced content of easily digestible carbohydrates, and which can be used in place of, or in addition to, conventional carbohydrate products in foods.

SUMMARY OF THE INVENTION

One aspect of the invention is a process for making an oligosaccharide composition. The process comprises producing an aqueous composition that comprises at least one oligosaccharide and at least one monosaccharide by saccharification of starch; membrane filtering the aqueous composition to form a monosaccharide-rich stream and an oligosaccharide-rich stream; and recovering the oligosaccharide-rich stream. In one embodiment of the invention, the oligosaccharide-rich stream is slowly digestible by the human digestive system. "Slowly digestible" as the term is used herein means that a substantial quantity (e.g., at least about 50% on a dry solids basis, and in some cases at least about 75%, or at least about 90%) of the carbohydrates present in the stream are either not digested at all in the human stomach and small intestine, or are only digested to a limited extent. In another embodiment of the invention, the oligosaccharide-rich stream is resistant to digestion by the human digestive system Both in vitro and in vivo tests can be performed to estimate rate and extent of carbohydrate digestion in humans. The "Englyst Assay" is an in vitro enzyme test that can be used to estimate the amounts of a carbohydrate ingredient that are rapidly digestible, slowly digestible or resistant to digestion (European Journal of Clinical Nutrition (1992) Volume 46 (Suppl. 2), pages S33-S50). Thus, any reference herein to "at least about 50% by weight on a dry solids basis" of a material being slowly digestible, or to a material being "primarily slowly digestible," means that the sum of the percentages that are classified as slowly digestible or as resistant by the Englyst assay totals at least about 50%. Likewise, any reference herein to "at least about 50% by weight on a dry solids basis" of a material being digestion-resistant, or to a material being "primarily digestion-resistant," means that the percentage that is classified as resistant by the Englyst assay is at least about 50%.

In one embodiment of the process, the aqueous composition that is produced by saccharification of starch, followed by isomerization, comprises dextrose, fructose, and a mixture of oligosaccharides. This aqueous composition can be nano-filtered to separate it into the monosaccharide-rich permeate stream and the oligosaccharide-rich retentate stream. The oligosaccharide-rich stream can comprise at least about 50% by weight oligosaccharides on a dry solids basis, or in some cases at least about 90%. In certain embodiments of the process, the oligosaccharide-rich stream will still comprise a minor amount of dextrose and fructose. "A minor amount" is used herein to mean less than 50% by weight on a dry solids basis.

The process, can, in some embodiments, also include one or more of the following steps: (1) contacting the oligosaccharide-rich stream with an isomerization enzyme, such that at least some of the dextrose is converted to fructose, thereby producing an isomerized oligosaccharide-rich stream; (2) membrane filtering the oligosaccharide-rich stream to produce a second monosaccharide-rich stream and a second oligosaccharide-rich stream that comprises more than about 90% by weight oligosaccharides on a dry solids basis as well as a minor amount of monosaccharides; (3) hydrogenating the oligosaccharide-rich stream to convert at least some of the monosaccharides therein to alcohols, thereby producing a hydrogenated oligosaccharide-rich stream; (4) contacting the oligosaccharide-rich stream with a glucosidase enzyme to create a reversion product such that at least some of any residual monosaccharides present in the stream are covalently bonded to oligosaccharides or other monosaccharides; and (5) reducing the color of the oligosaccharide-rich stream by contacting it with activated carbon.

Another aspect of the invention is a process for preparing saccharide oligomers. The saccharide oligomer composition produced by some embodiments of this process is primarily digestion resistant. In other embodiment, the composition is primarily slowly digestible. The process uses an aqueous feed composition that comprises at least one monosaccharide or linear saccharide oligomer, and that has a solids concentration of at least about 70% by weight. The feed composition is heated to a temperature of at least about 40° C., and is contacted with at least one catalyst that accelerates the rate of cleavage or formation of glucosyl bonds for a time sufficient to cause formation of non-linear saccharide oligomers. A product composition is produced that contains a higher concentration of non-linear saccharide oligomers than linear saccharide oligomers.

In one embodiment of the process, the at least one catalyst is an enzyme that accelerates the rate of cleavage or formation of glucosyl bonds. In another embodiment of the process, the at least one catalyst is an acid. In some embodiments of the process, acid and enzyme can be used in sequence, with the feed composition first being treated with enzyme and subsequently with acid, or vice versa.

Another aspect of the invention is an edible carbohydrate composition (sometimes referred to herein as an oligosaccharide composition) that comprises a major amount of oligosaccharides on a dry solids basis, and that is slowly digestible or resistant to digestion by the human digestive system. This composition can be produced by any of the above-described processes. "Major amount" is used herein to mean at least 50% by weight on a dry solids basis.

In one embodiment, the edible carbohydrate composition is produced by a process in which the oligosaccharide rich stream has a solids content not less than 70.0 percent mass/mass (m/m), and a reducing sugar content (dextrose equivalent), expressed as D-glucose, that is not less than 20.0 percent m/m calculated on a dry basis. This embodiment of the composition can be classified as corn syrup under food labeling regulations. In another embodiment, the oligosaccharide rich stream has a solids content not less than 70.0 percent mass/mass (m/m), and reducing sugar content (dextrose equivalent), expressed as D-glucose, less than 20.0 percent m/m calculated on a dry basis. This embodiment can be classified as maltodextrin under food labeling regulations.

Another aspect of the invention is an edible carbohydrate composition that comprises a major amount on a dry solids basis (i.e., greater than 50% by weight on a dry solids basis) of linear and non-linear saccharide oligomers, wherein the concentration of non-linear saccharide oligomers is greater than the concentration of linear saccharide oligomers. In some embodiments of the invention, the concentration of non-linear saccharide oligomers in the composition is at least twice as high as the concentration of linear saccharide oligomers.

Another embodiment is a carbohydrate composition that comprises linear and non-linear saccharide oligomers, wherein the composition contains about 10-70% by weight fiber on a dry solids basis and has a dextrose equivalent of about 25-65. In some embodiments, the composition contains about 30-40% by weight fiber on a dry solids basis and has a caloric value of about 2.5-3.5 kcal/g.

The product of this embodiment can be prepared by a process that comprises: heating an aqueous feed composition that comprises at least one monosaccharide or linear saccharide oligomer, and that has a solids concentration of at least about 70% by weight, to a temperature of at least about 40° C.; and contacting the feed composition with at least one catalyst that accelerates the rate of cleavage or formation of glucosyl bonds for a time sufficient to cause formation of non-linear saccharide oligomers, wherein a product composition is produced that (a) contains about 10-70% by weight fiber on a dry solids basis, and (b) has a dextrose equivalence of about 25-65. The at least one catalyst can be an acid, such as citric acid, hydrochloric acid, sulfuric acid, phosphoric acid, or a combination thereof. In one particular embodiment, the acid can be residual acid that is present in the feed composition from previous processing. In another embodiment, the at least one catalyst can be an enzyme that accelerates the rate of cleavage or formation of glucosyl bonds. Alternatively, the composition can be prepared by blending corn syrup with a composition prepared by one or more of the processes described herein.

Another aspect of the invention is a method of preparing a food product. The method comprises providing a food composition suitable for combination with a carbohydrate material, and combining the food composition with an edible carbohydrate composition that is slowly digestible or digestion-resistant, as described above.

Another aspect of the invention is a food product that comprises an edible carbohydrate composition as described above. The food product can be, for example, a bread, cake, cookie, cracker, extruded snack, soup, frozen dessert, fried food, pasta product, potato product, rice product, corn product, wheat product, dairy product, yogurt, confectionary, hard candy, nutritional bar, breakfast cereal, or beverage.

In one embodiment of the invention, the food product is selected from baked foods, breakfast cereal, anhydrous coatings (e.g., ice cream compound coating, chocolate), dairy products, confections, jams and jellies, beverages, fillings, extruded and sheeted snacks, gelatin desserts, snack bars, cheese and cheese sauces, edible and water-soluble films, soups, syrups, sauces, dressings, creamers, icings, frostings, glazes, pet food, tortillas, meat and fish, dried fruit, infant and toddler food, and batters and breadings. The edible carbohydrate composition, which is sometimes referred to herein as an oligosaccharide composition, can be present in the food product for one or more purposes, such as a complete or partial replacement for sweetener solids, or as a source of dietary fiber.

Another aspect of the invention is a method of controlling blood glucose in a mammal suffering from diabetes. The method comprises feeding to the mammal a food product as described above in various embodiments.

DESCRIPTION OF SPECIFIC EMBODIMENTS

Figure 1:
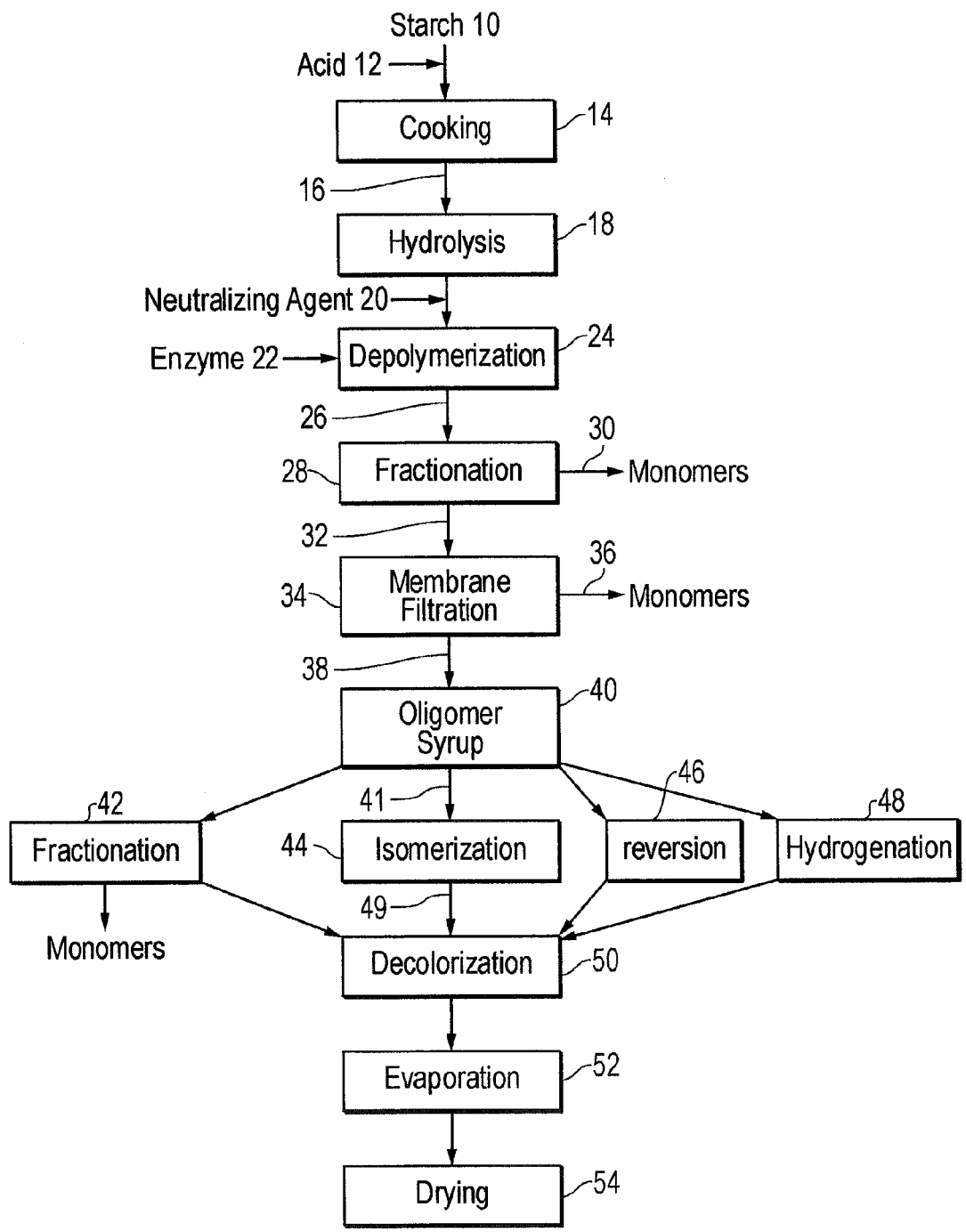
FIG. 1 is process flow diagram of one embodiment of the present invention.

One aspect of the present invention is a process for making a slowly digestible or digestion-resistant carbohydrate composition (e.g., saccharide oligomer composition) that is suitable for use in foods.

Both in vitro and in vivo tests can be performed to estimate the rate and extent of carbohydrate digestion in humans. The "Englyst Assay" is an in vitro enzyme test that can be used to estimate the amounts of a carbohydrate ingredient that are rapidly digestible, slowly digestible or resistant to digestion (European Journal of Clinical Nutrition (1992) Volume 46 (Suppl. 2), pages S33-S50).

It should be understood that the term "food" is used in a broad sense herein to include a variety of substances that can be ingested by humans, such as beverages and medicinal capsules or tablets.

The terms "oligosaccharides" and "saccharide oligomers" are used herein to refer to saccharides comprising at least two saccharide units, for example saccharides having a degree of polymerization ("DP") of about 2-30. For example, a disaccharide has a DP of 2.

In some embodiments of the invention, the aqueous feed composition includes at least one monosaccharide and at least one linear saccharide oligomer, and may contain several of each. In many cases, monosaccharides and oligosaccharides will make up at least about 70% by weight on a dry solids basis of the feed composition. It is generally helpful for the starting material to have as high a concentration of monosaccharides as possible, in order to maximize the yield of the desired oligomers. A high solids concentration tends to drive the equilibrium from hydrolysis toward condensation (reversion), thereby producing higher molecular weight products. Therefore the water content of the starting material is preferably relatively low. For example, in certain embodiments, the feed composition comprises at least about 75% dry solids by weight. ("Dry solids" is sometimes abbreviated herein as "ds.") In some cases, the feed composition comprises about 75-90% solids by weight, which will generally give the appearance of a viscous syrup or damp powder at room temperature.

Examples of suitable starting materials include, but are not limited to, syrups made by hydrolysis of starch, such as dextrose greens syrup (i.e., recycle stream of mother liquor from dextrose monohydrate crystallization), other dextrose syrups, corn syrup, and solutions of maltodextrin.

If the feed composition comprises maltodextrin, the process optionally can also include the steps of hydrolyzing the maltodextrin to form a hydrolyzed saccharide solution and concentrating the hydrolyzed saccharide solution to at least about 70% dry solids to form the feed composition. The concentrating and the contacting of the feed with the catalyst can occur simultaneously, or the concentrating can occur prior to contacting the feed composition with the catalyst.

The feed composition is contacted with the at least one catalyst for a period of time that can vary. In some cases, the contacting period will be at least about five hours. In some embodiments of the invention, the feed composition is contacted with the at least one catalyst for about 15-100 hours. In other embodiments, shorter contacting times can be used with higher temperatures, in some cases even less than one hour.

In one embodiment of the invention, enzymatic reversion is used to produce nonlinear oligosaccharides. The enzyme can be, for example, one that accelerates the rate of cleavage of alpha 1-2, 1-3, 1-4, or 1-6 glucosyl bonds to form dextrose residues. One suitable example is a glucoamylase enzyme composition, such as a commercial enzyme composition that is denominated as a glucoamylase. It should be understood that such a composition can contain some quantity of enzymes other than pure glucoamylase, and it should not be assumed that it is in fact glucoamylase itself that catalyzes the desired production of nonlinear oligosaccharides.

Therefore, the feed composition can be contacted with glucoamylase or any other enzyme that acts on dextrose polymers. The amount of enzyme can suitably be about 0.5-2.5% by volume of the feed composition. In some embodiments of the process, the feed composition is maintained at about 55-75° C. during the contacting with the enzyme, or in some cases about 60-65° C. At this temperature, depending on the water content, the material will become a liquid, or a mixture of liquid and solid. Optionally, the reaction mixture can be mixed or agitated to distribute the enzyme. The reaction mixture is maintained at the desired temperature for the time necessary to achieve the desired degree of reversion to non-linear oligomers. In some embodiments of the process, the feed composition is contacted with the enzyme for about 20-100 hours prior to inactivation of the enzyme, or in some cases, for about 50-100 hours prior to inactivation. Techniques for inactivating glucoamylase are well known in the field. Alternatively, instead of inactivating the enzyme, it can be separated by membrane filtration and recycled.

The resulting composition has a high concentration of non-linear oligosaccharides, such as isomaltose. This product composition contains a higher concentration of non-linear saccharide oligomers than linear saccharide oligomers. In some cases, the concentration of non-linear saccharide oligomers in the final composition is at least twice as high as the concentration of linear saccharide oligomers.

Gastrointestinal enzymes readily recognize and digest carbohydrates in which the dextrose units are linked alpha (1→4) ("linear" linkages). Replacing these linkages with alternative linkages (alpha (1→3), alpha (1→6) ("non-linear" linkages) or beta linkages, for example) greatly reduces the ability of gastrointestinal enzymes to digest the carbohydrate. This will allow the carbohydrates to pass on into the small intestines largely unchanged.

In some cases, the product composition comprises a minor amount (i.e., less than 50 wt % on a dry solids basis, and usually a much lower concentration) of residual monosaccharides. The process can include the additional step of removing at least some of the residual monosaccharides (and optionally other species as well) from the product composition by membrane filtration, chromatographic fractionation, or digestion via fermentation. The separated monosaccharides can be combined with other process streams, for example for production of dextrose or corn syrup. Alternatively, the separated monosaccharides can be recycled into the feed composition.

Another embodiment of the invention is a process that involves acid reversion of monosaccharides. The starting material is the same as described above with respect to the enzyme version of the process. A variety of acids can be used, such as hydrochloric acid, sulfuric acid, phosphoric acid, or a combination thereof. In some embodiments of the process, acid is added to the feed composition in an amount sufficient to make the pH of the feed composition no greater than about 4, or in some cases, in an amount sufficient to make the pH of the feed composition about 1.0-2.5, or about 1.5-2.0. In some embodiments, the solids concentration of the feed composition is about 70-90%, the amount of acid added to the feed is about 0.05%-0.25% (w/w) acid solids on syrup dry solids, and the feed composition is maintained at a temperature of about 70-90° C. during the contacting with the acid. As in the enzyme version of the process, the reaction conditions are maintained for a time sufficient to produce the desired oligomers, which in some embodiments of the process will be about 4-24 hours.

In one particular embodiment, the solids concentration of the feed composition is at least about 80% by weight, acid is added to the feed composition in an amount sufficient to make the pH of the composition about 1.8, and the feed composition is maintained at a temperature of at least about 80° C. for about 4-24 hours after it is contacted with the acid.

In another particular embodiment, the solids concentration of the feed composition is about 90-100% by weight, and the feed composition is maintained at a temperature of at least about 149° C. (300° F.) for about 0.1-15 minutes after it is contacted with the acid. The acid used to treat the feed can be a combination of phosphoric acid and hydrochloric acid (at the same concentrations discussed above). In one particular embodiment, the contacting of the feed composition with the acid takes place in a continuous pipe/flow through reactor.

By far the most plentiful glycosidic linkage in starch is the alpha-1,4 linkage, and this is the linkage most commonly broken during acid hydrolysis of starch. But acid-catalyzed reversion (condensation) can take place between any two hydroxyl groups, and, given the large variety of combinations and geometries available, the probability of an alpha-1,4 linkage being formed is relatively small. The human digestive system contains alpha amylases which readily digest the alpha-1,4 linkages of starch and corn syrups. Replacing these linkages with linkages unrecognized by enzymes in the digestive system will allow the product to pass through to the small intestines largely unchanged.

The saccharide distributions resulting from acid treatment are believed to be somewhat different than from enzyme treatment. It is believed that these acid-catalyzed condensation products will be less recognizable by the enzymes in the human gut than enzyme-produced products, and therefore less digestible.

The acid treatment progresses differently than enzyme treatment. Enzymes rapidly hydrolyze linear oligomers and slowly form non-linear oligomers, whereas with acid the reduction in linear oligomers and the increase in non-linear oligomers occur at comparable rates. Dextrose is formed rapidly by enzymatic hydrolysis of oligomers, and consumed slowly as non-linear condensation products are formed, whereas with acid dextrose concentrations increase slowly.

Optionally, enzymatic or acid reversion can be followed by hydrogenation. The hydrogenated product should have lower caloric content than currently available hydrogenated starch hydrolysates. In one embodiment, the hydrogenation can be used to decolorize the product composition without substantially changing its dextrose equivalence (DE).

In one version of the process, enzyme and acid can be used sequentially, in any order. For example, the at least one catalyst used in the first treatment can be enzyme, and the product composition can be subsequently contacted with an acid that accelerates the rate of cleavage or formation of glucosyl bonds. Alternatively, the at least one catalyst used in the first treatment can be acid, and the product composition can be subsequently contacted with an enzyme that accelerates the rate of cleavage or formation of glucosyl bonds.

In an embodiment of the process in which acid treatment is used first, followed by an enzyme treatment, the acid can be phosphoric acid, hydrochloric acid, or a combination thereof. In this embodiment, after being contacted with the enzyme, the composition can be contacted with an ion exchange resin. After being contacted with the ion exchange resin, the concentration in the composition of saccharide oligomers having a degree of polymerization of at least three can be at least about 50% by weight on a dry solids basis.

The product composition produced by the treatment with acid, enzyme, or both, has an increased concentration on a dry solids basis of non-linear saccharide oligomers. In some cases, the concentration of non-linear saccharide oligomers having a degree of polymerization of at least three (DP3+) in the product composition is at least about 20%, at least about 25%, at least about 30%, or at least about 50% by weight on a dry solids basis. In some embodiments, the concentration of non-linear saccharide oligomers in the product composition is at least twice as high as the concentration of linear saccharide oligomers.

In one particular embodiment, the concentration of non-linear saccharide oligomers in the product composition is at least about 90% by weight on a dry solids basis, and the concentration of isomaltose is at least about 70% by weight on a dry solids basis.

The product composition will often contain some quantity (typically less than 50% by weight on a dry solids basis, and often much less) of residual monosaccharides. Optionally, at least some of the residual monosaccharides (and other species) can be separated from the oligomers (for example by membrane filtration, chromatographic separation, or digestion via fermentation) and the monosaccharide stream can be recycled into the process feed. In this way, simple sugar syrups can be converted to high-value food additives.

The oligomer-rich syrup produced by the processes described herein can be used in foods to increase dietary fiber. The syrup contains naturally-occurring oligosaccharides that have both low viscosity and low glycemic index. Many of these oligomers will comprise at least one non-alpha-1,4 linkage. They should be highly fermentable in the large intestine, which give them added health benefits as prebiotics. In some embodiments of the invention, at least about 50% by weight on a dry solids basis of the product composition is slowly digestible.

The beneficial effects of oligosaccharides as dietary fiber have been well documented. Sugar oligomers that resist digestion in the small intestine but are fermentable in the large intestine have been shown to have several beneficial effects, such as reducing cholesterol, attenuating blood dextrose, and maintaining gastrointestinal health.

In one embodiment, the product is a carbohydrate composition that comprises linear and non-linear saccharide oligomers, contains about 10-70% by weight fiber on a dry solids basis, and has a dextrose equivalence (DE) of about 25-65. Fiber content can be measured by AOAC method 2001.03.

In this embodiment, the product can have an intermediate fiber content (i.e., higher than conventional corn syrup but lower than some of the compositions of the present invention that are described herein). When the feed is derived from corn, the product can be referred to as corn syrup fiber (CSF). In one embodiment, the CSF product contains about 30-40% by weight fiber on a dry solids basis and has a caloric value of about 2.5-3.5 kcal/g. We estimate that a 35% fiber CSF will result in a caloric content of 3 kcal/g, which is intermediate between a high fiber resistant corn syrup at 2 kcal/g and typical digestible carbohydrate at 4 kcal/g. This represents a caloric reduction of 25% compared to traditional sugars and starches.

In one embodiment, the process for making this product comprises (1) heating an aqueous feed composition that comprises at least one monosaccharide or linear saccharide oligomer, and that has a solids concentration of at least about 70% by weight, to a temperature of at least about 40° C., and (2) contacting the feed composition with at least one catalyst that accelerates the rate of cleavage or formation of glucosyl bonds for a time sufficient to cause formation of non-linear saccharide oligomers, wherein a product composition is produced that (a) contains about 10-70% by weight fiber on a dry solids basis, and (b) has a dextrose equivalence of about 25-65.

The catalyst can be acid (such as citric acid, hydrochloric acid, sulfuric acid, phosphoric acid, or a combination thereof), enzyme, or a combination of both acid and enzyme. The catalyst can be added during the process. Alternatively, in some situations there can be sufficient residual catalyst (e.g., food grade acid) present in the feed as a result of previous processing, so that no further catalyst needs to be added. Thus, in one embodiment, the process to make CSF comprises a simple heating step, with optional addition of food grade acid. This process can be easily implemented and integrated into existing corn syrup refinery operations.

We expect that the fiber fraction of this "direct reversion" CSF product will be lower molecular weight, have less complicated branching and will be more easily fermentable by colonic microbiota than the fiber fraction in the higher fiber resistant corn syrup (RCS). The DE of the CSF product can be targeted to match the DE of commercial corn syrup products. For example, CSF products with DE approximately equal to 26, 35, 43 and 63 would be matches for Staley 200, Staley 300, Staley 1300 and Sweetose 4300 traditional corn syrups, respectively.

Alternatively, the product can be prepared by blending conventional corn syrup (having little or no fiber) with a resistant corn syrup (having a fiber content of, for example, about 70% or greater). Syrups that are derived from grains other than corn can also be used.

The above-described product can be used as an ingredient in food products, as explained in more detail in other parts of this patent application. This product can have one or more benefits. For example, it can reduce the caloric content and increase the dietary fiber content of corn syrup, it can serve as a "drop in" replacement for traditional corn syrup in foods, it can provide appropriate fiber loading in products that use high levels of corn syrup, and it can provide a more economical approach to fiber supplementation in food.

FIG. 1 shows one embodiment of a process which can make use of the reversion technique described above. The process can begin with a starch, for example a vegetable starch. Conventional corn starch is one suitable example. The process will generally operate more efficiently if the beginning starch has a relatively high purity. In one embodiment, the high purity starch contains less than 0.5% protein on a dry solids basis. Although some of the following discussion focuses on corn, it should be understood that the present invention is also applicable to starches derived from other sources, such as potato and wheat, among others.

As shown in FIG. 1, the starch 10 can have acid 12 added to it and can then be gelatinized 14 in a starch cooker, for example in a jet cooker in which starch granules are contacted with steam. In one version of the process, the starch slurry, adjusted to a pH target of 3.5 by addition of sulfuric acid, is rapidly mixed with steam in a jet cooker and held at 149 to 152° C. (300 to 305° F.) for 4 minutes in a tail line. The gelatinized starch 16 is hydrolyzed 18 by exposure to acid at high temperature during jet cooking. The hydrolysis reduces the molecular weight of the starch and generates an increased percentage of monosaccharides and oligosaccharides in the composition. (As mentioned above, thee term "oligosaccharides" is used herein to refer to saccharides comprising at least two saccharide units, for example saccharides having a degree of polymerization (DP) of about 2-30.) A neutralizing agent 20, such as sodium carbonate, can be added to stop the acid hydrolysis, and then the composition can be further depolymerized 24 by contacting it with a hydrolytic enzyme 22. Suitable enzymes include alpha amylases such as Termamyl, which is available from Novozymes. This enzymatic hydrolysis further increases the percentage of monosaccharides and oligosaccharides present in the composition. The overall result of the hydrolysis by acid and enzyme treatment is to saccharify the starch. The saccharified composition can be isomerized to change the monosaccharide profile, for example to increase the concentration of fructose.

The saccharified composition 26 can then be purified, for example by chromatographic fractionation 28. In one embodiment that employs a sequential simulated moving bed (SSMB) chromatography procedure, a solution of mixed saccharides is pumped through a column filled with resin beads. Depending on the chemical nature of the resin, some of the saccharides interact with the resin more strongly leading to a retarded flow through the resin compared to saccharides that interact with the resin more weakly. This fractionation can produce one stream 30 that has a high content of monosaccharides, such as dextrose and fructose. High fructose corn syrup is an example of such a stream. The fractionation also produces a raffinate stream 32 (i.e., faster moving components through the resin bed) that has a relatively high concentration of oligosaccharides (e.g., about 5-15% oligosaccharides on a dry solids basis (d.s.b.)) and also contains a smaller concentration of monosaccharides such as dextrose and fructose. Although the term "stream" is used herein to describe certain parts of the process, it should be understood that the process of the present invention is not limited to continuous operation. The process can also be performed in batch or semi-batch mode.

The raffinate 32 can be further fractionated by membrane filtration 34, for example by nanofiltration, optionally with diafiltration. For example, these filtration steps can be performed using a Desal DK spiral wound nanofiltration cartridge at about 500 psi of pressure and at 40-60 degrees centigrade temperature. The fractionation described in step 34 could also be accomplished by sequential simulated moving bed chromatography (SSMB). The membrane filtration produces a permeate 36 (i.e., components that pass through the membrane) which comprises primarily monosaccharides, and a retentate 38 (i.e., components rejected by the membrane) which comprises primarily oligosaccharides. ("Primarily" as used herein means that the composition contains more of the listed component than of any other component on a dry solids basis.) The permeate 36 can be combined with the monomer stream 30 (e.g., high fructose corn syrup). The permeate is a monosaccharide-rich stream and the retentate is an oligosaccharide-rich stream. In other words, the nanofiltration concentrates the oligosaccharides in the retentate and the monosaccharides in the permeate, relative to the nanofiltration feed.

The retentate 38, which can be described as an oligosaccharide syrup 40, can have a sufficiently high content of oligosaccharides that are slowly digestible (e.g., at least about 50% by weight d.s.b., or in some cases at least about 90%) so that it can be dried or simply evaporated to a concentrated syrup and used as an ingredient in foods. However, in many cases, it will be useful to further process and purify this composition. Such purification can include one or more of the following steps. (Although FIG. 1 shows four such purification steps 42, 44, 46, and 48 as alternatives, it should be understood that two or more of these steps could be used in the process.)

The oligomers syrup 40 can be subjected to another fractionation 42, such as a membrane filtration, for example a second nanofiltration, in order to remove at least some of the residual monosaccharides, such as fructose and dextrose. Suitable nanofiltration conditions and equipment are as described above. This nanofiltration produces a permeate, which is a second monosaccharide-rich stream, which can be combined with the monomer stream 30. Alternatively, the further fractionation 42 could be done by chromatographic separation, for example, by simulated mixed-bed chromatography.

The syrup 41 can be isomerized 44 by contacting it with an enzyme such as dextrose isomerase. This will convert at least some of the residual dextrose present into fructose, which may be more valuable in certain situations.

As mentioned above, the syrup can be treated with an enzyme or acid to cause reversion or repolymerization 46, in which at least some of the monosaccharides that are still present are covalently bonded to other monosaccharides or to oligosaccharides, thereby reducing the residual monomer content of the syrup even further. Suitable enzymes for use in this step include glucosidases, such as amylase, glucoamylase, transglucosidase, and pullulanase. Cellulase enzymes may produce valuable reversion products for some applications.

The syrup can be hydrogenated 48 to convert at least some of any residual monosaccharides to the corresponding alcohols (e.g., to convert dextrose to sorbitol). When hydrogenation is included in the process, it will typically (but not necessarily) be the final purification step.

The purified oligomer syrup 49 produced by one or more of the above purification steps can then be decolorized 50. Decolorization can be done by treatment with activated carbon followed by microfiltration, for example. In continuous flow systems, syrup streams can be pumped through columns filled with granular activated carbon to achieve decolorization. The decolorized oligomer syrup can then be evaporated 52, for example to about greater than about 70% dry solids (d.s.), giving a product that comprises a high content of oligosaccharides (e.g., greater than 90% by wt d.s.b., and in some instances greater than 95%), and a correspondingly low monosaccharide content. The product comprises a plurality of saccharides which are slowly or incompletely digested by humans, if not totally indigestible. These sugars can include isomaltose, panose and branched oligomers having a degree of polymerization of four or greater.

The process conditions can be modified to recover the majority of the maltose in the feed either in the monomer-rich streams (30, 36) or in the oligomer product stream. For example, a nanofiltration membrane with a slightly more open pore size, such as Desal DL, operating at less than 500 psi pressure can be used to increase the amount of maltose in monomer-rich streams.

The product is suitable as an ingredient for foods, and is slowly digestible or resistant to digestion by the human digestive system. As mentioned above, some components of the product can be substantially entirely indigestible in the human stomach and small intestine. Depending on the starch source used, the product can be classified in some embodiments as corn syrup or wheat syrup, as those terms are used in food labeling. In cases where more open pore sizes are used in nanofiltration, a higher molecular weight oligomer syrup product classified as a maltodextrin can be obtained.

The oligosaccharide-containing syrup produced by the process can be added to foods as replacement or supplement for conventional carbohydrates. Thus, another aspect of the invention is a food product that comprises a carbohydrate composition that comprises a major amount on a dry solids basis of linear and non-linear saccharide oligomers, wherein the concentration of non-linear saccharide oligomers is greater than the concentration of linear saccharide oligomers. Specific examples of foods in which the syrup can be used include processed foods such as bread, cakes, cookies, crackers, extruded snacks, soups, frozen desserts, fried foods, pasta products, potato products, rice products, corn products, wheat products, dairy products, yogurts, confectioneries, hard candies, nutritional bars, breakfast cereals, and beverages. A food product containing the oligosaccharide syrup will have a lower glycemic response, lower glycemic index, and lower glycemic load than a similar food product in which a conventional carbohydrate, such as corn starch, is used. Further, because at least some of the oligosaccharides are either only digested to a very limited extent or are not digested at all in the human stomach or small intestine, the caloric content of the food product is reduced. The syrup is also a source of soluble dietary fiber.

The digestion-resistant oligomer syrup described above can be used as an ingredient in food products as a syrup, or it can first be concentrated to form syrup solids. In either form, it can be used in a number of ways. As mentioned above, this syrup can be derived from various starch sources, such as corn. In some instances in this patent, the phrase "digestion-resistant corn syrup" or "resistant corn syrup" (sometimes abbreviated as "RCS") will be used, but it should be understood that the invention is not limited to syrups or syrup solids that are derived from corn.

The digestion-resistant oligomer syrup can be added to food products as a source of soluble fiber. It can increase the fiber content of food products without having a negative impact on flavor, mouth feel, or texture.

The functionality of the digestion-resistant oligomer syrup is similar to corn syrup and sugar, which makes it suitable for complete or partial replacement of various nutritive sweeteners in food products. For example, the resistant syrup can be used for total or partial replacement of sucrose, high fructose corn syrup (HFCS), fructose, dextrose, regular corn syrup, or corn syrup solids in food products. As one particular example, the digestion-resistant syrup or digestion-resistant syrup solids can be used to replace other sweetener solids on a 1:1 basis, up to a complete replacement of the sugar solids. At high sweetener solids replacement levels, the sweetness of the food product could be decreased, but mouth feel and flavor release would remain substantially the same, while sugar and calorie content would be reduced. Also, the digestion-resistant syrup could be used as a bulking agent, replacing fat, flour, or other ingredients in a food formula. Alternatively, the digestion-resistant syrup can be used in food products in combination with sweeteners such as sucrose, HFCS, or fructose, resulting in no change in overall sweetness of the food product. As another example, the digestion-resistant syrup can be used in food products in combination with sucralose or other high intensity sweeteners, which allows sweetener replacement with no change in sweetness or mouth feel of the food product.

The digestion-resistant oligomer syrup can be used in food products in combination with resistant starch, polydextrose, or other fiber sources, to boost the fiber content of the food product, enhance physiological benefit from consumption of the product, reduce the caloric content, and/or enhance the nutritional profile of the product.

The digestion-resistant oligomer syrup can be used in food products in combination with bulking agents, such as sugar alcohols or maltodextrins, to reduce caloric content and/or to enhance nutritional profile of the product. The syrup can also be used as a partial replacement for fat in food products.

The digestion-resistant oligomer syrup can be used in food products as a tenderizer or texturizer, to increase crispness or snap, to improve eye appeal, and/or to improve the rheology of dough, batter, or other food compositions. The syrup can also be used in food products as a humectant, to increase product shelf life, and/or to produce a softer, moister texture. It can also be used in food products to reduce water activity or to immobilize and manage water. Additional uses of the syrup include: to replace egg wash and/or to enhance the surface sheen of a food product, to alter flour starch gelatinization temperature, to modify the texture of the product, and to enhance browning of the product.

At least in some embodiments of the invention, the digestion-resistant oligomer syrup has one or more of the following advantages: high solubility, which makes it relatively easy to incorporate into food compositions, such as batters and doughs; stability under elevated temperatures and/or acidic pH (some other soluble fibers, such as inulin, are not as stable), lower sweetness, clean flavor, and clear color. The properties of the syrup allow food products in which it is used to have a clean, label. In some embodiments of the invention, the digestion-resistant oligomer syrup contains about 2 calories per gram (d.s.b.), which can reduce the total calorie content of a food product.

The digestion-resistant oligomer syrup of the present invention can be used in a variety of types of food products. One type of food product in which the syrup can be very useful is bakery products (i.e., baked foods), such as cakes, brownies, cookies, cookie crisps, muffins, breads, and sweet doughs. Conventional bakery products can be relatively high in sugar and high in total carbohydrates. The use of the digestion-resistant syrup as an ingredient in bakery products can help lower the sugar and carbohydrate levels, as well as reduce the total calories, while increasing the fiber content of the bakery product.

There are two main categories of bakery products: yeast-raised and chemically-leavened. In yeast-raised products, like donuts, sweet doughs, and breads, the digestion-resistant oligomer syrup can be used to replace sugars, but a small amount of sugar may still be desired due to the need for a fermentation substrate for the yeast or for crust browning. Digestion-resistant oligomer syrup solids (e.g., digestion-resistant corn syrup solids) could be added in a manner similar to nutritive dry sweeteners, with other dry ingredients, and would require no special handling. The resistant corn syrup can be added with other liquids as a direct replacement for syrups or liquid sweeteners. The dough would then be processed under conditions commonly used in the baking industry including being mixed, fermented, divided, formed or extruded into loaves or shapes, proofed, and baked or fried. The product can be baked or fried using conditions similar to traditional products. Breads are commonly baked at temperatures ranging from 420° F. to 520° F. for 20 to 23 minutes and doughnuts can be fried at temperatures ranging from 400-415° F., although other temperatures and times could also be used. High intensity sweeteners can be added to doughs as required to obtain optimum sweetness and flavor profile.

Chemically leavened products typically have more sugar and may contain have a higher level of resistant corn syrup/solids. A finished cookie can contain 30% sugar, which could be replaced, entirely or partially, with resistant corn syrup/solids. These products could have a pH of 4-9.5, for example. The moisture content can be between 2-40%, for example.

The resistant corn syrup/solids is readily incorporated and may be added to the fat at the beginning of mixing during a creaming step or in a any method similar to the syrup or dry sweetener that it is being used to replace. The product would be mixed and then formed, for example by being sheeted, rotary cut, wire cut, or through another forming process. The products would then be baked under typical baking conditions, for example at 200-450° F.

The resistant corn syrup/solids can also be used to form sugar glasses in the amorphous state, to adhere particles to baked goods, and/or used to form a film or coating which enhances the appearance of a baked good. Resistant corn syrup solids, like other amorphous sugars, form glasses with heating and subsequent cooling to a temperature below their glass transition temperature.

Another type of food product in which the syrup can be used is breakfast cereal. For example, resistant corn syrup in accordance with the present invention could be used to replace all or part of the sugar in extruded cereal pieces and/or in the coating on the outside of those pieces. The coating is typically 30-60% of the total weight of the finished cereal piece. The syrup can be applied in a spray or drizzled on, for example. The formula for the coating can be as simple as a 75% solution of resistant corn syrup. The resistant corn syrup could also be blended with sugar at various percentages, or with other sweeteners or polyols. The extra moisture could then be evaporated in a low heat oven. In an extruded piece, the resistant corn syrup solids could be added directly with the dry ingredients, or the syrup form could be metered into the extruder with water or separately. A small amount of water could be added in the extruder, and then it could pass through various zones ranging from 100° F. to 300° F. Optionally, other sources of fiber such as resistant starch can be used in the extruded piece. Using the resistant corn syrup would create a different texture than other fiber sources. Using it alone or in combination with other fibers may alter the texture to create product diversity.

Another type of food product in which the syrup can be used is dairy products. Examples of dairy products in which it can be used include yogurt, yogurt drinks, milk drinks, flavored milks, smoothies, ice cream, shakes, cottage cheese, cottage cheese dressing, and dairy desserts, such as quarg and the whipped mousse-type products. This would include dairy products that are intended to be consumed directly (e.g., packaged smoothies) as well as those that are intended to be blended with other ingredients (e.g., blended smoothie). It can be used in pasteurized dairy products, such as ones that are pasteurized at a temperature from 160° F. to 285° F. Complete replacement of sugars in a dairy product is possible (which would be up to 24% of the total formula). The resistant corn syrup is generally stable at acid pH's (the pH range of dairy beverages typically would be 2-8).

Another type of food product in which the syrup can be used is confections. Examples of confections in which it can be used include hard candies, fondants, nougats and marshmallows, gelatin jelly candies or gummies, jellies, chocolate, licorice, chewing gum, caramels and toffees, chews, mints, tableted confections, and fruit snacks. In fruit snacks, the resistant corn syrup could be used in combination with fruit juice. The fruit juice would provide the majority of the sweetness, and the resistant corn syrup would reduce the total sugar content and add fiber. The syrup can be added to the initial candy slurry and heated to the finished solids content. The slurry could be heated from 200-305° F. to achieve the finished solids content. Acid could be added before or after heating to give a finished pH of 2-7. The resistant corn syrup could be used as a replacement for 0-100% of the sugar and 1-100% of the corn syrup or other sweeteners present.

Another type of food product in which the syrup can be used is jams and jellies. Jams and jellies are made from fruit. A jam contains fruit pieces, while jelly is made from fruit juice. The resistant corn syrup can be used in place of sugar or other sweeteners as follows: Weigh fruit and juice into a tank. Premix sugar, resistant corn syrup and pectin. Add the dry composition to the liquid and cook to a temperature of 214-220° F. Hot fill into jars and retort for 5-30 minutes.

Another type of food product in which the syrup can be used is beverages. Examples of beverages in which it can be used include carbonated beverages, fruit juices, concentrated juice mixes (e.g., margarita mix), clear waters, and beverage dry mixes. The use of the resistant corn syrup of the present invention would in many cases overcome the clarity problems that result when other types of fiber are added to beverages. A complete replacement of sugars is possible (which could be, for example, up to 12% of the total formula). Because of the stability of the syrup at acid pHs, it could be used in beverages having pH ranging from 2-7, for example. The resistant corn syrup could be used in cold processed beverages and in pasteurized beverages.

Another type of food product in which the syrup can be used is high solids fillings. Examples of high solids fillings in which it can be used include fillings in snack bars, toaster pastries, donuts, and cookies. The high solids filling could be an acid/fruit filling or a savory filling, for example. It could be added to products that would be consumed as is, or products that would undergo further processing, by a food processor (additional baking) or by a consumer (bake stable filling). In some embodiments of the invention, the high solids fillings would have a solids concentration between 67-90%. The solids could be entirely replaced with resistant corn syrup, or it could be used for a partial replacement of the other sweetener solids present (e.g., replacement of current solids from 5-100%). Typically fruit fillings would have a pH of 2-6, while savory fillings would be between 4-8 pH. Fillings could be prepared cold, or heated at up to 250° F. to evaporate to the desired finished solids content.

Another type of food product in which the syrup can be used is extruded and sheeted snacks. Examples of extruded and sheeted snacks in which it can be used include puffed snacks, crackers, tortilla chips, and corn chips. In preparing an extruded piece, the resistant corn syrup/solids would be added directly with the dry products. A small amount of water would be added in the extruder, and then it would pass through various zones ranging from 100° F. to 300° F. This dry resistant corn syrup/solids could be added at levels from 0-50% of the dry products mixture. The liquid resistant corn syrup could also be added at one of the liquid ports along the extruder. The product would come out at either a low moisture content (5%) and then baked to remove the excess moisture, or at a slightly higher moisture content (10%) and then fried to remove moisture and cook out the product. Baking could be at temperatures up to 500° F. for 20 minutes. Baking would more typically be at 350° F. for 10 minutes. Frying would typically be at 350° F. for 2-5 minutes. In a sheeted snack, the resistant corn syrup solids could be used as a partial replacement of the other dry ingredients (e.g., flour). It could be from 0-50% of the dry weight. The product would be dry mixed, and then water added to form cohesive dough. The product mix could have a pH from 5 to 8. The dough would then be sheeted and cut and then baked or fried. Baking could be at temperatures up to 500° F. for 20 minutes. Frying would typically be at 350° F. for 2-5 minutes. Another potential benefit from the use of the resistant corn syrup is a reduction of the fat content of fried snacks by as much as 15% when it is added as an internal ingredient or as a coating on the outside of a fried food.

Another type of food product in which the syrup can be used is gelatin desserts. The ingredients for gelatin desserts are often sold as a dry mix with gelatin as a gelling agent. The sugar solids could be replaced partially or entirely with resistant corn syrup solids in the dry mix. The dry mix can then be mixed with water and heated to 212° F. to dissolve the gelatin and then more water and/or fruit can be added to complete the gelatin dessert. The gelatin is then allowed to cool and set. Gelatin can also be sold in shelf stable packs. In that case the stabilizer is usually carrageenan-based. As stated above, resistant corn syrup can replace up to 100% of the other sweetener solids. The dry ingredients are mixed into the liquids and then pasteurized and put into cups and allowed to cool and set. The cups usually have a foil top.

Another type of food product in which the syrup can be used is snack bars. Examples of snack bars in which it can be used include breakfast and meal replacement bars, nutrition bars, granola bars, protein bars, and cereal bars. It could be used in any part of the snack bars, such as in the high solids filling, the binding syrup or the particulate portion. A complete or partial replacement of sugar in the binding syrup is possible with the resistant corn syrup. The binding syrup is typically from 50-90% solids and applied at a ratio ranging from 10% binding syrup to 90% particulates, to 70% binding syrup to 30% particulates. The binding syrup is made by heating a solution of sweeteners, bulking agents and other binders (like starch) to 160-230° F. (depending on the finished solids needed in the syrup). The syrup is then mixed with the particulates to coat the particulates, providing a coating throughout the matrix. The resistant corn syrup could also be used in the particulates themselves. This could be an extruded piece, directly expanded or gun puffed. It could be used in combination with another grain ingredient, corn meal, rice flour or other similar ingredient.

Another type of food product in which the syrup can be used is cheese, cheese sauces, and other cheese products. Examples of cheese, cheese sauces, and other cheese products in which it can be used include lower milk solids cheese, lower fat cheese, and calorie reduced cheese. In block cheese, it can help to improve the melting characteristics, or to decrease the effect of the melt limitation added by other ingredients such as starch. It could also be used in cheese sauces, for example as a bulking agent, to replace fat, milk solids, or other typical bulking agents.

Another type of food product in which the syrup/solids can be used is films that are edible and/or water soluble. Examples of films in which it can be used include films that are used to enclose dry mixes for a variety of foods and beverages that are intended to be dissolved in water, or films that are used to deliver color or flavors such as a spice film that is added to a food after cooking while still hot. Other film applications include, but are not limited to, fruit and vegetable leathers, and other flexible films.

Another type of food product in which the syrup can be used is soups, syrups, sauces, and dressings. A typical dressing could be from 0-50% oil, with a pH range of 2-7. It could be cold processed or heat processed. It would be mixed, and then stabilizer would be added. The resistant corn syrup could easily be added in liquid or dry form with the other ingredients as needed. The dressing composition may need to be heated to activate the stabilizer. Typical heating conditions would be from 170-200° F. for 1-30 minutes. After cooling, the oil is added to make a pre-emulsion. The product is then emulsified using a homogenizer, colloid mill, or other high shear process.

Sauces can have from 0-10% oil and from 10-50% total solids, and can have a pH from 2-8. Sauces can be cold processed or heat processed. The ingredients are mixed and then heat processed. The resistant corn syrup could easily be added in liquid or dry form with the other ingredients as needed. Typical heating would be from 170-200° F. for 1-30 minutes.

Soups are more typically 20-50% solids and in a more neutral pH range (4-8). They can be a dry mix, to which the dry resistant corn syrup solids could be added, or a liquid soup which is canned and then retorted. In soups, resistant corn syrup could be used up to 50% solids, though a more typical usage would be to deliver 5 g of fiber/serving.

Syrups can incorporate the resistant corn syrup as up to a 100% replacement of the sugar solids. Typically that would be 12-20% of the syrup on an as-is basis. The resistant corn syrup would be added with the water and then pasteurized and hot filled to make the product safe and shelf stable (typically 185° F. for one minute pasteurization).

Another type of food product in which the syrup can be used is coffee creamers. Examples of coffee creamers in which it can be used include both liquid and dry creamers. A dry blended coffee creamer can be blended with commercial creamer powders of the following fat types: soybean, coconut, palm, sunflower, or canola oil, or butterfat. These fats can be non-hydrogenated or hydrogenated. The resistant corn syrup solids can be added as a fiber source, optionally together with fructo-oligosaccharides, polydextrose, inulin, maltodextrin, resistant starch, sucrose, and/or conventional corn syrup solids. The composition can also contain high intensity sweeteners, such as sucralose, acesulfame potassium, aspartame, or combinations thereof. These ingredients can be dry blended to produce the desired composition.

A spray dried creamer powder is a combination of fat, protein and carbohydrates, emulsifiers, emulsifying salts, sweeteners, and anti-caking agents. The fat source can be one or more of soybean, coconut, palm, sunflower, or canola oil, or butterfat. The protein can be sodium or calcium caseinates, milk proteins, whey proteins, wheat proteins, or soy proteins. The carbohydrate can be the resistant corn syrup alone or in combination with fructo-oligosaccharides, polydextrose, inulin, resistant starch, maltodextrin, sucrose, or corn syrup. The emulsifiers can be mono- and diglycerides, acetylated mono- and diglycerides, or propylene glycol monoesters. The salts can be trisodium citrate, monosodium phosphate, disodium phosphate, trisodium phosphate, tetrasodium pyrophosphate, monopotassium phosphate, and/or dipotassium phosphate. The composition can also contain high intensity sweeteners, such as sucralose, acesulfame potassium, aspartame, or combinations thereof. Suitable anti-caking agents include sodium silicoaluminates or silica dioxides. The products are combined in slurry, optionally homogenized, and spray dried in either a granular or agglomerated form.

Liquid coffee creamers are simply a homogenized and pasteurized emulsion of fat (either dairy fat or hydrogenated vegetable oil), some milk solids or caseinates, corn syrup, and vanilla or other flavors, as well as a stabilizing blend. The product is usually pasteurized via HTST (high temperature short time) at 185° F. for 30 seconds, or UHT (ultra-high temperature), at 285° F. for 4 seconds, and homogenized in a two stage homogenizer at 500-3000 psi first stage, and 200-1000 psi second stage. The coffee creamer is usually stabilized so that it does not break down when added to the coffee.

Another type of food product in which the syrup can be used is food coatings such as icings, frostings, and glazes. In icings and frostings, the resistant corn syrup can be used as a sweetener replacement (complete or partial) to lower caloric content and increase fiber content. Glazes are typically about 70-90% sugar, with most of the rest being water, and the resistant corn syrup can be used to entirely or partially replace the sugar. Frosting typically contains about 2-40% of a liquid/solid fat combination, about 20-75% sweetener solids, color, flavor, and water. The resistant corn syrup can be used to replace all or part of the sweetener solids, or as a bulking agent in lower fat systems.

Another type of food product in which the syrup can be used is pet food, such as dry or moist dog food. Pet foods are made in a variety of ways, such as extrusion, forming, and formulating as gravies. The resistant corn syrup could be used at levels of 0-50% in each of these types.

Another type of food product in which the syrup can be used is tortillas, which usually contain flour and/or corn meal, fat, water, salt, and fumaric acid. The resistant corn syrup could be used to replace flour or fat. The ingredients are mixed and then sheeted or stamped and cooked. This addition could be used to add fiber or extend the shelf life.

Another type of food product in which the syrup can be used is fish and meat. Conventional corn syrup is already used in some meats, so the resistant corn syrup can be used as a partial or complete substitute. For example, the resistant corn syrup could be added to brine before it is vacuum tumbled or injected into the meat. It could be added with salt and phosphates, and optionally with water binding ingredients such as starch, carrageenan, or soy proteins. This would be used to add fiber, a typical level would be 5 g/serving which would allow a claim of excellent source of fiber.

Another type of food product in which the syrup can be used is dried (infused) fruit. Many kinds of dried fruit are only stable and palatable if they are infused with sugar. The resistant corn syrup can be substituted for all or part of the sugar. For example, the resistant corn syrup could be added to the brine used to infuse the fruit before drying. Stabilizing agents such as sulfates can be used in this brine as well.

Another type of food product in which the syrup can be used is infant and toddler food. The resistant corn syrup could be used as a replacement or a supplement to one or more conventional ingredients for such food. Because of its mild flavor and clear color, it could be added to a variety of baby foods to reduce sugar and increase fiber content.

Another type of food product in which the syrup can be used is batters and breadings, such as the batters and breadings for meat. This could be done by replacing all or part of the dry components of the batter and/or breading (e.g., flour type ingredients) with the resistant corn syrup, or to use in combination with addition to the meat muscle or fried food itself. This could be used as a bulking agent, for fiber addition, or to reduce fat in the fried food.

The process described herein takes advantage of a fraction of the saccharide syrup (e.g., stream 26 in FIG. 1) that is resistant to saccharification. By separating this material as a purified product, it can be employed for its own useful properties, rather than being an undesirable by-product in syrups that are primarily monosaccharides, such as high fructose corn syrup. Removal of a greater percentage of the oligosaccharides from the high fructose corn syrup allows that product to be made purer (i.e., with a higher concentration of dextrose and fructose) and thus more valuable.

Food products of the present invention can also be used to help control the blood glucose concentration in mammals, such as humans, that suffer from diabetes. When the food product is consumed by the mammal, the slowly digestible and/or digestion resistant components in the food product can cause a more moderate relative glycemic response in the bloodstream, which can be beneficial for diabetes patients. "Control" in this context should be understood as a relative term; i.e., the glycemic response can be improved relative to that occurring when the same mammal consumes a similar food product that does not contain such digestion-resistant and/or slowly digestible components, although the glycemic response may not necessarily be equivalent to what would be observed in a mammal that does not suffer from diabetes.

Certain embodiments of the invention can be further understood from the following examples.

Example 1

Raffinate syrup was obtained from a plant in which corn starch was being processed into high fructose corn syrup. The raffinate was produced by a chromatographic separation, and comprised primarily fructose and dextrose. The raffinate was subjected to nanofiltration using a Desal DK1812C-31D nanofiltration cartridge at about 500 psi of pressure and at a temperature of 40-60° C. The retentate from the nanofiltration was decolorized with activated charcoal, and then evaporated to approximately 80% dry solids. A saccharide analysis of the dry product was performed by HPAE-PAD chromatography, and the results are shown in Table 1.

TABLE 1

| Component | Wt % d.s.b. |
|---|---|
| dextrose | 38.9% |
| fructose | 6.1% |
| isomaltose | 14.3% |
| maltose | 10.5% |
| maltotriose | 0.3% |
| panose | 9.5% |
| linear higher saccharides | 0.0% |
| nonlinear higher saccharides | 20.4% |

This material, termed Light Raffinate, was tested for digestibility using an Englyst assay. About 600 mg of carbohydrate d.s.b. was added to 20 mL of 0.1 M sodium acetate buffer in a test tube. The contents were mixed and then heated to about 92° C. for 30 minutes, then cooled to 37° C. Then 5 mL of enzyme solution was added to the test tube and it was agitated by shaking in a water bath at 37° C. Small samples were removed at both 20 min and 120 min. The enzyme was inactivated, the samples were filtered and measured for digestibility using a glucose test from YSI Inc. A Heavy Raffinate, processed in a separate but similar nanofiltration operation, was also tested using the same assay. The Heavy Raffinate contained 25-35% dry solids, as opposed to 15-25% dry solids for the Light Raffinate, but both had approximately the same percentage of low molecular weight saccharides. A cooked potato starch, which had not been nanofiltered, was also tested as a comparison. The results of the digestibility assay and a saccharide analysis are shown in Table 2. Cooked potato starch is included in Table 2 for comparison. All percentages in Table 2 are on a d.s.b.

TABLE 2

| material | % rapidly digestible | % slowly digestible | % resistant | % monosaccharides (by HPAE) | % oligosaccharides (by HPAE) |
|---|---|---|---|---|---|
| Light raffinate | 45 | 3 | 52 | 45 | 55 |
| Heavy raffinate | 41 | 3 | 56 | 44 | 56 |
| Potato starch (cooked) | 78 | 11 | 11 | 44 | 56 |

There was an excellent correlation between the percentage of oligosaccharides in the material and the percentage of the material that was resistant to digestion.

Example 2

About 1,025 L of raffinate syrup at 21.4% dry solids was obtained from a plant in which corn starch was being processed into high fructose corn syrup. The raffinate was produced by a chromatographic separation, and comprised primarily fructose and dextrose. The raffinate was subjected to nanofiltration using two Desal NF3840C-50D nanofiltration cartridges at about 500 psi of pressure and at a temperature of 40-60° C. After the starting volume was reduced by about a factor of 20, the retentate was subjected to about 2 volumes of constant volume diafiltration using DI water. After diafiltration, 27.6 kg of retentate product (at 33.8% ds) was collected. This material was decolorized with activated carbon (0.5% by weight of syrup solids) by stirring in a refrigerator overnight. This slurry was sterilized by filtration through a 0.45 micron hollow fiber filtration cartridge, and evaporated in parts to an average concentration of about 73% ds.

A saccharide analysis of the dry product was performed by HPAE-PAD chromatography, and the results are shown in Table 3.

TABLE 3

| Component | Wt % d.s.b. |
|---|---|
| dextrose | 4.5% |
| fructose | 0.9% |
| isomaltose | 20.6% |
| maltose | 23.5% |
| maltotriose | 0.4% |
| panose | 20.9% |
| linear higher saccharides | 0.0% |
| nonlinear higher saccharides | 29.1% |

Example 3

Preparation of Non-Linear Oligomers from Dextrose by Enzyme

Concentrated dextrose syrups having solids concentrations of 74%, 79.5%, and 80% were prepared by (1) evaporating diluted syrup or (2) adding water to dextrose powder. Each dextrose/water mixture was placed in a suitable container and heated to 60° C. in a water bath.

Glucoamylase enzyme (Dextrozyme or Spirizyme, from Novozymes A/S) was added to the syrup—approximately 400 µl enzyme to 30 ml syrup. The syrup container was capped, and then shaken vigorously to distribute the enzyme. The syrup was returned to the 60° C. water bath.

The change in sugar distribution was monitored over time by transferring 2-4 ml syrup to a small glass vial, and heating it in a heated block to approximately 85-90° C. to deactivate the enzyme.

The concentration of various sugar species was determined by High Performance Anion Exchange with Pulsed Amperometric Detection, (HPAE-PAD). A Dionex ion chromatograph, DX500, equipped with electrochemical detector and gradient pump, was used for the analyses. The sugars were separated on Dionex Carbopac PA1 analytical and guard columns with gradient delivery of a sodium hydroxide and sodium acetate eluent. The sugars were detected using a gold electrode with a four-potential waveform. Samples were diluted with water and passed through Amicon Ultra-4 centrifugal filter devices before analysis.

Figure 2:
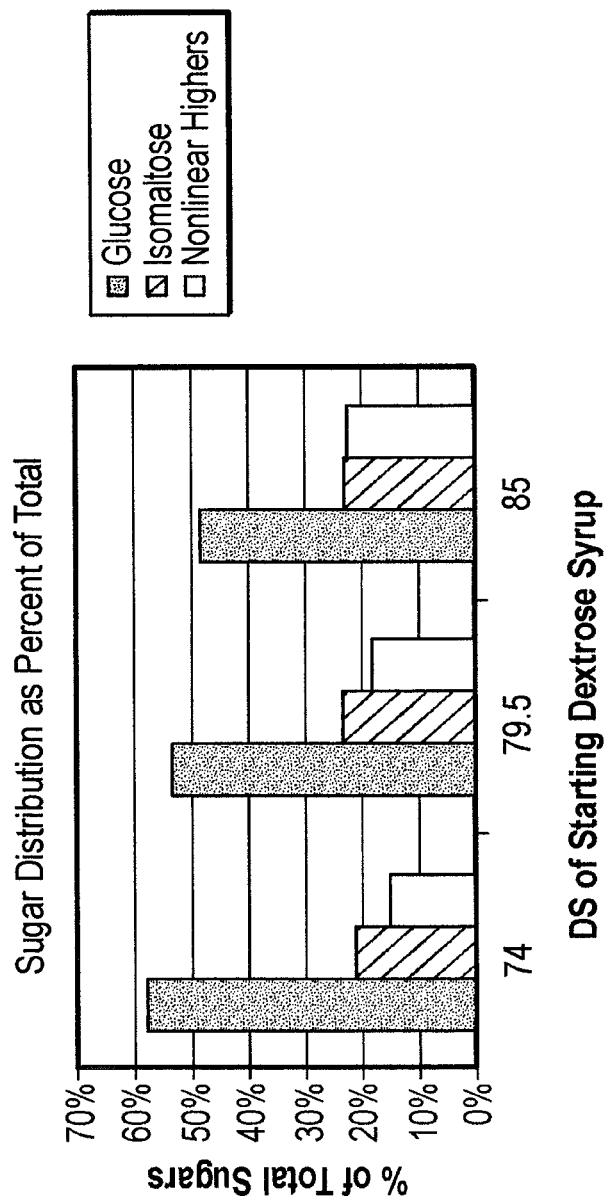
FIG. 2 is a graph of the distribution of certain saccharides in three dextrose compositions used in Example 3.

FIG. 2 illustrates the relative amounts of dextrose, isomaltose and "non-linear highers" (which in this figure refers to nonlinear oligomers having a degree of polymerization of four or more) in syrups of three different initial dextrose compositions treated with 1.3% vol/vol Dextrazyme, a commercial glucoamylase enzyme from Novozymes, for 48 hrs at 60° C. As syrup concentration increased, the amount of monomeric dextrose, relative to other sugars, decreased, and the amount of non-linear higher oligomers increases.

Example 4

Preparation of Oligomer Syrup from Corn Syrups

Starting substrates were obtained having a range of extents of conversion, from dextrose greens (95% dextrose) to lightly converted Staley 200 syrup (26 DE, 5% dextrose) and including high (34%) maltose syrup, Neto 7300. The specific products used as starting materials in this example were Staley® 200, Staley® 300, Staley® 1300, Neto® 7300, and Sweetose® 4300 corn syrups, and Staleydex® 3370 dextrose. Some of the characteristics of these materials are given in Table 4.

TABLE 4

Characteristics of starting syrups

|  | Staley 200 | Staley 300 | Staley 1300 | Neto 7300 | Sweetose 4300 | Staleydex 3370 |
|---|---|---|---|---|---|---|
| Degree of conversion | very low | low | regular | regular | high | high |
| Type of conversion | acid-enzyme | acid | acid | acid-enzyme | acid-enzyme | acid-enzyme |
| Dextrose equivalent (D.E.) % | 26 | 35 | 43 | 42 | 63 | 95 |
| % dextrose | 5 | 13 | 19 | 9 | 37 | 90 |
| % maltose | 8 | 10 | 14 | 34 | 29 | 4 |
| % maltotriose | 11 | 11 | 13 | 24 | 9 | 2 |
| % higher saccharides | 76 | 66 | 54 | 33 | 25 | — |

Figure 3:
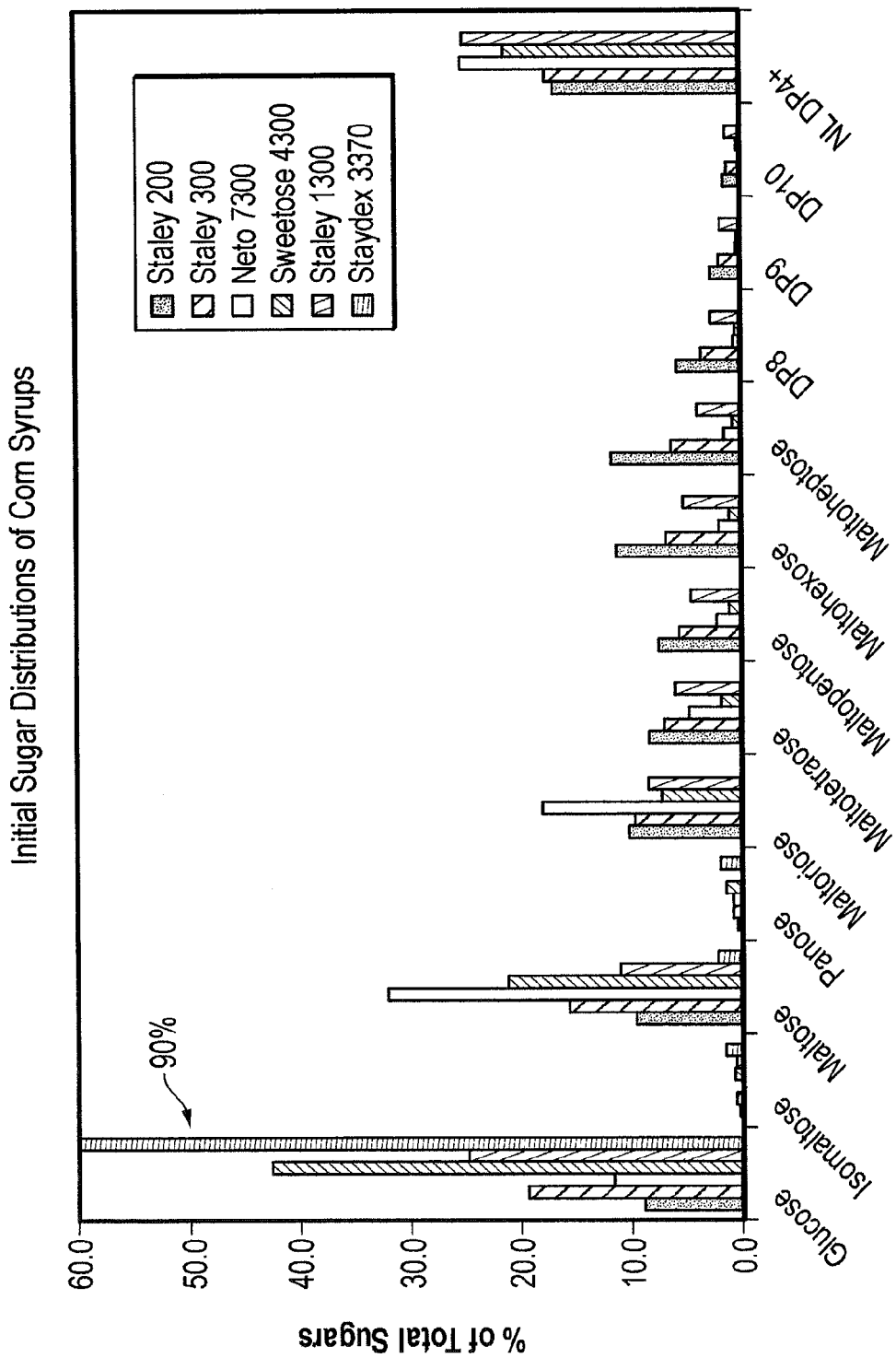
FIG. 3 is a graph of the distribution of certain saccharides in the starting materials used in Example 4.

While many of the less-converted syrups have substantial quantities of nonlinear higher oligomers having a degree of polymerization of four or more (NL DP 4+), they also have substantial quantities of linear oligomers. Several of these syrups contain measurable linear oligomers up through DP 17. FIG. 3 shows the initial saccharide distributions.

The enzymes used were Spirizyme Plus FG and Dextrozyme DX 1.5X glucoamylases and Promozyme D2 pullulanase (supplied by Novozymes), CG 220 Cellulase and Transglucosidase L-500 (supplied by Genencor), Glucoamylase GA150 (supplied by Sunson Industry Group), and Transglucosidase L (supplied by Bio-Cat Inc.).

Figure 4:
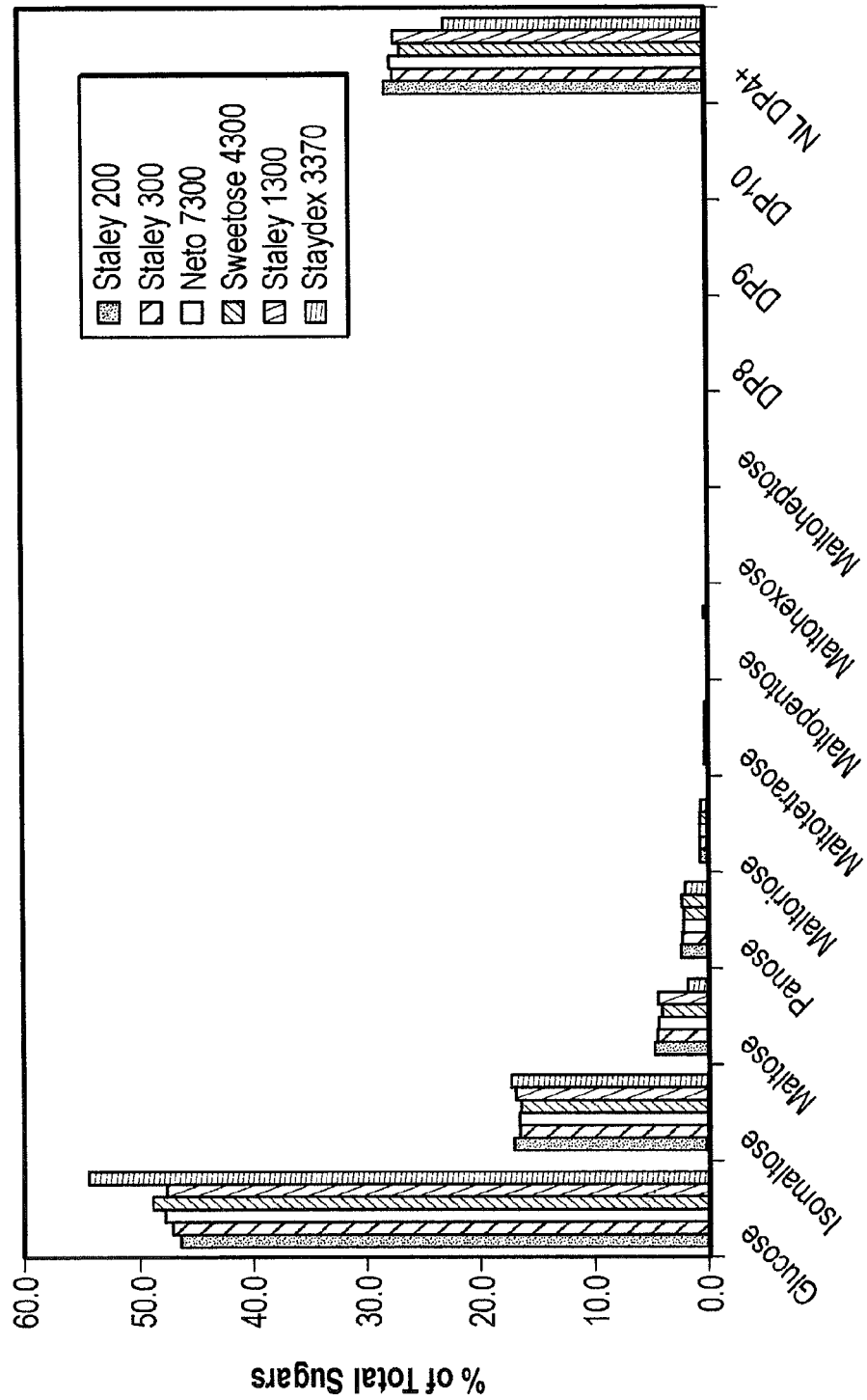
FIG. 4 is a graph of the distribution of certain saccharides in the products prepared by enzyme treatment in Example 4.

The various corn syrups were adjusted to approximately 70% ds. Approximately 3.3% (v/v) Spirizyme Plus FG Enzyme was added to each in 50 ml tubes. The syrups were heated in 60° C. water baths for approximately 4 days. The enzyme was deactivated by heating the syrups to approximately 85° C. for 10 min. FIG. 4 shows the final saccharide distributions. All the syrups reached a comparable sugar distribution by the end of the four day treatment. After reversion, very little linear oligomers remained, and non-linear oligomer content had increased.

Several points should be noted. First, the reverted Staleydex 3370 syrup has a somewhat higher dextrose content and lower content of non-linear oligomers than the other syrups. While all syrups were adjusted to approximately 70% ds before reversion, the less converted syrups, with low initial dextrose content, consumed water as the new distribution was established, and final concentrations were 4-9 percentage points higher than the reverted 3370 syrup. (The hydrolysis of a single DP6 oligomer of dextrose to six dextrose molecules, for example, consumes five water molecules.) As Table 5 shows, the water contents of the reverted syrups trend with the dextrose content, and trend inversely with the higher oligomer content.

TABLE 5

| Starting Syrup | Concentrations After Reversion, % | | |
|---|---|---|---|
|  | Water | Dextrose | NL DP4+ |
| Staydex 3370 | 28 | 54 | 23 |
| Sweetose 4300 | 25 | 49 | 27 |
| Neto 7300 | 21 | 48 | 27 |
| Staley 1300 | 24 | 48 | 27 |
| Staley 300 | 19 | 47 | 27 |
| Staley 200 | 20 | 46 | 28 |

Lower water content drives the equilibrium toward a higher concentration of reversion products. If the water content had been adjusted so that final water contents had been identical, we believe the sugar distributions would also have been identical.

Second, all syrups after reversion had much higher percentages of branched oligomers at each degree of polymerization (DP) than linear oligomers. Compare the relative amount of maltose vs. isomaltose, panose vs. maltotriose, and NL DP4+ vs. linear oligomers of DP4 and greater (of which there is virtually none remaining after reversion).

Figure 5:
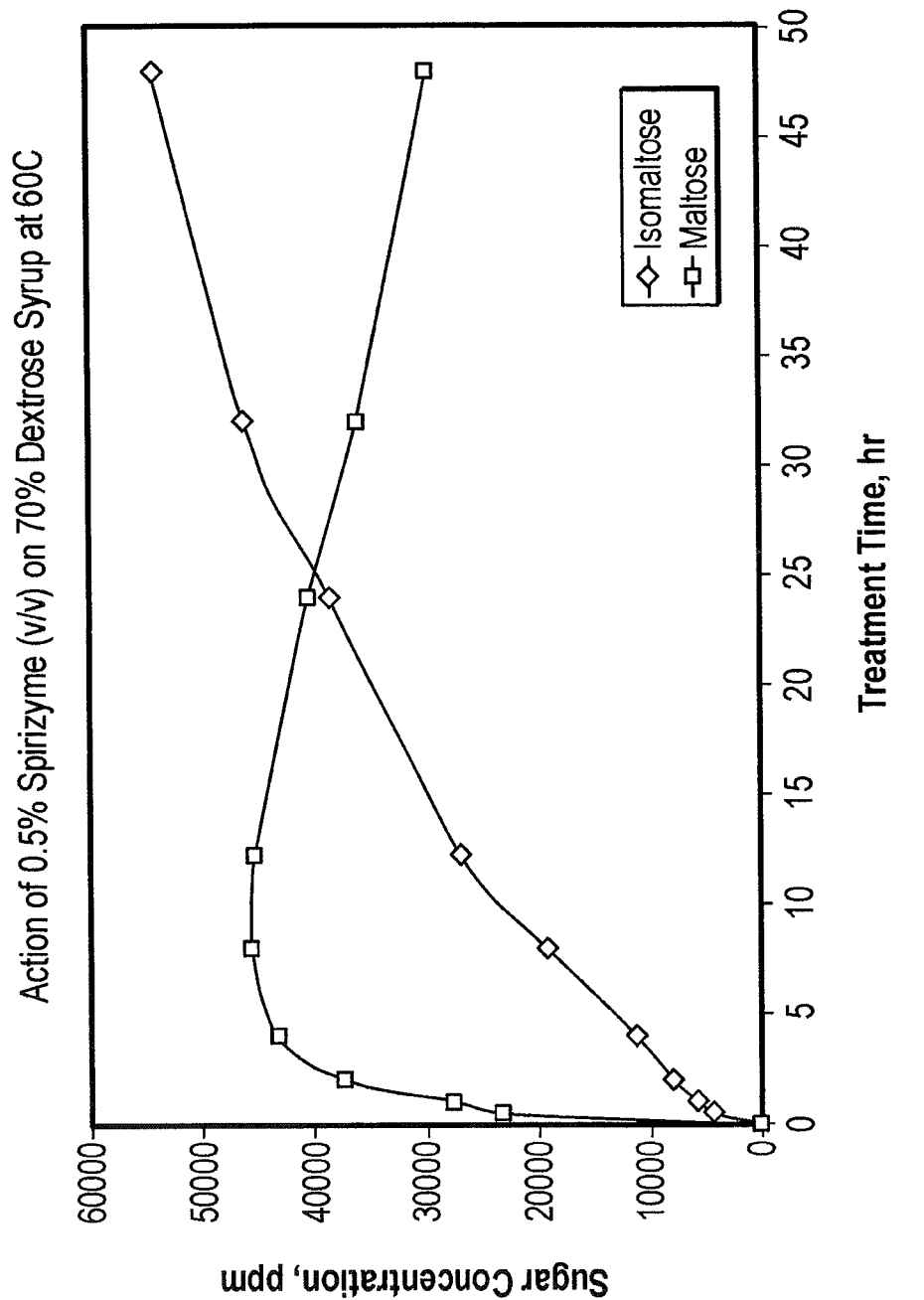
FIG. 5 is a graph of the change over time in maltose and isomaltose concentrations when a composition was treated with enzyme in Example 4.

FIG. 5 shows the change in maltose and isomaltose concentrations over time when a concentrated dextrose syrup was treated with Spirizyme. It would appear that linear oligomers are the kinetic products while non-linear oligomers are the thermodynamic products. That is, forming the linear dimer, maltose, from dextrose is a rapid and reversible reaction with low activation energy. Forming the non-linear dimer, isomaltose, is a slower reaction, and its reverse reaction has a high activation energy.

Figure 6:
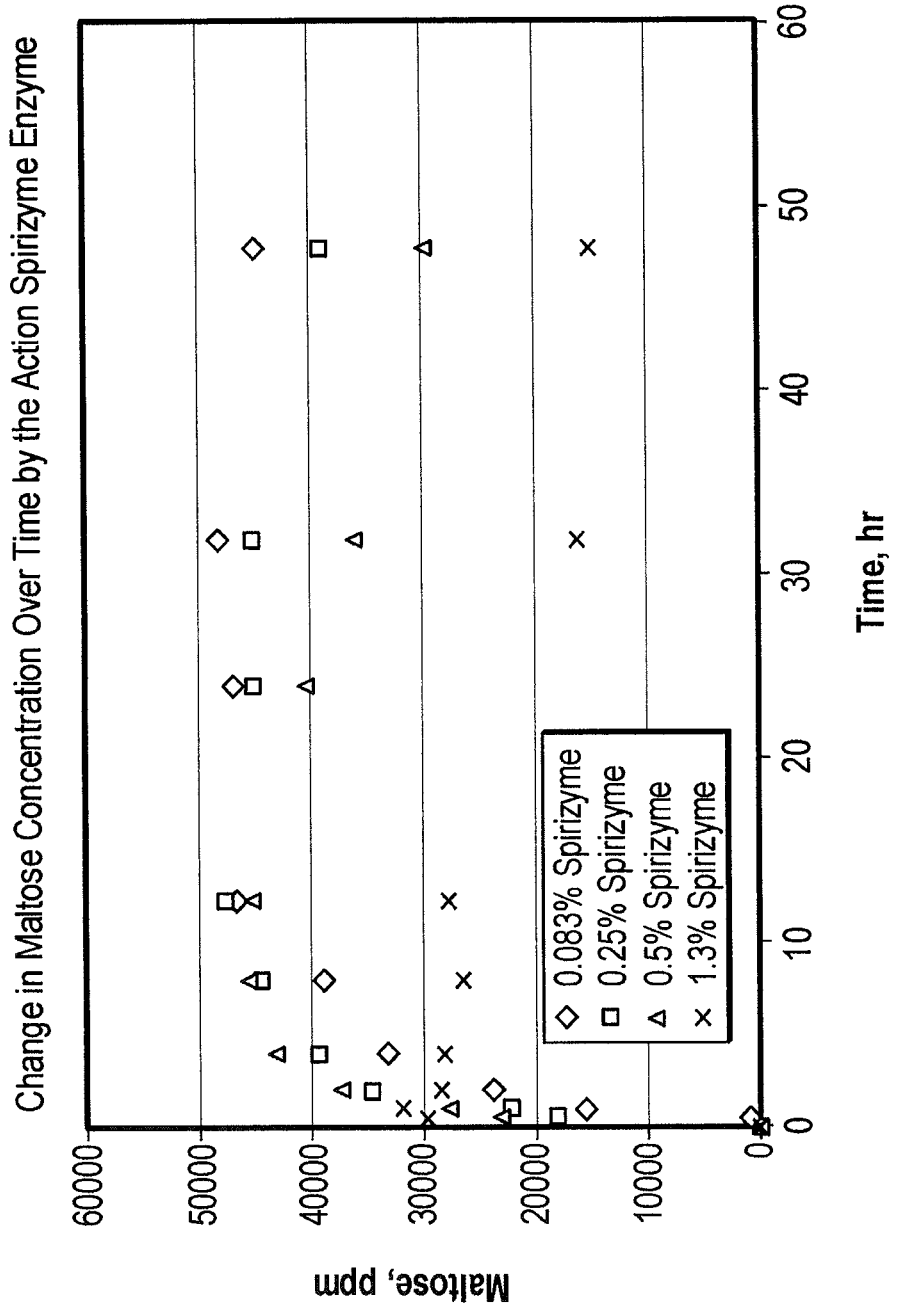
FIG. 6 is a graph of the change in maltose concentration and FIG. 7 is a graph of the change in isomaltose concentration when dextrose syrup was treated with different concentrations of enzyme in Example 4.
Figure 7:
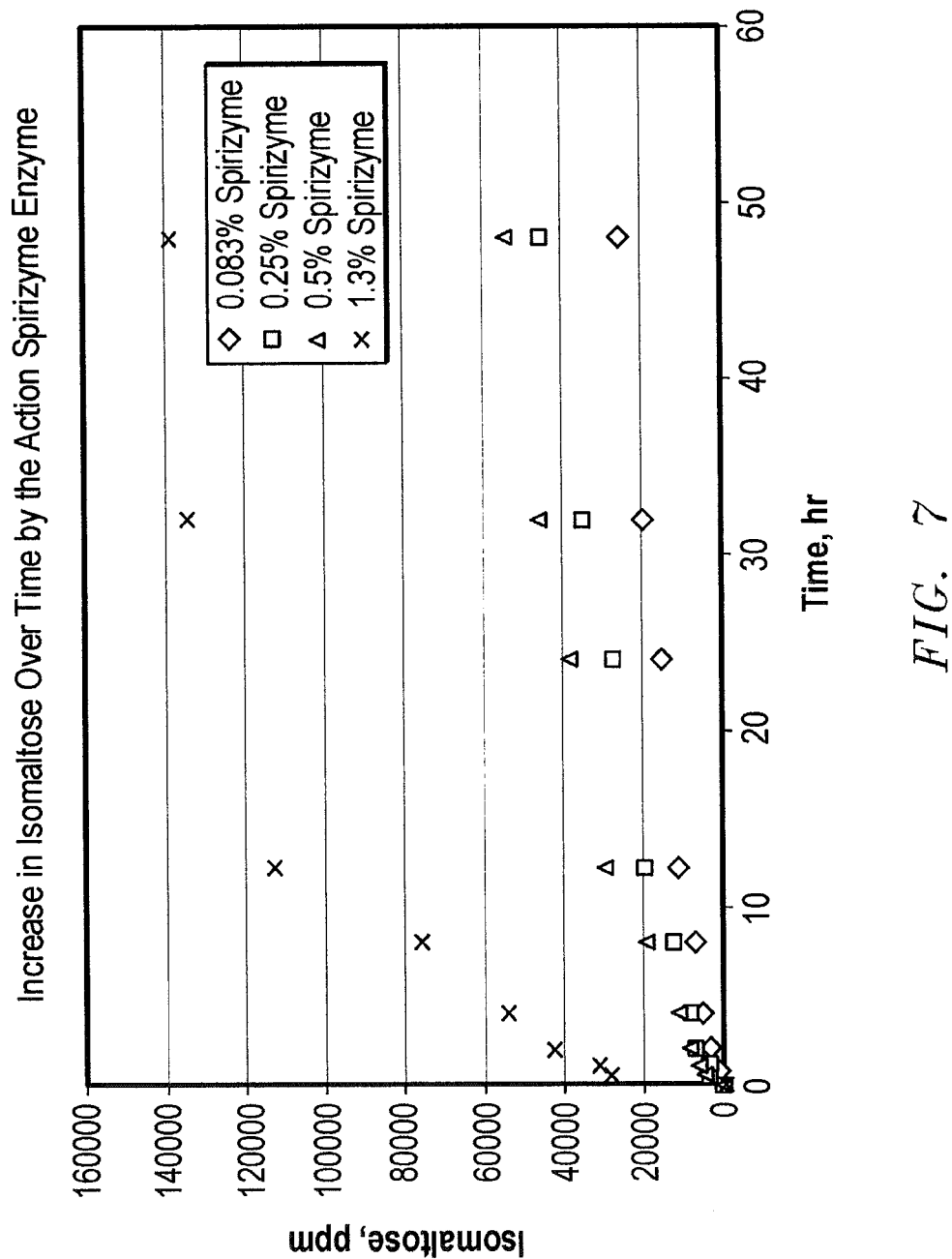

FIGS. 6 and 7 show the change in maltose and isomaltose concentrations over time when 70% dextrose syrup is treated with different concentrations of Spirizyme enzyme at 60° C.

Figure 8:
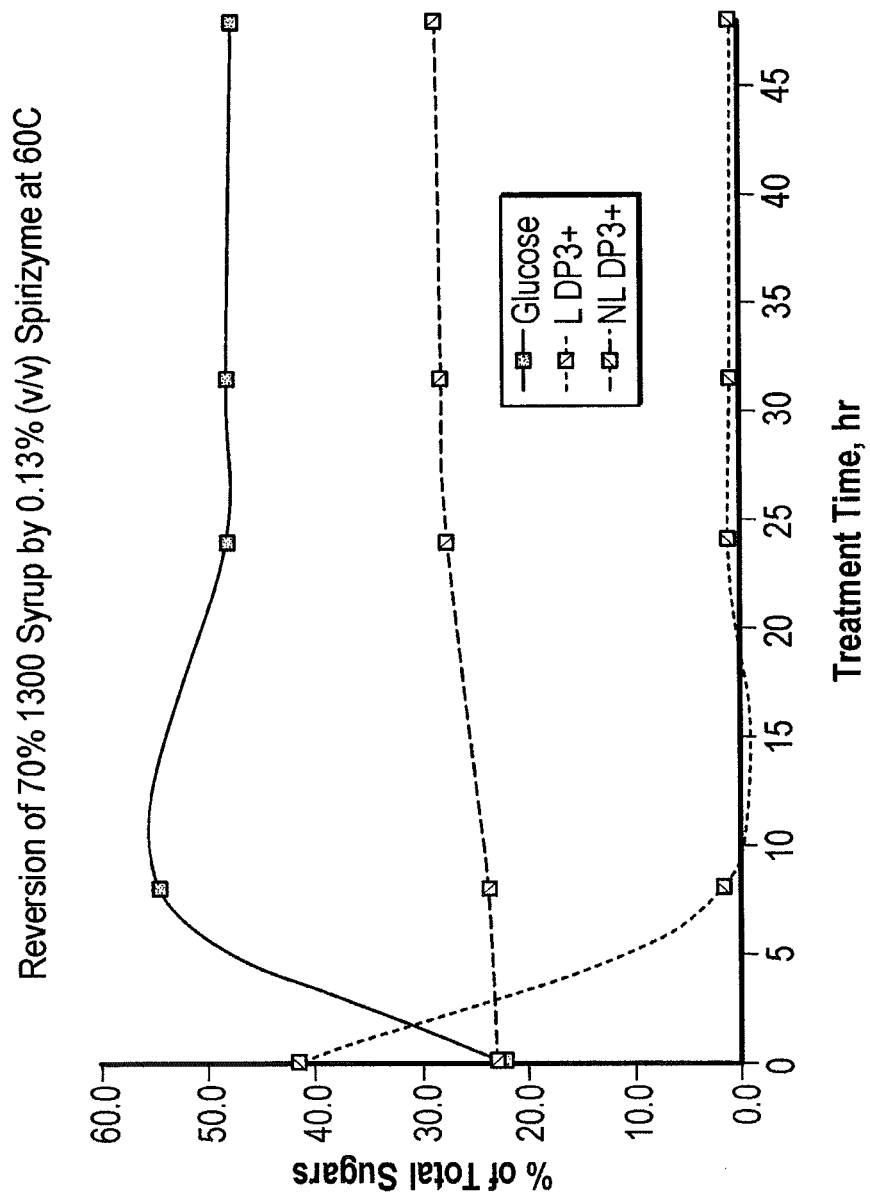
FIG. 8 is a graph of the change over time in the concentrations of certain saccharides when a composition was treated with enzyme in Example 4.

In the treatment of Staley 1300 syrup with glucoamylase, the linear oligomers of DP 3 and greater were rapidly consumed and converted to dextrose. The concentration of these linear oligomers reached its equilibrium of about 1% of total sugars (at 70% syrup concentration, 0.13% Spirizyme and 60° C.) within the first few hours of treatment. (See FIG. 8.) Over a longer period, dextrose concentration slowly decreased, and the concentration of non-linear oligomers slowly increased. The change in concentration of maltose and isomaltose over time mirrors that seen for dextrose reversion (FIG. 7).

Samples from the above experiments were heated above 85° C. for 10-20 minutes to deactivate the enzymes before diluting for ion chromatography analysis. Had the samples been diluted in the presence of active enzyme, they might have been hydrolyzed back to dextrose.

Samples of the reverted syrups were diluted to 20% solids. A portion of each was held in the presence of Spirizyme enzyme at 60° C. and another portion of each was held in the presence of Spirizyme at 40° C. The syrups were sampled over time, and the enzymes in each sample were deactivated as described above.

Figure 9:
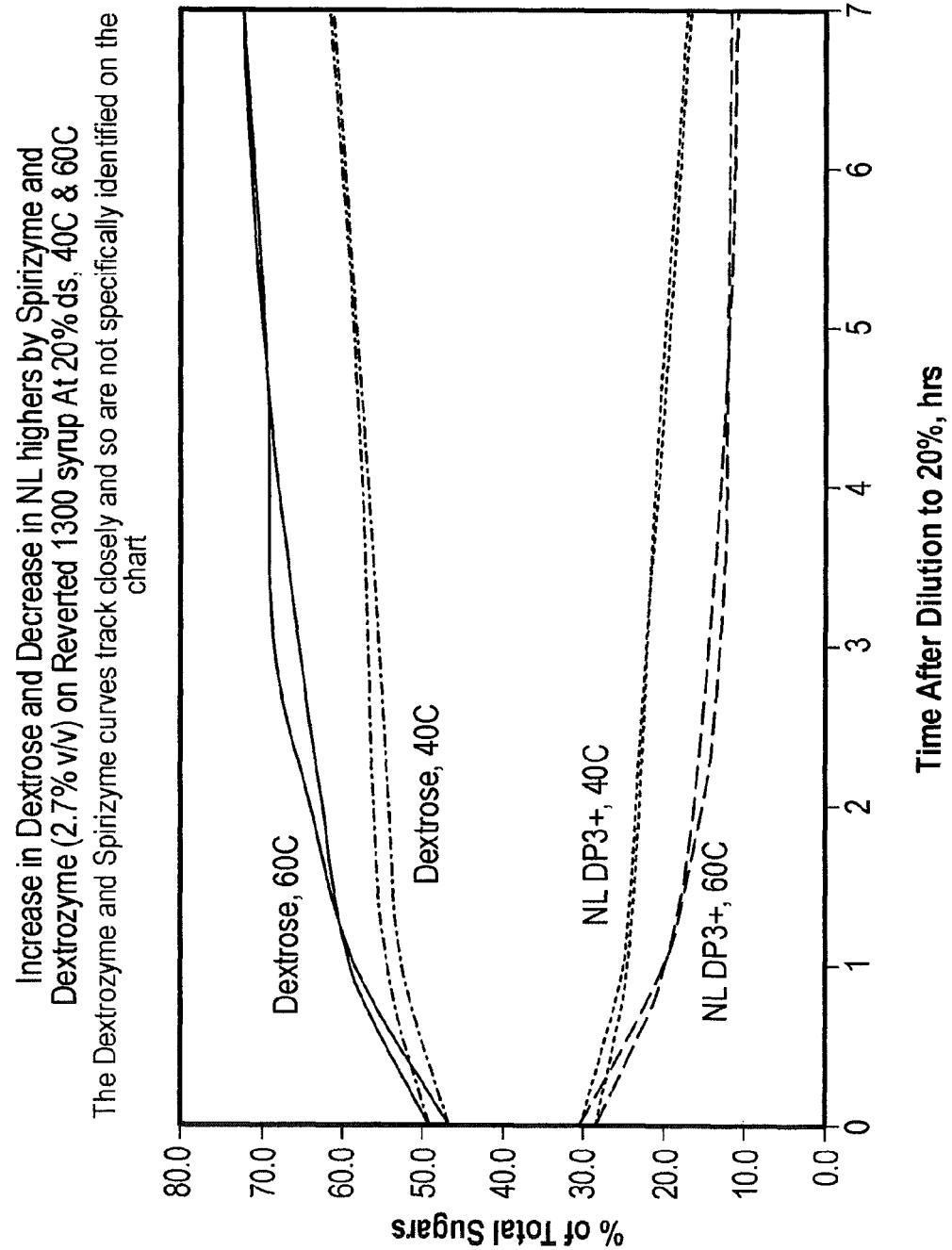
FIG. 9 is a graph of the change over time in the concentrations of certain saccharides when a diluted composition was treated with enzyme in Example 4.

FIG. 9 shows the results. At 60° C., the concentration of nonlinear higher oligomers (DP3 and greater) dropped to half within 3 hours and appeared to plateau at about 11.6% of total sugars by 7 hours. Lower temperature slowed hydrolysis. As FIG. 9 shows, dextrose content increased as a result of hydrolysis. The rate of hydrolysis when two different glucoamylases (Spirizyme and Dextrozyme) were used was identical.

It appears from these experiments that the non-linear oligomers formed through reversion are not immune to hydrolysis by glucoamylase enzymes (or impurities therein). However, it appears that a portion of them is resistant to hydrolysis. At 20% ds the equilibrium between monomer and oligomer is well on the side of monomer. Yet 11.3% DP4+ and 11.6% DP3+ remain after 7 hours at optimum temperature for glucoamylase activity. Compare this with the virtually complete conversion of linear oligomers to dextrose in the same time frame while at much higher solids (70% ds) and half the glucoamylase content, illustrated in FIG. 8. It would appear that, while glucoamylase enzymes can hydrolyze non-linear oligomers, the hydrolysis is not rapid, and may not go to complete conversion. We propose that the digestive enzymes in the human gut will have similarly reduced activity towards these compounds.

Table 6 shows the change in concentration of all sugar species when reverted syrup was diluted to 20% ds at 60° C. in the presence of active Spirizyme enzyme

TABLE 6

| hr time | % of total sugars | | | | | | | |
|---|---|---|---|---|---|---|---|---|
| | Glucose | Isomaltose | Maltose | Panose | Maltoriose | L DP3+ | NL DP3+ | NL DP4+ |
| 0 | 46.7 | 16.8 | 4.5 | 2.4 | 0.3 | 1.0 | 30.5 | 28.1 |
| 1 | 58.6 | 18.1 | 2.0 | 0.6 | 0.1 | 0.6 | 20.1 | 19.5 |
| 2 | 64.0 | 17.0 | 2.3 | 0.5 | 0.1 | 0.5 | 15.3 | 14.9 |
| 3 | 68.6 | 15.3 | 2.1 | 0.4 | 0.1 | 0.4 | 12.8 | 12.4 |
| 4.75 | 69.6 | 14.7 | 2.1 | 0.3 | 0.1 | 0.5 | 12.2 | 11.9 |
| 7 | 72.3 | 13.0 | 1.9 | 0.3 | 0.1 | 0.5 | 11.6 | 11.3 |

("L DP3+" refers to linear oligomers having a degree of polymerization of three or more.
"NL DP3+" refers to nonlinear oligomers having a degree of polymerization of three or more.
"NL DP4+" refers to nonlinear oligomers having a degree of polymerization of four or more.)

Regardless of starting sugar distribution or degree of conversion, all corn syrups tested were converted to a comparable sugar distribution by glucoamylase if treated at comparable syrup concentrations.

From these experiments, it appears that during the enzymatic reversion of corn syrup, linear oligomers are rapidly hydrolyzed to dextrose. Over longer times and at high syrup concentrations the dextrose is consumed as non-linear oligomers are formed. The production of non-linear oligomers is at least partially reversible, as evidenced by their hydrolysis by glucoamylase at lower syrup solids. Thus, when the reverted syrups are diluted before deactivating the glucoamylase, a portion of, but apparently not all of the oligomers are hydrolyzed back to dextrose monomer. This demonstrates that the formation of non-linear linkages by glucoamylase (or perhaps impurities it contains) is not entirely irreversible "mistakes" by the enzyme.

Example 5

Quality of Glucoamylases Impacts Reversion

The amount of enzyme needed to effect the reversion is high relative to typical enzymatic processes. Approximately 1.5% v/v of commonly used glucoamylases (for example, Spirizyme Plus FG and Dextrozyme DX 1.5X, supplied by Novozymes) are needed to reach 80% of equilibrium reversion in 24 hrs at 60-75° C. It should be noted that enzyme manufacturers have made great strides in reducing the tendency of the glucoamylase to form reversion products—improvements driven by the consumers of these enzymes—the manufacturers of corn syrup—for which reversion products are a bane. It is our belief that the enzymes from the 1950s would be much more efficient for forming these non-linear oligomer syrups than current glucoamylases.

Figure 10:
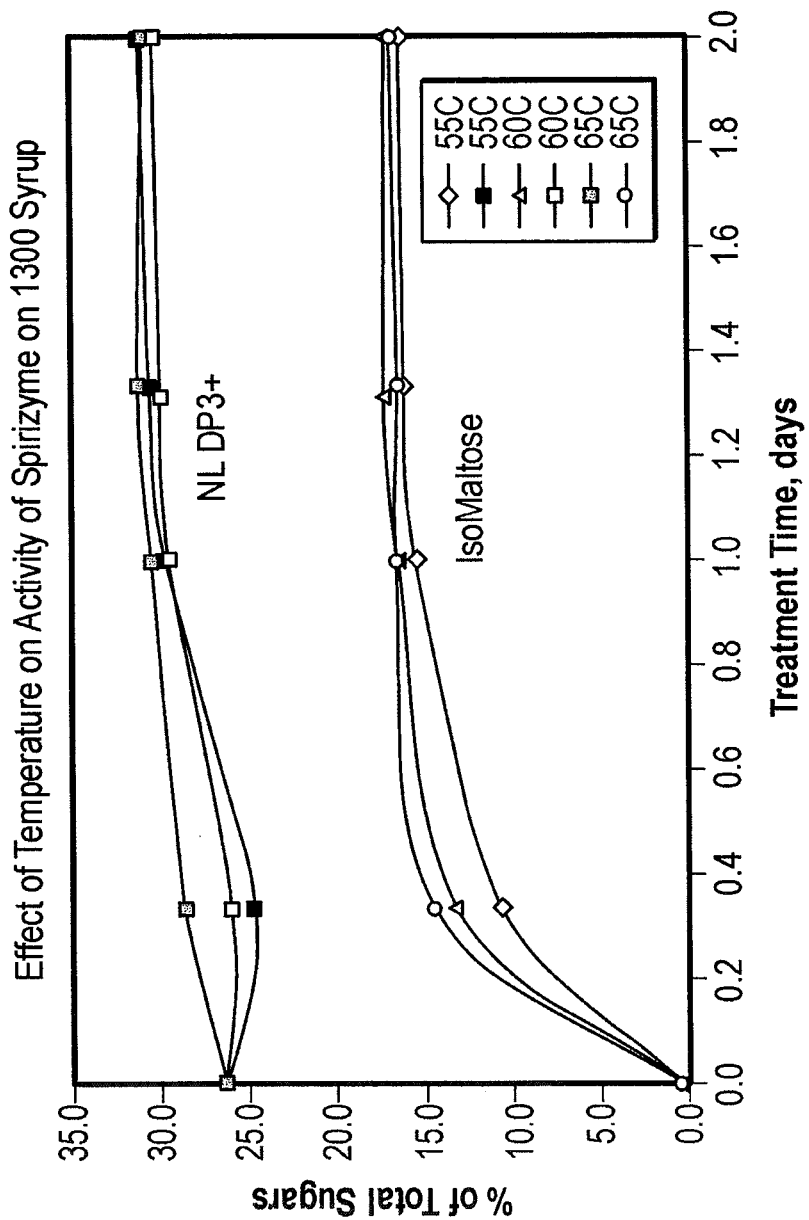
FIG. 10 is a graph of the effect of temperature on the formation of certain saccharides as a result of enzyme treatment in Example 5.
Figure 11:
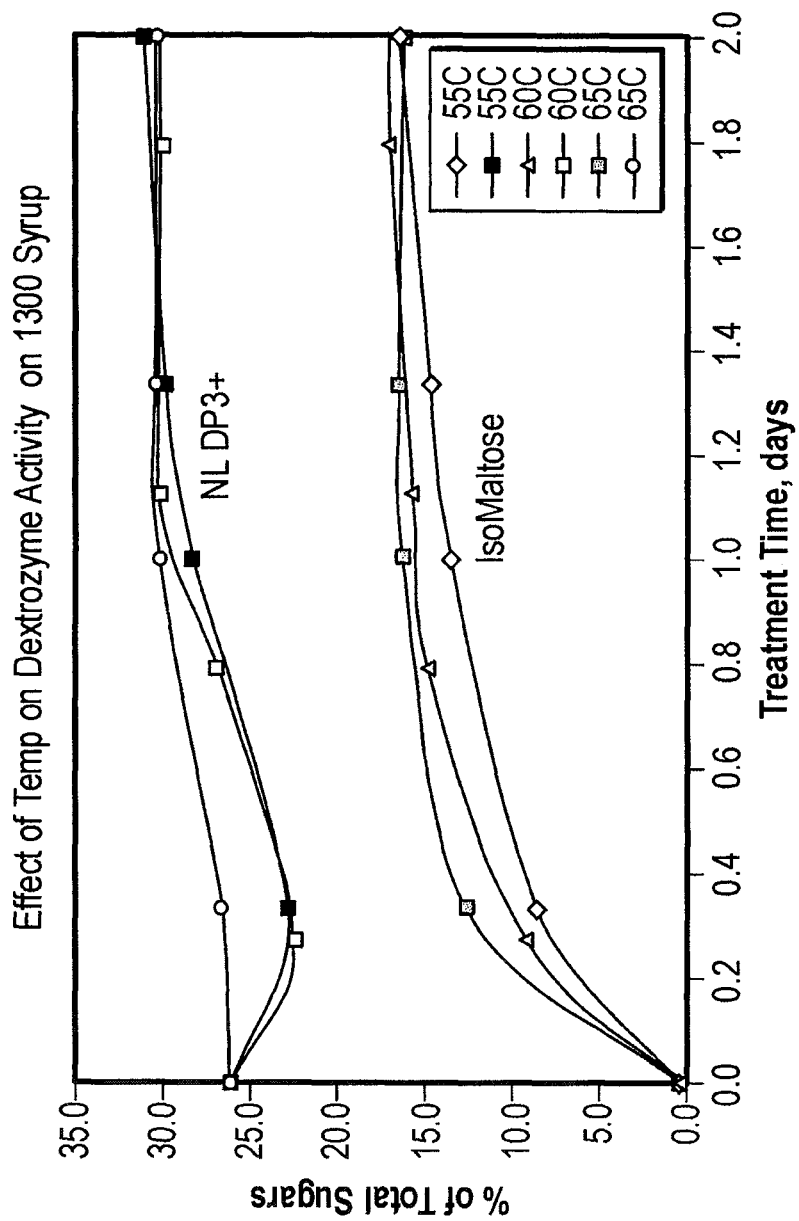
FIG. 11 is a graph of the effect of temperature on the formation of certain saccharides as a result of another enzyme treatment in Example 5.

Lending support to the concept that "impurities" still in these commercial glucoamylases may be responsible for the reversion products in the experiments reported here is the fact that, while Novozymes reports the optimum temperature for activity for both Spirizyme and Dextrozyme to be 59-61° C., the rate of generation of reversion products increases when temperature is increased from 60 to 65° C. FIGS. 10 and 11 show the rate of formation of isomaltose and non-linear oligomers of DP 3 and greater (NL DP3+), as a function of temperature, for Spirizyme and Dextrozyme. The substrate syrup was Staley 1300, and the amount of enzyme used was 2.7% v/v.

Example 6

Acid-Catalyzed Restructuring of Corn Syrup to Form Non-Linear Oligomers

Staley 1300 syrup was diluted 1:4 with deionized water to facilitate pH determinations. The amount of acid (HCl or $H_2SO_4$) to drop syrup pH to the pH target was determined. In one experiment, 10% Krystar crystalline fructose was added to the syrup prior to acid treatment.

Staley 1300 syrup was heated to approximately 60° C. in 50 ml screw-cap centrifuge tubes in a shaking water bath. The pre-determined amount of acid needed to reach target pH was added to the syrup. The syrup tubes were shaken vigorously to uniformly distribute the acid. The tubes were returned to the water bath, and bath temperature adjusted as needed. Treatments were performed at 60, 70, and 80° C., and at pHs of 1.2, 1.8 and 2.3. To monitor the progress of the reactions, portions of the syrup were removed from tubes and neutralized by adding a caustic solution.

The caustic solutions were prepared such that a volume of caustic solution was sufficient to neutralize an equal volume of acidified syrup. Approximately 80% of this volume was added all at once, which diluted the syrup sufficiently for pH measurement. Additional caustic solution was added dropwise until pH reached >5.0 (and preferably no greater than 6.5).

The syrup solutions were analyzed using ion chromatography. In addition to a RSO Oligosaccharide column from Phenomenex, some samples were also analyzed using a Dionex CarboPac PA200 column.

The first acid condensation reaction on Staley 1300 syrup was at pH 2.3 with sulfuric acid, at 60° C. The proportion of linear oligomers decreased, and non-linear oligomers increased.

Figure 12:
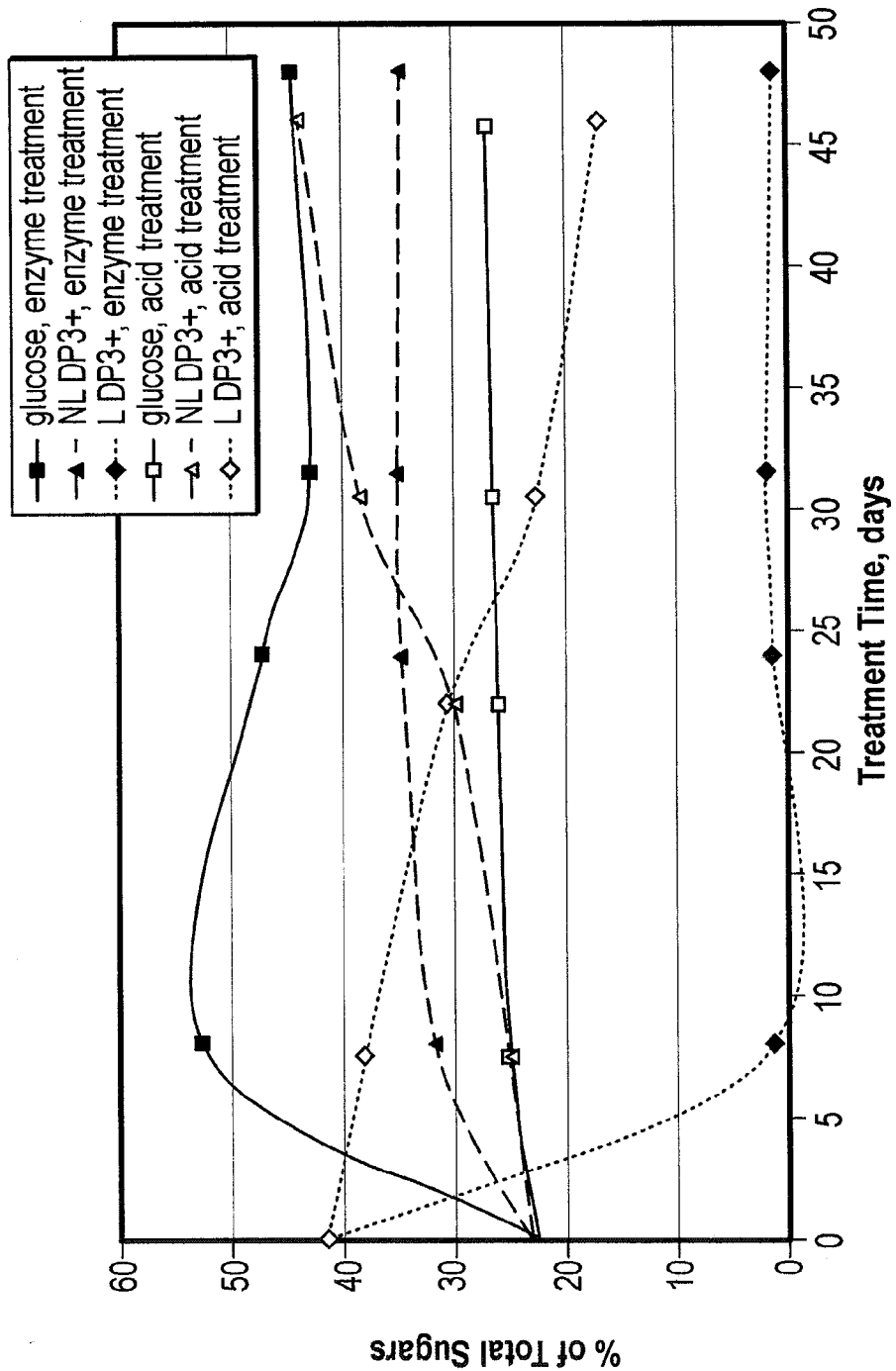
FIG. 12 is a graph comparing the changes in saccharide distribution when a composition was treated by acid or by enzyme in Example 6.

FIG. 12 compares the changes in sugar distributions in Staley 1300 syrup caused by acid treatment and glucoamylase treatment (both at 60° C.). It can be seen that the processes proceed differently. Spirizyme glucoamylase consumes linear oligomers very rapidly, generating dextrose. With Staley 1300 syrup, the concentration of linear oligomers of DP3 and greater drops from approximately 42% of total sugars to its equilibrium value of approximately 1% within hours of contact with the enzyme. Over a longer period, a portion of the dextrose is converted to non-linear oligomers. The concentration of non-linear DP3 and higher (DP3+) increases over about 30 hours (under the conditions of this enzyme treatment).

In contrast, on contact with acid, linear oligomers are consumed and non-linear oligomers formed at comparable rates. Dextrose concentration increases very slowly over the course of the treatment.

In a parallel experiment, 10% dry fructose was added to Staley 1300 syrup, so that the final syrup solids concentration was approximately 90%. It was treated to the same pH, temperature and time as the Staley 1300 syrup by itself. While the Staley 1300 syrup developed color over the course of the treatment, the fructose-containing syrup turned coffee-colored almost immediately. IC analysis of samples pulled from it showed the rate of linear oligomers reduction, and non-linear oligomers generation, comparable to the acid-treated syrup by itself. Fructose content was not significantly altered.

A second round of acid treatments was conducted in which Staley 1300 syrup was adjusted to 1.2 and 1.8 pH with HCl. Each pH treatment was run at temperatures of 70° C. and 80° C. All syrups generated significant color over the course of the treatments. The extent of color increased with decreasing pH, increasing temperature and increasing time. At the extreme, darkly-colored insoluble components formed.

Figure 13:
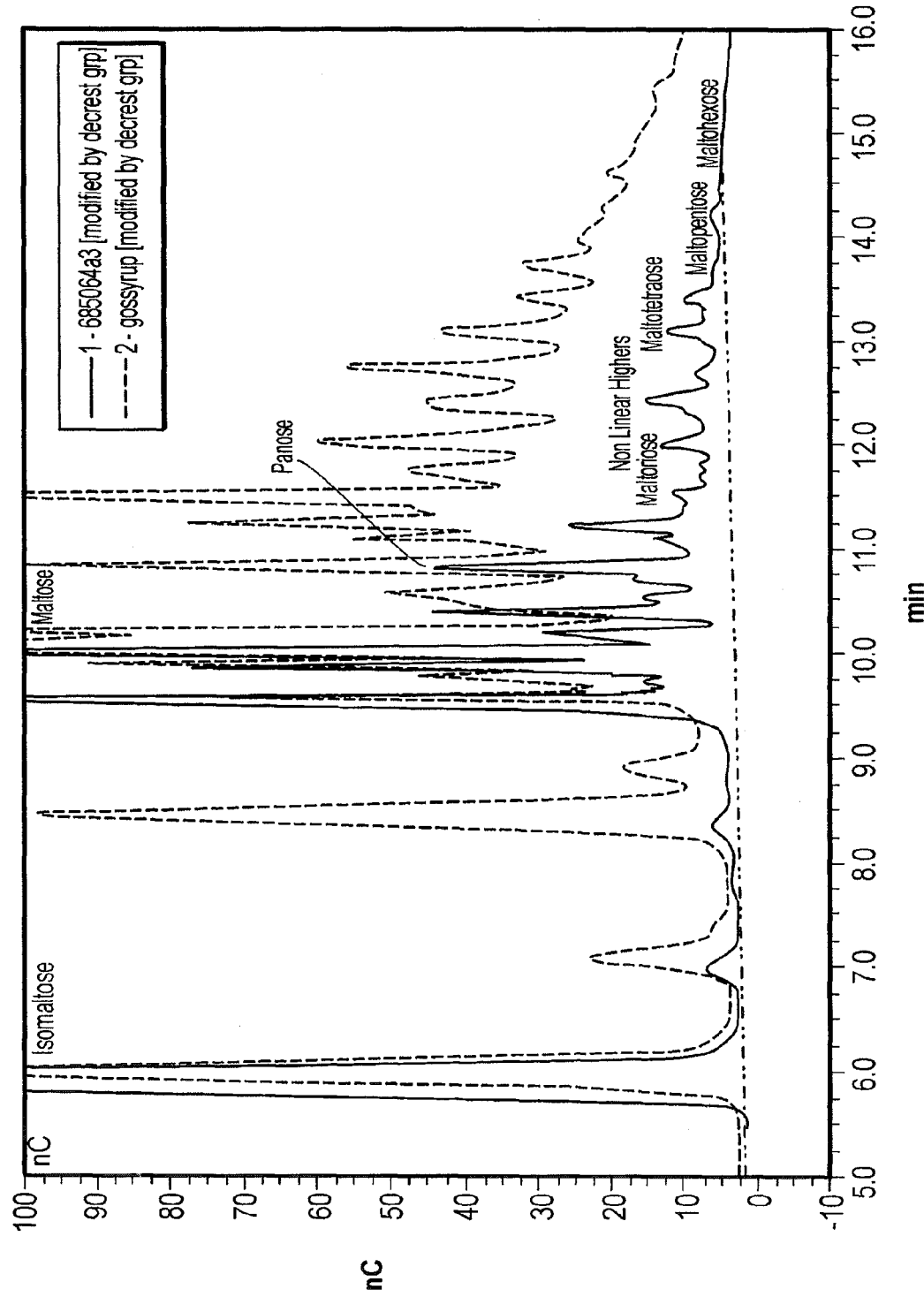
FIG. 13 shows an analysis of a syrup treated with acid in Example 6.

As FIG. 13 illustrates, the product of acid-treated syrup is a very broad distribution of sugar oligomers. It also shows a much higher concentration of oligomers of DP3 than the enzyme reverted syrup. Also, the acid-treated syrup contains sugars which do not appear in the enzyme-treated syrup. This is expected since the acid-catalyzed condensations can occur between any two hydroxyl groups, whereas enzymatic condensations are typically very specific in how two sugar units are joined together.

Figure 14:
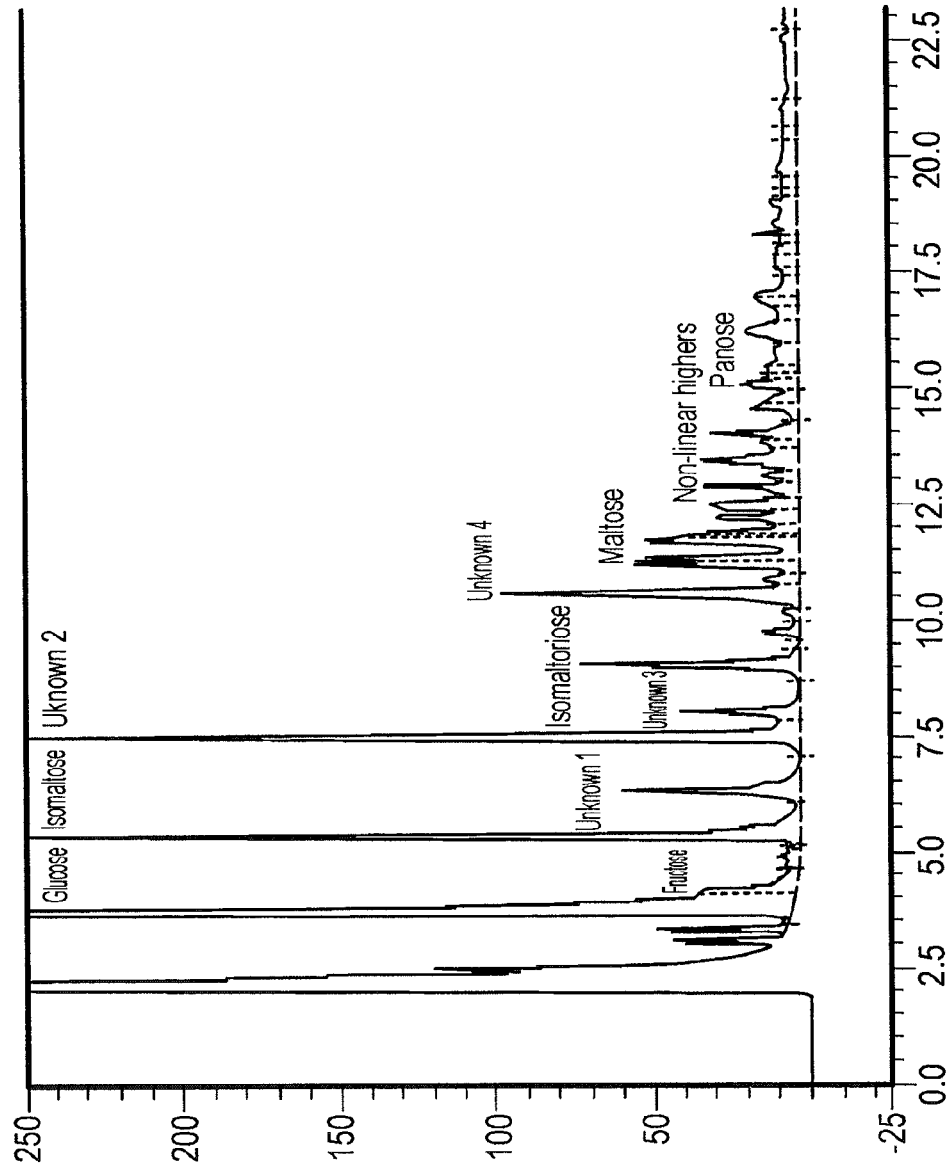
FIG. 14 shows a chromatographic analysis of a syrup treated with acid in Example 6.

A Dionex CarboPac PA200 column was used for ion chromatographic separation of the sugars. FIG. 14 shows a chromatographic trace of an acid-treated syrup resolved by this column. It clearly shows four components in the DP2-3 range that elute separately from maltose, isomaltose, maltotriose and panose. (These four all elute before maltose.) It also shows a number of peaks for unidentified higher oligomers.

Table 7 below shows changes in sugar distribution over time for these four lower-pH, higher-temperature treatments, using the PA200 column. (The last column in the table shows the amount of the "unknown 1-4" peaks, and is not included in the NL DP3+).

TABLE 7

| pH | C. temp | hr time | color | % of total sugars | | | |
|---|---|---|---|---|---|---|---|
| | | | | Glucose | NL DP3+ | L DP3+ | NL DP2-3? |
| 1.8 | 70 | 0 | white | 22 | 23 | 42 | 0 |
| 1.8 | 70 | 4 | white | 27 | 27 | 28 | 1.7 |
| 1.8 | 70 | 8 | white | 28 | 29 | 25 | 2.8 |
| 1.8 | 70 | 24 | white | 34 | 30 | 13 | 7.3 |
| 1.8 | 70 | 48 | tan | 37 | 30 | 4.7 | 14 |
| 1.2 | 70 | 0 | white | 22 | 23 | 42 | 0 |
| 1.2 | 70 | 4 | white | 33 | 30 | 15 | 5.9 |
| 1.2 | 70 | 8 | tan | 36 | 30 | 6.6 | 12 |
| 1.2 | 70 | 24 | tea | 36 | 30 | 0.5 | 20 |
| 1.2 | 70 | 48 | coffee | 35 | 29 | 0.3 | 21 |
| 1.8 | 80 | 0 | white | 22 | 23 | 42 | 0 |
| 1.8 | 80 | 4 | white | 39 | 28 | 1.6 | 18 |
| 1.8 | 80 | 8 | tan | 36 | 29 | 0.7 | 21 |
| 1.8 | 80 | 24 | tea | 35 | 30 | 0.5 | 20 |
| 1.8 | 80 | 48 | coffee | 35 | 29 | 0.4 | 20 |
| 1.2 | 80 | 0 | white | 22 | 23 | 42 | 0 |
| 1.2 | 80 | 4 | tan | 29 | 33 | 18 | 4.5 |
| 1.2 | 80 | 8 | tea | 32 | 32 | 11 | 8.6 |
| 1.2 | 80 | 24 | coffee + insol | 37 | 31 | 0.5 | 18 |
| 1.2 | 80 | 48 | coffee + insol | 33 | 32 | 0.2 | 21 |

Example 7

Enzyme Reversion—High Sugar

Approximately 35 gal of 43 DE corn syrup at 80% dry solids (Staley 1300) with an additional 5 gal of deionized water was slowly agitated in a tank and heated to a temperature of 60° C. About 1.6 gal of Spirizyme Plus FG enzyme was added to the syrup slowly and with good agitation. After 24 hours at 60° C., the syrup was heated to 85° C. and held for 20 minutes. The syrup was then diluted from 70% to 20% dry solids concentration by adding 100 gal water. The sugar solution was subjected to nanofiltration using a Desal NF3840C 30D nanofiltration cartridge at about 500 psi of pressure and at a temperature of 55-60° C. Fresh diafiltration water was added to maintain permeate flux in the range of 2 to 10 LMH. Filtration continued until the retentate contained less than 5% dextrose (d.s.b.) by combination of Karl Fisher and YSI dextrose analysis. The nanofiltration retentate was treated with 1% activated carbon on a dry solids basis. Next, the carbon was removed by filtration and the filtrate evaporated to 80.2% ds.

A saccharide analysis of the final product was performed by HPAE-PAD chromatography, and the results are shown in Table 8.

TABLE 8

| Component | Wt % d.s.b. |
|---|---|
| dextrose | 1.1% |
| fructose | 0.1% |
| isomaltose | 27.7% |
| maltose | 5.2% |

TABLE 8-continued

| Component | Wt % d.s.b. |
|---|---|
| maltotriose | 0.3% |
| panose | 3.2% |
| linear higher saccharides | 3.3% |
| nonlinear higher saccharides | 59.1% |

("Higher saccharides" in the above table means oligomers having a DP of three or more.)

Example 8

Enzyme Reversion—Low Sugar

Approximately 35 gal of 43 DE corn syrup at 80% dry solids (Staley 1300) with an additional 5 gal of deionized water was slowly agitated in a tank and heated to a temperature of 60° C. About 1.6 gal of Spirizyme Plus FG enzyme was added to the syrup slowly and with good agitation. After 24 hours at 60° C., the syrup was heated to 85° C. and held for 20 minutes. The syrup was then diluted from 70% to 20% dry solids concentration by adding 100 gal water. The sugar solution was subjected to ultrafiltration using a Desal UF-1 3840C 50D ultrafiltration cartridge at about 400 psi of pressure and at a temperature of 55-60° C. Fresh diafiltration water was added to maintain permeate flux in the range of 10 to 20 LMH. Filtration continued until the retentate contained less than 1% dextrose (d.s.b.) by combination of Karl Fisher and YSI dextrose analysis. The ultrafiltration retentate was treated with 1% activated carbon on a dry solids basis. Next, the carbon was removed by filtration and the filtrate evaporated to 73.4% ds.

A saccharide analysis of the final product was performed by HPAE-PAD chromatography, and the results are shown in Table 9.

TABLE 9

| Component | Wt % d.s.b. |
|---|---|
| dextrose | 1.0% |
| fructose | 0.1% |
| isomaltose | 6.0% |
| maltose | 7.5% |
| maltotriose | 0.4% |
| panose | 4.4% |
| linear higher saccharides | 7.2% |
| nonlinear higher saccharides | 73.3% |

Example 9

Enzyme Reversion—High Isomaltose

The syrup from Example 7 was subjected to ultrafiltration using a Desal UF-1 3840C 50D ultrafiltration cartridge at about 400 psi of pressure and at a temperature of 55-60° C. The permeate from this operation was then subjected to nanofiltration using a Desal NF3840C 30D nanofiltration cartridge at about 500 psi of pressure and at a temperature of 55-60° C. Fresh diafiltration water was added to maintain permeate flux in the range of 2 to 10 LMH. Filtration continued until the retentate contained less than 5% dextrose (d.s.b.) by combination of Karl Fisher and YSI dextrose analysis. The nanofiltration retentate was treated with 1% activated carbon on a dry solids basis. Next, the carbon was removed by filtration and the filtrate evaporated to 90.2% ds.

A saccharide analysis of the final product was performed by HPAE-PAD chromatography, and the results are shown in Table 10.

TABLE 10

| Component | Wt % d.s.b. |
|---|---|
| dextrose | 2.8% |
| fructose | 0.0% |
| isomaltose | 70.8% |
| maltose | 6.5% |
| maltotriose | 0.1% |
| panose | 0.6% |
| linear higher saccharides | 0.0% |
| nonlinear higher saccharides | 19.2% |

Example 10

Acid Reversion—Moderately Resistant

Approximately 35 gal of 43 DE corn syrup at 80% dry solids (Staley 1300) was slowly agitated in a tank and heated to a temperature of 80° C. About 4.1 lb 37% hydrochloric acid was added to the syrup slowly and with good agitation. The reaction was maintained at approximately 80% dry solids concentration, as measured by Karl Fischer analysis through periodic additions of water. After 24 hours, heating was discontinued and approximately 35 gal of 0.35% sodium hydroxide solution was added slowly and with good agitation. Next, pH was adjusted to 5.0 and water was added to reach a final sugar concentration of 30% d.s. The sugar solution was subjected to ultrafiltration using a Desal UF-1 ultrafiltration cartridge at about 400 psi of pressure and at a temperature of 55-60 C. Fresh diafiltration water was added to maintain permeate flux in the range of 10 to 20 LMH. Filtration continued until the retentate contained less than 5% dextrose (d.s.b.) by combination of Karl Fisher and YSI dextrose analysis. The ultrafiltration retentate was treated with 2% activated carbon on a dry solids basis. Next, the carbon was removed by filtration and the filtrate evaporated to 71.5% ds.

A saccharide analysis of the final product was performed by HPAE-PAD chromatography, and the results are shown in Table 11.

TABLE 11

| Component | Wt % d.s.b. |
|---|---|
| dextrose | 6.4% |
| fructose | 0.1% |
| isomaltose | 1.6% |
| maltose | 3.8% |
| maltotriose | 4.3% |
| panose | 3.8% |
| linear higher saccharides | 25.6% |
| nonlinear higher saccharides | 54.9% |

Example 11

Acid Reversion followed by Hydrogenation

Approximately 35 gal of 63 DE corn syrup at 80% dry solids (SWEETOSE® 4300) was slowly agitated in a tank.

Then 37% hydrochloric acid was added slowly with good agitation to give 0.25% (w/w) HCl with respect to syrup dry solids. The mixture was then heated to a temperature of 80° C. The reaction was maintained at approximately 80% dry solids concentration, as measured by Karl Fischer analysis through periodic additions of water. After 16 hours, heating was discontinued and pH was adjusted to 4.5 using 0.35% sodium hydroxide solution. Additional water was added to reach a final sugar concentration of 30% d.s. The sugar solution was subjected to ultrafiltration using a Desal UF-1 ultrafiltration cartridge at about 400 psi of pressure and at a temperature of 55-60° C. Fresh diafiltration water was added to maintain permeate flux in the range of 10 to 20 LMH. Ultrafiltration continued until the retentate contained less than 10% dextrose (d.s.b.) by combination of Karl Fisher and YSI dextrose analysis. The ultrafiltration retentate was subjected to nanofiltration using a Desal NF3840C 30D nanofiltration cartridge at about 500 psi of pressure and at a temperature of 55-60° C. Fresh diafiltration water was added to maintain permeate flux in the range of 2 to 10 LMH. Filtration continued until the retentate contained less than 1% dextrose (d.s.b.) by combination of Karl Fisher and YSI dextrose analysis. The nanofiltration retentate was treated with 1% activated carbon on a dry solids basis. Next, the carbon was removed by filtration and the filtrate evaporated to 73.5% ds.

Dextrose Equivalence (DE) for this product was measured by AOAC method 920.51 (Lane Eynon) and was found to be 21 DE. A saccharide analysis of this product was performed by HPAE-PAD chromatography, and the results are shown in Table 12.

TABLE 12

| Component | Wt % d.s.b. |
| --- | --- |
| dextrose | 1.4% |
| fructose | 0.1% |
| isomaltose | 0.0% |
| maltose | 4.3% |
| sorbitol | 0.0% |
| panose | 6.3% |
| linear higher saccharides | 12.6% |
| nonlinear higher saccharides | 75.2% |

This product was further subjected to hydrogenation reaction conditions. About 1.5 kg of a 43% d.s. solution of the material described in table 9 was introduced into a pressure reactor and 6.45 grams of 5% ruthenium on carbon catalyst was added with stirring to give 0.05% ruthenium (w/w) on syrup dry solids. The reactor was closed, purged with nitrogen gas, and then pressurized with hydrogen gas to a pressure of 600 psi. The reactor was then heated to 120° C. This temperature and a hydrogen pressure of 600-650 psi was maintained for four hours. The reaction vessel was cooled, carefully vented and purged with nitrogen. The reaction product was then filtered through diatomaceous earth to give a clear colorless solution.

Dextrose Equivalence (DE) for this product was measured by AOAC method 920.51 (Lane Eynon) and was found to be 5 DE. A saccharide analysis of this product was performed by HPAE-PAD chromatography, and the results are shown in Table 13.

TABLE 13

| Component | Wt % d.s.b. |
| --- | --- |
| dextrose | 3.1% |
| fructose | 0.2% |
| isomaltose | 0.0% |
| maltose | 5.9% |
| sorbitol | 3.0% |
| panose | 5.6% |
| linear higher saccharides | 9.5% |
| nonlinear higher saccharides | 72.7% |

Example 12

Englyst Digestion Assay

The product materials from Examples 7, 8 and 10, were tested for digestibility using an Englyst assay. About 600 mg of carbohydrate d.s.b. was added to 20 mL of 0.1 M sodium acetate buffer in a test tube. The contents were mixed and then heated to about 92° C. for 30 minutes, then cooled to 37° C. Then 5 mL of enzyme solution was added to the test tube and it was agitated by shaking in a water bath at 37° C. Small samples were removed at both 20 min and 120 min. The enzyme was inactivated; the samples were filtered and measured for digestibility using a dextrose test from YSI Inc. A 10 DE maltodextrin (STAR-DRI 10), known to be very digestible, was also tested as a comparison. The results of the digestibility assay and a saccharide analysis are shown in Table 14. A 10 DE maltodextrin is included in Table 5 for comparison. All percentages in Table 14 are on a d.s.b.

TABLE 14

| material | % rapidly digestible | % slowly digestible | % resistant | % non-linear highers (by HPAE) |
| --- | --- | --- | --- | --- |
| Example 7 | 4.2 | 10.2 | 85.6 | 59.1 |
| Example 8 | 5.2 | 10.0 | 84.8 | 73.3 |
| Example 10 | 24.8 | 5.5 | 69.8 | 54.9 |
| 10 DE maltodextrin | 89.7 | 3.4 | 7.0 | 13.7 |

("Highers" in Table 14 refers to oligomers having a degree of polymerization of three or more.)

There was an excellent correlation ($R^2=0.95$) between the percentage of non-linear highers in the material and the percentage of the material that was resistant to digestion.

Example 13

Hard Candy, Lemon Flavored 980 grams (d.s.b.) of Example 7 (Enzyme Reversion—High Sugar) was added to a pot and cooked on a stove to an internal temperature of 300° F. Next, 15 grams of citric acid and 1.2 grams of sucralose were added with stirring. Then, yellow color and lemon flavor were added and the mixture was poured into candy moulds. The hard candy was formed upon cooling to room temperature.

Example 14

Jelly Candy, Grape Flavored 840 grams of Example 8 (Enzyme Reversion—Low Sugar) was added to a mixing bowl. Purple color and grape flavor was added to taste. Next, 160 grams of MiraThik 468 instant starch was added in portions with moderately vigorous mixing. The jelly candy was formed after cooling to room temperature over 20 minutes.

Example 15

Yogurt 900 grams of milk (2% fat) was added to a pot on a stove. Next 80 grams (d.s.b.) of Example 10 (Acid Reversion—Moderately Resistant) was added with stirring. Then the mixture was heated to a target temperature of 150° F. As the mixture was heating, 20 grams of Rezista 682 starch was added in portions with mixing. After the mixture reached an internal temperature of 150° F., it was held for five minutes, then passed through a two stage homogenizer (1500/500 psi). The product was next pasteurized at 190° F. for 5 minutes. Then the mixture was cooled to 90° F. and inoculated with active yogurt cultures. The incubation was allowed to continue until the yogurt reached a pH of 4.5, then it was refrigerated prior to consumption.

Example 16

The following general procedures were used to prepare samples of digestion-resistant corn syrups in accordance with the present invention. In the preparation of some low sugar samples, nanofiltration was run to less than 1% dextrose, instead of 5% as described in the general procedures below.

Sample 1—Oligomer Syrup from HFCS Raffinate

1. Transfer mixed raffinate from high fructose corn syrup (HFCS) process to filtration unit and concentrate volume by 10× to 30× with Desal UF-1 membrane. Note: this step is optional, depending on the final DP2 target.
2. Switch filtration membrane to nanofiltration (Desal NF3840C 30D "DL"). Add fresh diafiltration water at a rate to maintain permeate flux in the range of 2 to 10 LMH. Continue until retentate contains less than 5% dextrose (d.s.b.) by combination of Karl Fisher and YSI dextrose analysis.
3. Collect retentate product and add 1% activated carbon on a dry solids basis. Refrigerate.
4. Remove carbon by filtration and evaporate filtrate to >70% ds.

Sample 2—Oligomer Syrup from Dextrose Greens

1. Transfer diluted dextrose greens (at 20-30% ds) to filtration unit and concentrate volume by 10× to 30× with Desal UF-1 membrane. Note: this step is optional, depending on the final DP2 target.
2. Switch filtration membrane to nanofiltration (Desal NF3840C 30D "DL"). Add fresh diafiltration water at a rate to maintain permeate flux in the range of 2 to 10 LMH. Continue until retentate contains less than 5% dextrose (d.s.b.) by combination of Karl Fisher and YSI dextrose analysis.
3. Collect retentate product and add 1% activated carbon on a dry solids basis. Refrigerate.
4. Remove carbon by filtration and evaporate filtrate to >70% ds.

Sample 3—Enzymatic Reversion of STALEY® 1300 Corn Syrup to form >25% Non-Linear Oligomers of Dextrose 1. Pump 35 gal Staley 1300 syrup and 5 gal water to tank. Start agitator and begin heating.
2. Heat syrup to 60° C. and confirm that temperature has stabilized at 60° C.±5 C.
3. Add 1.6 gal (6.1 liter) Spirizyme Plus FG enzyme to the syrup.
4. Hold at 60° C.±5 C for 24 hr.
5. At the end of the 60° C./24 hr hold, heat syrup to 85-90° C. Once syrup temperature has stabilized above 85° C., hold for 20 min.
6. Turn off heat to tank.
7. Dilute syrup from 70% to 20% solids by adding 100 gal water (140 gal total).
8. Transfer to filtration unit and concentrate volume by 10× to 30× with Desal UF-1 membrane.
9. Switch filtration membrane to nanofiltration (Desal NF3840C 30D "DL"). Add fresh diafiltration water at a rate to maintain permeate flux in the range of 2 to 10 LMH. Continue until retentate contains less than 1% dextrose (d.s.b.) by combination of Karl Fisher and YSI dextrose analysis.
10. Collect retentate product and add 1% activated carbon on a dry solids basis. Refrigerate.
11. Remove carbon by filtration and evaporate filtrate to >70% ds.

Sample 4—Acid-Catalyzed Restructuring of Tate & Lyle SWEETOSE® 4300 Corn Syrup

1. Pump 35 gal SWEETOSE® 4300 syrup to tank. Start agitator and begin heating to 80° C.
2. Add ~2.8 lb 37% hydrochloric acid to the syrup slowly and with good agitation (calculated to give 0.25% HCl dry solids on syrup dry solids in the reaction, based on assumption that 4300 syrup density is 11.9 lb/gal).
3. Hold at 80% ds±5%. Remove a reaction sample every two hours and dilute with an equal weight of DI water. Run Karl Fischer on diluted sample. If less than 40% ds do nothing. If greater than 40% ds, add 4 lb DI water for every 100 lb of initial reaction contents for every 1% ds over 40% ds.
4. In addition to the above samples for Karl Fischer, collect samples to be used for monitoring the progress of the reaction. Remove these at the following intervals following acid addition: 2 hr, 4 hr, 8 hr, and 16 hr. After each sampling, move quickly to adjust the pH of the sample by adding an equal weight of 0.35% NaOH solution, mix well, and measure pH. Adjust sample pH as needed to bring to 5.0-6.5.
5. At the end of the 80° C./16 hr hold, discontinue heating. Add 0.35% caustic solution, slowly and with good agitation until pH is stable in the range of 4.5-5.5.
6. Add dilution water, if needed, to reach a final solids concentration of 30% d.s.
7. Transfer to filtration unit and concentrate volume by 10× to 30× with Desal UF-1 membrane. Note: this step is optional, depending on the final DP2 target.
8. Switch filtration membrane to nanofiltration (Desal NF3840C 30D "DL"). Add fresh diafiltration water at a rate to maintain permeate flux in the range of 2 to 10 LMH. Continue until retentate contains less than 5% dextrose (d.s.b.) by combination of Karl Fisher and YSI dextrose analysis.
9. Collect retentate product and add 1% activated carbon on a dry solids basis. Refrigerate.
10. Remove carbon by filtration and evaporate filtrate to >70% ds.

Sample 5—Phosphoric and Hydrochloric Acid-Catalyzed Restructuring of SWEETOSE® 4300 Corn Syrup 1. Pump 35 gal SWEETOSE® 4300 syrup to tank. Start agitator and begin heating to 80° C.
2. Add ~0.35 lb 75% phosphoric acid to the syrup slowly and with good agitation. Then add 0.10 lb 37% hydrochloric acid to the syrup slowly and with good agitation (calculated to give 0.08% H3PO4 and 100 ppm HCl dry solids on syrup dry solids in the reaction, based on assumption that 4300 syrup density is 11.9 lb/gal).
3. Hold at 80% ds±5%. Remove a reaction sample every two hours and dilute with an equal weight of DI water. Run Karl Fischer on diluted sample. If less than 40% ds, do nothing. If greater than 40% ds, add 4 lb DI water for every 100 lb of initial reaction contents for every 1% ds over 40% ds.

4. In addition to the above samples for Karl Fischer, collect samples to be used for monitoring the progress of the reaction. Remove these at the following intervals following acid addition: 2 hr, 4 hr, 8 hr, and 16 hr. After each sampling, move quickly to adjust the pH of the sample by adding an equal weight of 0.35% NaOH solution, mix well, and measure pH. Adjust sample pH as needed to bring to 5.0-6.5.

5. At the end of the 80° C./16 hr hold, discontinue heating. Add 0.35% caustic solution, slowly and with good agitation until pH is stable in the range of 4.5-5.5.

6. Add dilution water, if needed, to reach a final sugar concentration of 30% d.s.

7. Transfer to filtration unit and concentrate volume by 10× to 30× with Desal UF-1 membrane. Note: this step is optional, depending on the final DP2 target.

8. Switch filtration membrane to nanofiltration (Desal NF3840C 30D "DL"). Add fresh diafiltration water at a rate to maintain permeate flux in the range of 2 to 10 LMH. Continue until retentate contains less than 5% dextrose (d.s.b.) by combination of Karl Fisher and YSI dextrose analysis.

9. Collect retentate product and add 1% activated carbon on a dry solids basis. Refrigerate.

10. Remove carbon by filtration and evaporate filtrate to >70% ds.

Sample 6—Acid-Catalyzed Restructuring of Tate and Lyle STALEY® 1300 Corn Syrup

1. Pump 35 gal SWEETOSE® 1300 syrup to tank. Start agitator and begin heating to 80° C.

2. Add ~2.8 lb 37% hydrochloric acid to the syrup slowly and with good agitation (calculated to give 0.25% HCl dry solids on syrup dry solids in the reaction, based on assumption that 4300 syrup density is 11.9 lb/gal).

3. Hold at 80° ds±5%. Remove a reaction sample every 2 hours and dilute with an equal weight of DI water. Run Karl Fischer on diluted sample. If less than 40% ds do nothing. If greater than 40% ds add 4 lb DI water for every 100 lb of initial reaction contents for every 1% ds over 40% ds.

4. In addition to the above samples for Karl Fischer, collect samples to be used for monitoring the progress of the reaction. Remove these at the following intervals following acid addition: 2 hr, 4 hr, 8 hr, and 16 hr. After each sampling, move quickly to adjust the pH of the sample by adding an equal weight of 0.35% NaOH solution, mix well, and measure pH. Adjust sample pH as needed to bring to 5.0-6.5.

5. At the end of the 80° C./16 hr hold, discontinue heating. Add 0.35% caustic solution, slowly and with good agitation until pH is stable in the range of 4.5-5.5.

6. Add dilution water, if needed, to reach a final solids concentration of 30% d.s.

7. Transfer to filtration skid and concentrate volume by 10× to 30× with Desal UF-1 membrane. Note: this step is optional, depending on the final DP2 target.

8. Switch filtration membrane to nanofiltration (Desal NF3840C 30D "DL"). Add fresh diafiltration water at a rate to maintain permeate flux in the range of 2 to 10 LMH. Continue until retentate contains less than 5% dextrose (d.s.b.) by combination of Karl Fisher and YSI dextrose analysis.

9. Collect retentate product and add 1% activated carbon on a dry solids basis. Refrigerate.

10. Remove carbon by filtration and evaporate filtrate to >70% ds.

Some of the syrups prepared by these methods were used in the subsequent examples, where they are referenced by sample number.

Example 17

A breakfast cereal comprising an oligosaccharide composition according to the present invention can be prepared as described below. The cereal comprises an extruded portion and a coating placed on the extruded portion. The composition of the extruded portion can be as follows (by weight percent):

| Corn Meal | 54.80 |
| --- | --- |
| Whole Wheat Flour | 25.19 |
| Resistant Corn Syrup Solids (Sample 5) | 13.51 |
| Whole Oat Flour | 5.00 |
| Vitamin blend | 0.50 |
| Salt | 1.00 |
| Total | 100.0 |

The extruded portion is prepared using the following steps: Uniformly mix ingredients together in a mixer/blender. Feed the dry blend and water to achieve target extrusion moisture. Use typical extrusion and drying conditions. Cool and package.

The coating composition is a 75% solids solution of 50% sugar, 50% resistant corn syrup. It is prepared using the following steps: Place spray gun in convection oven at 250° F. to preheat. Weigh out approximately 100 g of cereal and place into tumbler that has been first coated with oil based release agent. Blend the dry ingredients (75% total dry solids) in kettle. Add water and mix. Heat the syrup to approximately 230° F. (rapid boil). Weight out the desired amount of syrup needed to give the correct ratio of cereal:coating to achieve the appropriate ratio (approximately 45-50% coating by final weight of the cereal). Pour the syrup into the pre-heated spray gun and attach the air line hose to the spray gun. As the cereal is tumbling, spray the syrup onto the cereal until all of the syrup has been applied. After desired amount of coating is applied, allow coated cereal to tumble in enrobing drum for three minutes to insure an even coating. Pour the coated cereal out onto a baking sheet that has been sprayed with release agent. Dry the cereal in convection oven at 250° F. for six minutes or until cereal appears dry. Stir halfway through drying to prevent cereal from sticking to the pan and clumping of the cereal. After drying, allow cereal to cool for five minutes. After cooling, weigh the cereal to determine the percent coating. Package cereal in plastic storage bag.

Example 18

Yogurt comprising an oligosaccharide composition according to the present invention was prepared.

The ingredients were

| 2% milk | 3614 |
| --- | --- |
| Non fat dry milk (NFDM) | 133 |
| Resistant corn syrup (Sample 5) | 200 |
| Rezista 682 starch | 53 |
| Total weight: | 4000 g |

The yogurt was prepared using the following steps: Disperse dry ingredients into liquid ingredients using a pump and funnel or liquefier. Preheat to 150° F. Homogenize at 1500/

500 psi using a two stage homogenizer. Pasteurize at 190° F. for 5 minutes. Cool to 90° F. and add culture. Culture to finished pH 4.4. Stir the product and begin to cool to stop active culture growth. Package and cool.

Example 19

A yogurt drink comprising an oligosaccharide composition according to the present invention was prepared.
The ingredients were

| Skim Milk | 94.21 |
|---|---|
| Whey protein concentrate | 1.2 |
| Resistant corn syrup (Sample 5) | 4.25 |
| Stabilizer blend | 0.442 |
| Sucralose solution | 0.008 |
| Total | 100.0 |

The yogurt drink was prepared using the following steps: Add dry ingredients to liquid using a pump and funnel or liquefier. Preheat to 150° F. Homogenize at 1500/500 psi using a two stage homogenizer. Pasteurize at 190° F. for 5 minutes. Cool to 90° F. and add culture. Culture to finished pH 4.4. Break, package and cool.

Example 20

A frozen novelty comprising an oligosaccharide composition according to the present invention can be prepared as described below.
The ingredients are:

| Ingredients | % |
|---|---|
| Butterfat | 1.20% |
| Milk solids, nonfat (MSNF) | 11.75% |
| Sucrose | 10.70% |
| Resistant corn syrup (Sample 5) | 6.70% |
| Whey Protein 34 | 2.00% |
| Polydextrose | 4.10% |
| Stabilizer Blend | 0.67% |
| Total Solids | 37.12% |
| Weight per Gallon | 9.63 lbs |

The frozen novelty can be prepared using the following steps: Standardize cream, milk and nonfat dry milk to desired butterfat and milk-solids, nonfat (MSNF) level. Add the stabilizer to liquid sugar using moderate agitation to ensure proper dispersion. Blend milk and liquid sugar portions thoroughly in batch tank. Incorporate milk fat solids portion with mix and use low agitation to minimize air incorporation. Pasteurize at 185° F. for 30 seconds or the equivalent time and temperature. Homogenize using a two stage homogenizer at 2500 psi double stage (2000 and 500 psi, first and second stage respectively). Cool mix to 34-38° F. and hold for a minimum of four hours for aging. (Overnight aging is preferred).

Example 21

A sugarless ice cream comprising an oligosaccharide composition according to the present invention was prepared.
The ingredients were:

| Butterfat | 7-12% |
|---|---|
| Milk Solids Non-fat | 10-12% |
| Resistant corn syrup (Sample 5) | 12-15% |
| maltodextrin | 3-5% |
| sucralose | 0.0085%-0.012% |
| vitamin A palmitate | 0.009%, |
| Stabilizer blend | 0.40-0.50% |

The sugarless ice cream was prepared using the following steps: Stabilizer blend, sucralose, vitamin A and maltodextrin are mixed in skim milk under shear. Resistant corn syrup is added to the mixture under shear. Cream (butterfat) is then added slowly to avoid churning and aeration. The ice cream is then pasteurized and homogenized at 175° F. for 30 seconds, 2500 psi 2 stage, respectively. The mix is refrigerated overnight (35-40° F.) and then processed to a frozen state using a continuous freezing system.

Example 22

Marshmallows comprising an oligosaccharide composition according to the present invention were prepared.
The ingredients were prepared in three separate parts:

| Part A | |
|---|---|
| Gelatin 250 Bloom | 22.5 |
| Cold Water | 44.5 |
| Part B | |
| Resistant corn syrup (Sample 5, 71%) | 337.5 |
| Part C | |
| Hystar Maltitol Syrup | 585.5 |
| Total | 990 g |

The marshmallows were prepared using the following steps: Mix ingredients in Part A (gelatin into water). Preheat resistant corn syrup to 135° F. Heat maltitol syrup to 200° F. Combine Parts B and C and cool to 145° F. Melt Part A in microwave for 30 seconds to dissolve gelatin. Add Part A to other parts and whip mixture with a wire whisk in a Hobart mixer until a 0.5 density is reached. Fill marshmallow into pastry bags and deposit into starch molds.

Example 23

A hard candy comprising an oligosaccharide composition according to the present invention was prepared.
The ingredients were:

| Sugar | 42.0 |
|---|---|
| Resistant Corn Syrup (Sample 4) | 43.7 |
| Water | 14.3 |
| Total | 100.0 |

The hard candy was prepared using the following steps: Mix sugar and resistant corn syrup with water. Heat to ca. 138° C. with Bosch cooker and vacuum for two minutes to 129° C. Add citric acid (18 g for 3 kg product), and flavor. Deposit or form the sweets.

Example 24

A gelatin jelly candy comprising an oligosaccharide composition according to the present invention was prepared.

The ingredients were:

| | |
|---|---|
| Sugar | 35.2 |
| Resistant corn syrup (Sample 5, 71%) | 36.6 |
| Water | 12.3 |
| Gelatin | 6.6 |
| Water | 9.3 |
| Total | 100.0 |

The gelatin jelly candy was prepared using the following steps: Mix gelatin and water and keep at 70° C. Mix sugar, resistant corn syrup, and water. Heat until solids reach 89% (approximately 120° C.). Cool down to 90° C. Add gelatin solution. Add citric acid solution 50% (18 g/1000 g), and flavor and color to suit. Deposit in molding starch and dry at ambient conditions to a weight percentage of dry solids (ds) of 81-82%.

Example 25

A jam comprising an oligosaccharide composition according to the present invention was prepared.
The ingredients were:

| | |
|---|---|
| Water | 36.5 |
| Apricots | 32.8 |
| Resistant corn syrup (Sample 5, 71%) | 15.5 |
| Maltodextrin | 10.2 |
| Pectin (low methoxy) | 4.58 |
| Xanthan Gum | 0.10 |
| Citric Acid | 0.15 |
| Sucralose | 0.06 |
| Potassium Sorbate | 0.10 |
| Calcium Chloride | 0.01 |
| Total | 100.0 |

The jam was prepared using the following steps: Mix dry ingredients. Add dry ingredients to liquid ingredients and fruit. Heat to 220° F. Put into containers and cool.

Example 26

A sweetened children's beverage comprising an oligosaccharide composition according to the present invention was prepared.
The ingredients were:

| | |
|---|---|
| Water | 86.35 |
| Citric Acid | 0.15 |
| Strawberry flavor | 0.10 |
| Resistant corn syrup (Sample 5, 73.4%) | 13.3 |
| Color (#40, 10%) | 0.10 |
| Sucralose | 0.004 |

The drink was prepared using the following steps: Add ingredients slowly into the water using a mixer. Heat drink to 180° F. Immediately hot fill into bottles. Place bottles in a water bath to cool.

Example 27

An orange flavored juice soda beverage comprising an oligosaccharide composition according to the present invention was prepared.

The ingredients were:

| Ingredient | % |
|---|---|
| Potassium citrate | 0.0200 |
| Acid (citric, malic) | 0.2000 |
| RCS (Sample 5, 71% ds) | 1.8750 |
| High intensity sweeteners (sucralose, Ace-K) | 0.015 |
| 5% Clarified Val OJ Conc., 60.56 Brix | 1.0177 |
| Red #40 | 0.0009 |
| Yellow #5 | 0.0044 |
| Orange flavor | 0.1218 |
| Filtered water | 96.7452 |
| | 100 |

The orange juice soda was prepared using the following steps: Dry blend the potassium citrate, acids, resistant corn syrup, and high intensity sweeteners. Blend orange juice concentrate, Red #40, Yellow #5, orange flavor and the blend from the previous step into the water. Carbonate to desired volume of $CO_2$ (2-4).

Example 28

A savory high solids filling comprising an oligosaccharide composition according to the present invention was prepared.
The ingredients were:

| Ingredients | Amount (g) |
|---|---|
| Tate and Lyle texturizing blend[1] | 18.6 |
| Canola Oil | 34 |
| Cheese Flavors | 28 |
| Resistant corn syrup solids (Sample 5) | 17 |
| Salt | 1.3 |
| Jalapeno Flavors | 0.75 |
| Lactic Acid | 0.2 |
| Citric Acid | 0.15 |
| TOTAL | 100 |

[1]Blend of food starch modified, wheat protein, and maltodextrin.

Ingredients were incorporated into the product mixture in the following order: (1) Canola oil, (2) Flavors, Citric Acid, Lactic Acid and Salt, (3) resistant corn syrup, and (4) Tate and Lyle Texturizing Blend.

Example 29

A high solids fruit filling comprising an oligosaccharide composition according to the present invention was prepared.
The ingredients were:

| | % |
|---|---|
| Part A | |
| Isosweet 5500 H FCS | 21 |
| Mirathik 603 (food-modified starch) | 6 |
| Part B | |
| resistant corn syrup (Sample 6) | 70.88 |
| water | 1.55 |
| nat. and art. rasp. flavor 256639 (tastemaker) | 0.3 |

-continued

| | % |
|---|---|
| Part C | |
| malic acid | 0.1 |
| citric acid | 0.1 |
| red color 09310 (WJ) | 0.06 |
| blue color 09918 (WJ) | 0.01 |
| | 100 |

The jam was prepared using the following steps: Place Part A ISOSWEET® 5500 in a Hobart mixer. Slowly add Mirathik 603 while mixing for 1.5 minutes. Add Part B resistant corn syrup, flavor, and water. Blend until uniform (1 minute). Allow to rest for about three minutes until mixture becomes thick. Preblend Part C ingredients and add to the mixture. Blend until uniform. Allow filling to set 24 hours to achieve full viscosity.

Example 30

A sheeted cracker comprising an oligosaccharide composition according to the present invention was prepared.

The ingredients were:

| Flour | 70.949 |
|---|---|
| Resistant corn syrup solids (Sample 5) | 17.00 |
| Shortening | 10.0 |
| Sucralose | 0.001 |
| Sodium bicarbonate | 0.70 |
| Salt | 0.50 |
| Monocalcium phosphate | 0.85 |
| Total | 100.00 |
| Amount of water | 30 |

The sheeted cracker was prepared using the following steps: Mix dough until all ingredients are wetted and dough is pliable. Sheet dough to 1.1 mm. Cut pieces. Bake in convection oven (low fan) at 350° F. for five minutes.

Example 31

An expanded extruded snack comprising an oligosaccharide composition according to the present invention was prepared.

The ingredients were:

| Corn flour | 75.00 |
|---|---|
| Resistant corn syrup solids (Sample 5) | 23.50 |
| Salt | 1.50 |
| Total | 100.0 |

The expanded extruded snack was prepared using the following steps: Mix dry ingredients. Feed dry ingredients into the extruder. Extrude into proper shapes. Dry for 10 minutes to 1% finished moisture content.

Example 32

Tortilla chips comprising an oligosaccharide composition according to the present invention was prepared.

The ingredients were:

| Corn Chip #8 flour | 23.5 |
|---|---|
| Tortilla Chip #1 flour | 24.0 |
| Resistant corn syrup (Sample 5) | 2.50 |
| water | 40.0 |
| Total | 100.0 |

The tortilla chips were prepared using the following steps: Make a 1:1 mixture of Tortilla Chip #1 flour and Corn Chip #8 flour. Mix on low speed for one minute in Hobart mixer. Add resistant corn syrup and mix on low for one minute. With the mixer still running on low speed, slowly add room temperature water in a stream to the dry mixture. Once all the water is added, increase mixer speed and mix for three minutes. Cover dough and let sit for 30 minutes in a plastic beaker. Sheet the dough using a Rondo sheeter, and gradually roll dough to have about a 1.3 mm thickness (testing thickness by using micrometer). Use the Rondo sheeter, cut the dough using the cutter by placing the dough horizontally. Fry for approximately 1:45 to 2 minutes (until chips appear golden brown and bubbling was almost ceased) in a fryer pre-heated to 375° F. While chips are frying use a metal spatula to stir the chips so they are constantly being submerged on both sides (to help even fat absorption). Remove from fryer and let chips drain for four minutes by hanging the basket. Pour chips onto a cloth towel and let sit for six minutes. Bag, seal, and label the tortilla chips in a plastic bag.

Example 33

A gelatin dessert dry mix comprising an oligosaccharide composition according to the present invention was prepared.

The ingredients were:

| Resistant corn syrup solids (Sample 5) | 88.66 |
|---|---|
| Gelatin 250 bloom | 9.00 |
| Adipic acid | 0.90 |
| Fumaric acid | 0.60 |
| Strawberry flavor | 0.50 |
| Disodium phosphate | 0.20 |
| Color (red #40) | 0.14 |
| Sucralose | 0.03 |

The gelatin dessert dry mix was prepared using the following steps: Mix dry ingredients. Weigh 85.1 g of dry mix and add to 226.8 g of water at 212° F. Dissolve completely. Add 226.8 g of cold water and mix thoroughly. Refrigerate at least four hours.

Example 34

A snack bar comprising an oligosaccharide composition according to the present invention was prepared, comprising a high solids filling, a binding syrup, and an extruded piece.

The ingredients for the high solids filling were:

| Part A | |
|---|---|
| Resistant corn syrup (Sample 6) | 21.00 |
| MiraThik 603 starch | 6.00 |
| Part B | |
| Resistant corn syrup (sample 6) | 80.88 |
| Water | 1.55 |
| Raspberry flavor | 0.30 |

| Part C | |
|---|---|
| Malic Acid | 0.10 |
| Citric Acid | 0.10 |
| Red Color | 0.06 |
| Blue color | 0.01 |
| Total | 100.00 |

The high solids filling was prepared using the following steps: Place part A, comprising resistant corn syrup, in a mixer. Slowly add Mirathik 603 while mixing on a slow speed for 1.5 minutes. Add part B (resistant corn syrup, flavor, water) and blend until uniform (one minute on low speed). Allow to rest for about 3 minutes until mixture becomes thick. Preblend part C ingredients and add to mixture. Blend until uniform (allow filling to set 24 hours to achieve full viscosity.).

The ingredients for the binding syrup were:

| | |
|---|---|
| Resistant corn syrup (Sample 2) | 67.7 |
| Glycerine | 10.7 |
| StaSlim 150 starch | 13.3 |
| Shortening | 7.5 |
| Salt | 0.8 |
| Total | 100.0 |

The binding syrup was prepared using the following steps: Combine and heat to 172° F. Add to cereal/granola pieces and combine to coat pieces evenly. Combine at a ratio of 54% syrup, 46% cereal.

The ingredients for the extruded piece were:

| | |
|---|---|
| Corn meal | 55.30 |
| Whole wheat flour | 25.19 |
| Resistant corn syrup (Sample 2) | 13.51 |
| Whole oat flour | 5.00 |
| Salt | 1.00 |
| Total | 100.0 |

The extruded piece was prepared using the following steps: Uniformly mix ingredients together in a mixer/blender. Feed the dry blend and water to achieve target extrusion moisture. Use typical extrusion and drying conditions. Cool and package.

Binding syrup is mixed to coat extruded piece or other particulate and mixture is sheeted or formed and cut to appropriate size. High solids filling typically would be added between the two sheets of binder/particulate mixture.

Example 35

A spice cake comprising an oligosaccharide composition according to the present invention was prepared.
The ingredients were:

| Ingredient | % |
|---|---|
| water | 40.67 |
| Purasnow cake flour | 21.56 |
| sorbitol | 17.70 |
| RCS solids (Sample 5) | 8.85 |
| Mira-Thik 603 food starch modified | 1.00 |
| Core M90 (maltodextrin, sucralose) | 0.25 |
| EC-25 emulsifier | 2.65 |
| Provon 190 whey protein isolate | 1.25 |
| HiJel S food starch - modified | 0.99 |
| dry egg whites | 0.99 |
| salt | 0.79 |
| GMS 90 emulsifier | 0.59 |
| Baking soda | 0.56 |
| Pan O Lite | 0.45 |
| dry vanilla 1011320 | 0.40 |
| Dicalcium phosphate dihydrate | 0.34 |
| cinnamon | 0.29 |
| Sodium propionate | 0.21 |
| nutmeg | 0.17 |
| xanthan gum | 0.12 |
| Durafax 60 emulsifier | 0.10 |
| ground cloves | 0.07 |
| | 100 |

The spice cake was prepared using the following steps:
Dry Mix Procedure:

Place RCS, Mira-Thik 603, Core M90, and sorbitol into mixer bowl. Melt EC-25 in microwave taking care not to get it too hot. (Do not melt GMS 90 or Durafax 60). Add EC-25, mix 5 minutes on speed 1, scraping bowl as needed. Add Durafax 60 while mixing 1 minute on speed 1, scraping bowl as needed. Add GMS 90 while mixing 1 minute on speed 1, scraping bowl as needed. Run dry mix through a food processor for 2 minutes, scraping after each minute. Transfer dry mix back to mixing bowl. Sift remaining dry ingredients and add slowly (1 large spoonful at a time) to sorbitol mixture while the mixer is running. Mix for a total of 5 minutes on speed 1.

Water Mixing Procedure:

Place dry mix in bowl. Slowly add water while mixing 30 seconds on speed 1. Scrape bowl. Mix 3½ minutes on speed 2, scraping bowl as needed. Spray edges of 8-inch layer cake pan with non-stick spray cooking oil and use a circular parchment paper to line each pan. Pour 450 g batter into each cake pan. Bake at 350° F. for 37 minutes or until done.

Example 36

A cheese sauce comprising an oligosaccharide composition according to the present invention was prepared.
The ingredients were:

| | |
|---|---|
| Cheddar | 23.41 |
| Butter | 5.88 |
| Water | 50.50 |
| Sweet Whey | 5.44 |
| Disodium phosphate (DSP) | 0.73 |
| Trisodium phosphate (TSP) | 0.16 |
| Sodium Citrate | 0.36 |
| Salt | 0.78 |
| MaxiGel 420 starch | 2.73 |
| RCS (Sample 5) | 9.09 |
| Total | 100.0 |

The cheese sauce was prepared using the following steps:
Mix all ingredients. Heat to 200° F. under constant agitation. Hot fill the cheese sauce into jars or containers and seal with lid or closure. Cool to 40° F.

Example 37

A block of imitation mozzarella cheese comprising an oligosaccharide composition according to the present invention was prepared.

The ingredients were:

| | Percent | Weight in g |
|---|---|---|
| Rennet Casein | 19.494 | 974.70 |
| Sorbic Acid | 0.2964 | 14.82 |
| Whey Powder | 1.4288 | 71.44 |
| Soybean Oil | 20.121 | 1006.05 |
| Salt | 2.0007 | 100.04 |
| Sodium Citrate | 2.09 | 104.50 |
| Lactic Acid (liquid) | 1.2692 | 63.46 |
| StaSlim 151 starch | 3.42 | 171.00 |
| Resistant Corn Syrup (Sample 5, 71% ds) | 4.75 | 237.50 |
| Trisodium phosphate (TSP) | 0.76 | 38.00 |
| Water | 44.3699 | 2218.50 |
| Total | 55.6301 | 2781.51 |

The cheese was prepared using the following steps: Add water, sodium citrate, casein, and soybean oil (120 g). Blend for five min. Add remaining soybean oil. Add sorbic acid, salt, starch, resistant corn syrup. Then add whey and lactic acid. Blend for five min. Add remaining ingredients. Cook to 185° F.

Example 38

An edible film comprising an oligosaccharide composition according to the present invention was prepared. Without being bound by theory, it is believed that the oligosaccharide composition served as a plasticizer in the edible film.

The ingredients were:

| | Grams |
|---|---|
| SOLIDS: | |
| Pullulan (PI-20) | 21.252 |
| Star-Dri 1005A maltodextrin | 1.65 |
| RCS (Sample 5, 71% solids) | 3.3 |
| Polysorbate 80 | 0.165 |
| Na Benzoate | 0.033 |
| TOTAL FILM: | 26.4 |
| Solids | 26.4 |
| Water | 83.6 |
| TOTAL | 110 |
| color/flavor mix | 22 |

The edible film was prepared using the following steps:

Dispersion of Ingredients

Mix pullulan and maltodextrin in a beaker with a whisk. Mix water, polysorbate 80, sodium benzoate, and resistant corn syrup (RCS) in a separate beaker. Use a Servodyne Mixer Head model 50003-30 to further mix the wet ingredients. Start with RPM at 700. Slowly add in the dry flavor mix. When all the lumps are gone, slowly add in the pullulan mixture. Adjust the RPM as necessary when the mixture thickens (up to 1,000 RPM). When all the dry ingredients are in, stop the mixer and scrape the sides of the beaker. Turn up the mixer to 1,000 RPM and mix for 2 more minutes. Pour 50 g into centrifuge tubes. Centrifuge for 10 minutes to remove air.

Filming Procedure

Films were drawn using a Gardco adjustable drawdown set at 0.045 in. These drawdowns were adjusted to the proper thickness using feeler gauge blades. Films were drawn onto Mylar with the use of a vacuum plate. The films were dried in an environmental chamber at 65° C. and 25% RH for two hours. They were cured in the environmental chamber at 25° C. and 28% RH overnight. The dried films were packaged into plastic bags.

Example 39

A low fat pound cake comprising an oligosaccharide composition according to the present invention was prepared.

The ingredients were:

| Ingredient | % |
|---|---|
| Part A | |
| Cake flour | 28.81 |
| RCS Solids (Sample 5) | 26 |
| Water | 16.27 |
| GMS-90 Emulsifier | 5.92 |
| dextrose | 4.17 |
| Non-fat dry milk, high heat | 1.6 |
| STA-SLIM 150 starch | 1.29 |
| STA-SLIM 142 starch | 0.64 |
| Salt | 0.63 |
| Leavening acid, Pan-O-Lite | 0.5 |
| Baking soda | 0.5 |
| Vanilla Flavor #464174 | 0.45 |
| Annatto color | 0.1 |
| Xanthan | 0.09 |
| Part B | |
| Liquid egg whites | 8.4 |
| Water | 4.63 |
| | 100 |

The pound cake was prepared using the following steps: Blend dry ingredients of Part A in a Hobart mixer at speed 1. Add GMS-90 emulsifier and blend for 2 minutes (speed 1). Add water and Annatto color and blend 4 minutes (speed 2). Scrape bowl and paddle after 2 minutes of mixing and at end of mixing. Mix Part B ingredients together. Add in ⅓ of the Part B egg white/water mixture to Part A and blend for 1 minute (Speed 2). Scrape bowl and paddle after mixing. Repeat first step for Part B twice to incorporate remaining ⅔ of egg white/water mixture. Pour 200 grams of batter into a loaf pan pre-coated with non-stick spray. Bake at 350° F. for 30 minutes.

Example 40

Oatmeal chocolate chip raisin cookies having polyol levels and comprising an oligosaccharide composition according to the present invention were prepared.

The ingredients were:

| Ingredients | Formula Percent | Baker's Percent |
|---|---|---|
| Vream Rite Shortening | 12.50 | 50.40 |
| BAKERY REBALANCE 706 (Tate & Lyle) | 9.00 | 36.29 |
| STA-LITE III polydextrose (Tate & Lyle) | 5.00 | 20.16 |
| Sorbitol (Sorbogem fines) | 3.00 | 12.10 |
| NutraFlora ® scFOS ® (Fructo Oligosaccharide) | 4.50 | 18.15 |
| Resistant Corn Syrup (Sample 4) | 3.00 | 12.10 |
| Salt | 0.50 | 2.02 |
| Cinnamon | 0.30 | 1.21 |
| Cinnamon flavor | 0.25 | 1.01 |
| Oatmeal cookie flavor | 0.25 | 1.01 |

| Ingredients | Formula Percent | Baker's Percent |
|---|---|---|
| Vanilla flavor | 0.25 | 1.01 |
| Dry egg | 0.90 | 3.63 |
| Water | 9.00 | 36.29 |
| Glycerine | 1.25 | 5.04 |
| Pastry flour | 24.80 | 100.00 |
| Quick rolled oats | 12.40 | 50.00 |
| Baking soda | 0.40 | 1.61 |
| Pan-O-Lite | 0.20 | 0.81 |
| Chopped walnuts | 6.00 | 24.19 |
| Raisins | 6.50 | 26.21 |
| Total | 100.00 | 403.23 |

The oatmeal raisin cookies were prepared using the following steps: Mix shortening and flavors in a N-50 Hobart mixer at speed 1 for 30 seconds. Add the remaining stage 1 ingredients. Mix at speed 1 for 1 min. Scrape the sides of the bowl. Mix at speed 2 for 1 min. Add the stage 2 ingredients. Mix at speed 1 for 1 min. Scrape the sides of the bowl. Mix at speed 2 for 1 min. Add the stage 3 ingredients. Mix at speed 1 for 1 min 30 sec. Scrape the sides of the bowl. Repeat mix at speed 1 for 1 min 30 sec. Add the stage 4 ingredients. Mix at speed 1 for 15 sec. Weigh 30 g dough piece onto a parchment with double-lined baking pans. Bake 12 cookies in convection oven at 375° F. for 11 min.

Example 41

Soft chocolate cookies comprising an oligosaccharide composition according to the present invention were prepared.
The ingredients were:

| Ingredient | % |
|---|---|
| Flour, pastry | 28.70 |
| Resistant corn syrup solids (Sample 5) | 22.20 |
| Butter | 20.40 |
| RCS (Sample 5, 71% ds) | 10.90 |
| Eggs, whole | 9.10 |
| Natural cocoa N-11-N | 3.60 |
| Lightly alkalized cocoa D-11-A | 2.00 |
| Instant TENDER-JEL C food starch modified | 1.90 |
| Vanilla flavor | 0.46 |
| Salt | 0.44 |
| Baking soda | 0.30 |
| | 100.00 |

The cookies were prepared using the following steps: Blend sugar/RCS Solids, butter, and RCS (71% ds) in Hobart mixing bowl on speed 1. Add egg. Dry blend remaining ingredients and add to this mixture. Bake at 350° F. for 15 minutes.

Example 42

A maple syrup comprising an oligosaccharide composition according to the present invention was prepared.
The ingredients were:

| Water | 80.132 |
|---|---|
| Resistant Corn Syrup Solids (Sample 5) | 17.00 |
| Cellulose Gum | 1.00 |
| Maple Flavor | 0.45 |
| Salt | 0.45 |
| SPLENDA sucralose | 0.35 |
| Guar Gum | 0.28 |
| Phosphoric Acid (85%) | 0.15 |
| Caramel Color | 0.13 |
| Sodium Hexameta Phosphate | 0.05 |
| Butter Flavor | 0.008 |
| Total | 100.00 |

The maple syrup was prepared using the following steps: Add sucralose, preservatives, salt, flavoring, and color to water using slow speed in standard mixer. Slowly add gums to mixture, allowing to hydrate 20-25 minutes. Blend in resistant corn syrup solids, while heating to 185° F. Hold for one minute. Remove heat and add acid. Fill containers at 180-185° F. and invert for one minute. Cool to 75° F.

Example 43

A barbeque sauce comprising an oligosaccharide composition according to the present invention was prepared.
The ingredients were:

| Part A | |
|---|---|
| Tomato Paste | 27.23 |
| Water | 14.7 |
| Apple Cider Vinegar | 15.13 |
| Resistant corn syrup (Sample 5, 71%) | 33.73 |
| Molasses | 5.04 |
| Liquid Hickory Smoke | 0.30 |
| Caramel Color | 0.21 |
| Part B | |
| Salt | 2.02 |
| Spice Blend | 1.65 |
| Sucralose | 0.014 |

The barbeque sauce was prepared using the following steps: Heat Part A ingredients on to 190° F. Add dry ingredients to part A and heat for 15 minutes at 200° F. Hot fill containers and cool.

Example 44

A French dressing comprising an oligosaccharide composition according to the present invention was prepared.
The ingredients were:

| Soybean oil | 9.00 |
|---|---|
| Resistant corn syrup (Sample 5, 71%) | 47.57 |
| Vinegar, 120 grain | 12.00 |
| Water | 18.59 |
| Tomato Paste | 7.00 |
| Salt | 2.00 |
| MiraThik 603 food starch modified | 2.00 |
| Polysorbate 60 | 0.20 |
| Onion Powder | 0.18 |
| Garlic Powder | 0.15 |
| Xanthan Gum | 0.10 |
| Sorbic Acid | 0.10 |
| Oleoresin Paprika | 0.10 |
| EDTA | 0.01 |
| Total | 100.0 |

The French dressing was prepared using the following steps: Place water and resistant corn syrup in container. Dry mix onion, salt, garlic, sorbic acid, and EDTA and add to water mixture. Slurry starch and xanthan gum in small amount of oil, add to water mixture, and mix for five minutes to allow starch to hydrate. Add tomato paste and paprika. Add vinegar. Melt polysorbate 60 and add to mixture slowly. Add remaining oil and mix five minutes. Process through a colloid mill at 0.26" (2 revolutions).

Example 45

A cream of chicken soup concentrate comprising an oligosaccharide composition according to the present invention was prepared.
The ingredients were:

|  |  |
| --- | --- |
| Water | 65.65 |
| Chicken Bouillon | 11.30 |
| Resistant Corn Syrup Solids (Sample 5) | 11.00 |
| Half & half | 5.60 |
| Rezista Starch | 3.10 |
| Titanium Dioxide | 1.00 |
| Salt | 0.50 |
| Sugar | 0.16 |
| Spices | 0.69 |
| Xanthan Gum | 0.10 |
| Total | 100.00 |

The cream of chicken soup concentrate was prepared using the following steps: Mix dry ingredients. Mix liquid ingredients for 3-5 minutes. Add dry ingredients slowly using lightning mixer on medium speed. Mix 3-5 minutes ensuring even dispersion. Heat to 190° F. without stirring. Hold for 5 minutes. Fill hot into cans, seal immediately. Retort at 250° F. for 40 minutes. Cool cans to room temperature. To serve, add one can soup to equal volume of 2% milk. Mix well. Heat to simmer (approximately 10 minutes). Serve hot.

Example 46

A ketchup comprising an oligosaccharide composition according to the present invention was prepared.
The ingredients were:

|  |  |
| --- | --- |
| Tomato Paste | 37.54 |
| Resistant Corn Syrup Solids (Sample 5) | 12.01 |
| Water | 41.37 |
| Vinegar 120 grain | 7.01 |
| Garlic Powder | 0.02 |
| Onion Powder | 0.03 |
| Smoke Flavor | 0.001 |
| Salt | 2.00 |
| Sucralose (dry) | 0.02 |

The ketchup was prepared using the following steps: Dry mix spices, RCS, sucralose and salt. Mix water, vinegar, and dry mix using a lightening mixer. Add smoke flavor to wet mix. Blend tomato paste and ¼ of the wet mix (water, vinegar, and dry mix) in a Hobart mixer with paddle attachment on speed 1 for 2 minutes. Blend in the remainder of the wet mix on speed 1 for 1 minute. Stop and scrape the bowl well. Continue blending on speed 1 for 1 minute. Heat ketchup to 105° C. and hold for 15 seconds. Cool to 80° C. Homogenize using Panda homogenizer at 150/50 bars. Immediately package in glass jars.

Example 47

A beef-flavored gravy mix comprising an oligosaccharide composition according to the present invention was prepared.

The ingredients were:

|  |  |
| --- | --- |
| Water | 90.17 |
| Perma-Flo Starch | 3.58 |
| Beef Flavors | 3.25 |
| Resistant Corn Syrup solids (Sample 5) | 10.00 |
| Sugar | 0.43 |
| Sweet Dairy Whey | 0.42 |
| Caramel Color | 0.09 |
| Spices | 0.03 |
| Total | 100.0 |

The beef-flavored gravy mix was prepared using the following steps: Blend dry ingredients and TALO TF-55 flavoring (all ingredients except water) until uniformly blended. Using a wire whisk, disperse this dry mix into cold water. Cook with agitation to 190° F. Hold mixture at 190° F. with agitation for 10 minutes.

Example 48

A dry blended coffee creamer comprising an oligosaccharide composition according to the present invention was prepared.
The ingredients were:

|  |  |
| --- | --- |
| Commercial creamer powder (Jerzee blend 220077) | 21.8 |
| Resistant Corn Syrup solids (Sample 5) | 78.2 |

The dry blended coffee creamer was prepared using the following steps: the ingredients are blended, scaled and screened through a 10 mesh screen into a tumble blender vessel, ribbon blender, or paddle blender. The formulation is blended from 10 to 25 minutes and packaged. Silica dioxide or sodium silicoaluminate can be added as anti-caking agents if required.

Example 49

A soy-based dry coffee creamer powder slurry comprising an oligosaccharide composition according to the present invention was prepared.
The ingredients were:

|  | pounds | solids | % Dry comp | % formula |  |
| --- | --- | --- | --- | --- | --- |
| Hydrogenated Soybean oil 105° F. | 65 | 65 | 50.67% | 23.50% | 48.64 |
| Sodium Caseinate | 4.1 | 3.895 | 3.04% | 1.48% | 3.07 |
| Resistant corn syrup solids (Sample 5) | 61.47 | 58.4 | 45.52% | 22.23% | 46.00 |
| Alphadign 70K Mono- and diglycerides | 0.5 | 0.5 | 0.39% | 0.18% | 0.37 |
| BFP 75K mono- and diglycerides | 0.5 | 0.5 | 0.39% | 0.18% | 0.37 |
| water | 145 | 0 | 0.00% | 52.43% | 108.50 |
| Total solids | 276.57 | 128.3 | 100.00% | 100.00% | 206.95 |
|  | 46.39% |  |  | Yield @ 4% moisture | 100.00 |

The water is added to a batch tank and is heated to 120 to 140° F. The sodium caseinate is added to the water and allowed to hydrate for 10 to 30 minutes. The mono and diglycerides can be melted into the hydrogenated soybean oil or melted separately. Once the sodium caseinate has been hydrated the soybean oil and mono and diglycerides are added to the batch tank. The mixture is well blended. The remaining resistant corn syrup is added to the batch tank and the mixture is heated to 170° F., homogenized via double stage homogenization (if required) and held for 30 minutes. The product is then ready to be spray dried with a inlet temperature of 350 to 500° F. and an exhaust temperature of 150 to 200° F. An optional fluid bed dryer can be used. Sodium silicoaluminate or silica dioxide could also be included for anti-caking purposes. Phosphate salts and/or anti-caking agents could also be included.

Example 50

A coconut-based coffee creamer powder slurry for spray-drying, comprising an oligosaccharide composition according to the present invention was prepared.

The ingredients were:

| Ingredients | pounds | solids | % dry comp | % form | |
|---|---|---|---|---|---|
| Hydrogenated Coconut Oil 92 | 32 | 32 | 48.51% | 21.67% | 46.57 |
| Sodium Caseinate | 3.2 | 3.04 | 4.61% | 2.17% | 4.66 |
| Resistant corn syrup solids (Sample 5) | 31 | 29.45 | 44.65% | 20.99% | 45.12 |
| Dipotassium Phosphate | 0.4 | 0.392 | 0.59% | 0.27% | 0.58 |
| Distilled mono- and diglycerides | 1.08 | 1.08 | 1.64% | 0.73% | 1.57 |
| water | 80 | 0 | 0.00% | 54.17% | 116.43 |
| Total solids | 147.68 44.67% | 65.96 | 100.00% | 100.00% Yield @ 4% moisture | 214.93 100.00 |

A coconut-based coffee creamer powder was prepared using the following steps: The water is added to a batch tank and is heated to 120 to 140° F. The sodium caseinate is added to the water and allowed to hydrate for 10 to 30 minutes. The mono and diglycerides can be melted into the hydrogenated coconut oil or melted separately. Once the sodium caseinate has been hydrated, the coconut oil and mono and diglycerides are added to the batch tank. The mixture is well blended. The remaining ingredients resistant corn syrup and dipotassium phosphate are added to the batch tank and the mixture is heated to 170° F., homogenized via double stage homogenization (if required), and held for 30 minutes. The product is then ready to be spray dried with a inlet temperature of 350 to 500° F. and an exhaust temperature of 150 to 200° F. An optional fluid bed dryer can be used. Sodium silicoaluminate or silica dioxide could also be included for anti-caking purposes.

Example 51

An ice cream coating and/or compound coating can be prepared using resistant corn syrup solids to lower or eliminate sugar content thereby reducing overall calories. Fiber content can be significantly enhanced in comparison to a typical coating, (e.g., this illustration has 33 grams/100 grams versus a comparable control at 5 gram/100 grams of coating).

| Ingredients | percentage |
|---|---|
| Resistant corn syrup solids (sample 5) | 40.5 |
| Vegetable Shortening (92 coconut) | 45.0 |
| Cocoa powder 10/12 (fat) | 14.0 |
| Lecithin | 0.45 |
| sucralose | 0.05 |
| total | 100.00 |

The ice cream coating and/or compound coating can be prepared using the following steps: Grind corn syrup solids to a particle size between 5-125 microns, average near 30-40 micron. Sieve solids to achieve desired particles. Combine cocoa powder and sucralose with corn syrup solids. Melt shortening and combine with lecithin. While mixing the blended dry ingredients, add the melted shortening/lecithin combination, scraping the bowl regularly. Apply to frozen novelties, baked goods, etc. as desired.

Example 52

Two samples of resistant corn syrup (RCS) were prepared as in Sample 5 of Example 16 above, one of which had a lower monosaccharide content. ("LS" in the following description refers to "low sugar.") The wt % d.s.b. of monosaccharides, disaccharides, trisaccharides, and tetra- and higher order saccharides were as follows:

| Formulation | DP1 | DP2 | DP3 | DP4+ |
|---|---|---|---|---|
| RCS | 12.5 | 4.7 | 4.1 | 78.7 |
| RCS LS | 1.6 | 4.6 | 4.6 | 89.2 |

Figure 15:
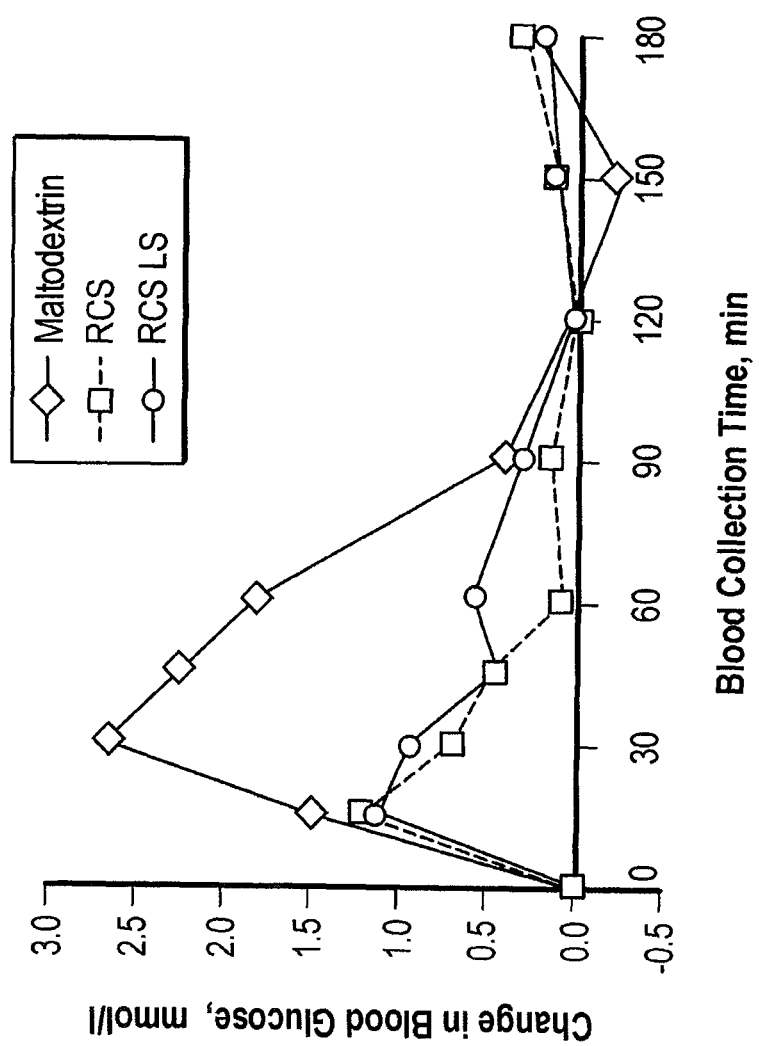
FIG. 15 shows the change in blood glucose concentration in dogs after they were fed either a composition of the present invention or a maltodextrin.

Samples of the two resistant corn syrups and maltodextrin were fed to dogs. Blood samples were taken from the dogs at intervals after the feeding to determine the glycemic response. The changes in blood glucose concentrations over time are shown in FIG. 15, and are summarized in the table below.

| Item | Maltodextrin | RCS | RCS LS | SEM |
|---|---|---|---|---|
| N | 5 | 5 | 5 | |
| Time to glucose peak, min | 30 | 18 | 18 | 4.9 |
| Incremental area under the curve for glucose | 155.1$^d$ | 37.7$^b$ | 73.9$^c$ | 12.9 |
| Relative glycemic response | 100.0$^d$ | 24.5$^b$ | 50.1$^c$ | 7.8 |

$^{ab}$Means in the same row with different superscripts are different (P < 0.05).
SEM = standard error of the mean.

Example 53

Six samples of resistant corn syrup were prepared as in Sample 5 of Example 16 above. Each sample was a 72% ds syrup, with the balance being water. The samples contained essentially no fat, protein, or ash. The six samples were:
RCS GR1 (RCS, 72% ds syrup 70% fiber, 15% sugar) ("sugar" in these samples refers to the total of mono- and disaccharides)
RCS GR2 (RCS LS, 72% ds syrup 80% fiber, 5% sugar)
RCS GR3 (RCS with 50% fructose, 72% ds syrup)
RCS GR4 (RCS with 50% sorbitol, 72% ds syrup)
RCS GR5 (RCS LS with 25% fructose, 72% ds syrup)
RCS GR6 (RCS LS, with 25% sorbitol, 72% ds syrup)

Samples containing 25 g (dsb) of the syrup were prepared as follows. 2.838 kg of filtered water was added to a jug containing a pre-weighed quantity of RCS. The lid was placed on the jug, and it was then mixed thoroughly by shaking and swirling until all syrup was dissolved. 12 oz. (350 g) of this solution contained 25 g of the test carbohydrate on a dry solids basis.

The control solution was prepared by mixing 25 g anhydrous glucose with 300 mL of water.

The samples were administered to 10 healthy human subjects. The characteristics of the subjects were: 5 male, 5 female; age, 35±10 y; body mass index, 24.0±3.8 kg/m². Each subject undertook nine tests on separate days which included the six test foods and on three occasions the standard glucose drink containing 25 g of available carbohydrate. Blood glucose was measured fasting and at 15, 30, 45, 60, 90 and 120 minutes after eating. Incremental areas under the blood glucose response curves (iAUC) were calculated. Each subject's iAUC after consumption of each test food was expressed as a percentage of the mean iAUC of the three glucose controls taken by the same subject. The incremental areas under the curve and relative glycemic response (RGR) of the products were:

|  | iAUC | RGR |
| --- | --- | --- |
| Glucose (25 g) | 124.4 ± 13.5[a] | 100[a] |
| RCS GR1 | 38.5 ± 4.6[b] | 32.6 ± 3.8[b] |
| RCS GR2 | 25.6 ± 3.7[b] | 23.2 ± 4.6[b] |
| RCS GR3 | 30.1 ± 4.4[b] | 26.2 ± 4.2[b] |
| RCS GR4 | 17.4 ± 4.1[b] | 15.3 ± 3.6[c] |
| RCS GR5 | 27.6 ± 4.0[b] | 25.4 ± 4.3[b] |
| RCS GR6 | 20.9 ± 4.0[b] | 18.2 ± 3.5[c] |

Values with different superscripts differ significantly (p < 0.001). There were no statistically significant differences in palatability ratings between any of the foods.

Values with different superscripts differ significantly (p<0.001). There were no statistically significant differences in palatability ratings between any of the foods.

Example 54

Sweetose® 4300 corn syrup (81% ds) was evaporated to less than 6% moisture content by passing it through a hot oil jacketed paddle mixer at a rate of 77 kg/h. The paddle mixer rotor speed was typically set for 300 to 600 rpm and the oil jacket temperature was varied from 150° C. to 205° C. In some of the tests phosphoric acid was added at a rate to give from 0.1% to 0.4% phosphoric acid solids on corn syrup solids. In some of the tests hydrochloric acid was added at 25 ppm, in place of or in addition to the phosphoric acid.

Product collected from these tests (25 mg) was dissolved in 4 mL of pH 4.0 buffer and incubated with 100 microliters of a 10 mg/mL amyloglucosidase enzyme (Amyloglucoxidase Sigma Catalog #A-7255) solution for 2 hours at 45° C. An aliquot from this incubation was treated with a small quantity of ion exchange resin and filtered (0.45 microns) prior to saccharide distribution analysis by liquid chromatography. From this analysis, the weight percent of carbohydrate found to exist as trisaccharides and higher was quantified as digestion resistant carbohydrate and is labeled as % fiber in the table below:

| Sample name | Temp ° C. | % $H_3PO_4$ | HCl ppm | % fiber |
| --- | --- | --- | --- | --- |
| run 1 | 194 | 0.2% |  | 43 |
| run 2 | 195 | 0.2% | 25 | 52 |
| run 3 | 193 | 0.4% | 25 | 62 |
| run 4 | 203 | 0.4% | 25 | 68 |
| run 5 | 180 | 0.2% |  | 27 |
| run 6 | 181 | 0.4% |  | 37 |
| run 7 | 181 | 0.4% | 25 | 33 |
| polydextrose control |  |  |  | 82 |

A laboratory sample of polydextrose was used as a control for this test, and showed a level of approximately 82% fiber.

Example 55

Sweetose® 4300 corn syrup (81% ds) was evaporated to less than 3% moisture content by passing it through a hot oil jacketed paddle mixer at a rate of 77 kg/h. The paddle mixer rotor speed was typically set for 800 rpm and the oil jacket temperature was set to 210° C. In some of the tests phosphoric acid was added at a rate to give from 0.1% to 0.4% phosphoric acid solids on corn syrup solids. In some of the tests hydrochloric acid was added at 25 or 50 ppm, in place of or in addition to the phosphoric acid.

Product collected from these tests (25 mg) was dissolved in 4 mL of pH 4.0 buffer and incubated with 100 microliters of a 10 mg/mL amyloglucosidase enzyme (Amyloglucoxidase Sigma Catalog #A-7255) solution for 2 hours at 45° C. An aliquot from this incubation was treated with a small quantity of ion exchange resin and filtered (0.45 microns) prior to saccharide distribution analysis by liquid chromatography. From this analysis, the weight percent of carbohydrate found to exist as trisaccharides and higher was quantified as digestion resistant carbohydrate and is labeled as % fiber in the table below:

| Sample name | Temp ° C. | % $H_3PO_4$ | HCl ppm | % fiber |
| --- | --- | --- | --- | --- |
| run 2-1 | 210 | 0.0% |  | 11 |
| run 2-2 | 210 | 0.2% |  | 79 |
| run 2-3 | 210 | 0.0% |  | 12 |
| run 2-4 | 210 | 0.1% |  | 43 |
| run 2-5 | 210 | 0.1% |  | 51 |
| run 2-6 | 210 | 0.2% |  | 61 |
| run 2-7 | 210 | 0.3% |  | 84 |
| run 2-8 | 210 | 0.2% | 25 | 79 |
| run 2-9 | 210 | 0.0% |  | 11 |
| run 2-10 | 210 | 0.1% |  | 43 |
| run 2-11 | 210 | 0.1% | 25 | 57 |
| run 2-12 | 210 | 0.2% |  | 53 |
| run 2-13 | 210 | 0.2% | 25 | 62 |
| run 2-14 | 210 | 0.4% |  | 56 |
| run 2-15 | 210 | 0.4% | 25 | 55 |
| run 2-16 | 210 | 0.4% | 50 | 62 |
| run 2-17 | 210 | 0.0% | 50 | 65 |
| run 2-18 | 210 | 0.0% | 50 | 59 |
| polydextrose control |  |  |  | 82 |

A laboratory sample of polydextrose was used as a control for this test, and showed a level of approximately 82% fiber.

Example 56

500 grams of Staley 300 corn syrup (80.0% ds, 35 DE, 0% fiber, 4 kcal/g) was thoroughly blended with 500 grams of resistant corn syrup (69.0% ds, 21 DE, 71% fiber, 2 kcal/g) to give 1 kg of corn syrup fiber (74.5% ds, 28 DE, 35% fiber, 3 kcal/g).

Example 57

500 grams of Staley 1300 corn syrup (80.3% ds, 43 DE, 0% fiber, 4 kcal/g) was thoroughly blended with 500 grams of resistant corn syrup (69.0% ds, 21 DE, 71% fiber, 2 kcal/g) to give 1 kg of corn syrup fiber (74.7% ds, 32 DE, 35% fiber, 3 kcal/g).

Example 58

500 grams of Staley 4300 corn syrup (81.6% ds, 63 DE, 0% fiber, 4 kcal/g) was thoroughly blended with 500 grams of resistant corn syrup (69.0% ds, 21 DE, 71% fiber, 2 kcal/g) to give 1 kg of corn syrup fiber (75.3% ds, 42 DE, 35% fiber, 3 kcal/g).

Example 59

500 grams of Staleydex 130 syrup (70.5% d s, 99 DE, 0% fiber, 4 kcal/g) was thoroughly blended with 500 grams of resistant corn syrup (69.0% ds, 21 DE, 71% fiber, 2 kcal/g) to give 1 kg of corn syrup fiber (69.8% ds, 60 DE, 35% fiber, 3 kcal/g).

The preceding description of specific embodiments of the invention is not intended to be a list of every possible embodiment of the invention. Persons skilled in the art will recognize that other embodiments would be within the scope of the following claims. For example, certain specific slowly digestible or digestion resistant compositions are used as ingredients in food products in some of the above examples. It should be recognized that other slowly digestible or digestion resistant compositions of the present invention could be used instead in those same food products, although the exact characteristics of the food product may vary to some degree depending on the exact nature of the ingredients used. Many other modifications could also be made to the specific examples herein.

The invention claimed is:

1. A blended carbohydrate composition comprising linear and non-linear saccharide oligomers, wherein the blended carbohydrate composition is in the form of a syrup and is prepared by blending corn syrup with a fiber-containing composition containing about 10-70% by weight fiber on a dry solids basis, having at least 50% by weight on a dry solids basis of slowly digestible material, and having a dextrose equivalence of about 25-65, wherein the blended carbohydrate composition contains about 30-40% by weight fiber on a dry solids basis, wherein the blended carbohydrate composition further has a caloric value of about 2.5-3.5 kcal/g, and wherein the fiber-containing composition is prepared by a process that comprises:
(a) providing an aqueous feed composition that comprises at least one monosaccharide or linear saccharide oligomer, that has at least 70% by weight on a dry solids basis of monosaccharides and oligosaccharides having a degree of polymerization of 2-30; and
(b) reacting the feed composition at a solids concentration of at least about 80% by weight with at least one acid that accelerates the rate of cleavage or formation of glucosyl bonds at a temperature of at least about 80° C. for a time sufficient to produce the fiber-containing composition via formation of non-linear saccharide oligomers in an amount greater than the amount of linear saccharide oligomers such that the fiber-containing composition (a) contains about 10-70% by weight fiber on a dry solids basis and (b) has a dextrose equivalence of about 25-65, and (c) is more digestion-resistant than the feed composition.

2. The blended carbohydrate composition of claim 1, wherein the reacting is performed at a pH from about 1.2 to about 2.3.

3. The blended carbohydrate composition of claim 1, consisting essentially of the corn syrup and the fiber-containing composition.

4. A food product that comprises a blended carbohydrate composition according to claim 1.

5. The food product of claim 4, wherein the food product is selected from baked foods, breakfast cereal, dairy products, confections, jams and jellies, beverages, fillings, extruded and sheeted snacks, gelatin desserts, snack bars, cheese and cheese sauces, edible and water-soluble films, soups, syrups, sauces, dressings, creamers, icings, frostings, glazes, pet food, tortillas, meat and fish, dried fruit, infant and toddler food, and batters and breadings.

6. A process for preparing saccharide oligomers, comprising:
providing an aqueous feed composition that comprises at least one monosaccharide or linear saccharide oligomer, and that has at least 70% by weight on a dry solids basis of monosaccharides and oligosaccharides having a degree of polymerization of 2-30; and
reacting the feed composition at a solids concentration of at least about 80% by weight with at least one acid that accelerates the rate of cleavage or formation of glucosyl bonds at a temperature of at least about 80° C. for a time sufficient to cause formation of non-linear saccharide oligomers in an amount greater than the amount of linear saccharide oligomers, wherein a product composition is produced that (a) contains about 10-70% by weight fiber on a dry solids basis, and (b) has a dextrose equivalence of about 25-65, and (c) is more digestion-resistant than the feed composition.

7. The process of claim 6, wherein the acid is residual acid that is present in the feed composition from previous processing.

8. The process of claim 6, wherein the acid is citric acid, hydrochloric acid, sulfuric acid, phosphoric acid, or a combination thereof.

9. The process of claim 6, wherein the pH of the reacting is performed at a from about 1.2 to about 2.3.

10. The process of claim 6, wherein the reaction is performed for a time sufficient to provide the product composition with at least 50% by weight on a dry solids basis of slowly digestible material.

11. The process of claim 6, wherein the aqueous feed composition is formed by a process comprising hydrolysis of starch.

* * * * *

UNITED STATES PATENT AND TRADEMARK OFFICE
CERTIFICATE OF CORRECTION

PATENT NO.         : 8,993,039 B2
APPLICATION NO.    : 11/872791
DATED              : March 31, 2015
INVENTOR(S)        : Michael D. Harrison and Andrew J. Hoffman Page 1 of 1

It is certified that error appears in the above-identified patent and that said Letters Patent is hereby corrected as shown below:

In the Claims

Claim 9, Column 54, line 51, after "performed at a" insert --pH--.

Signed and Sealed this
Fourth Day of August, 2015

Michelle K. Lee
*Director of the United States Patent and Trademark Office*